United States Patent [19]
Abastado et al.

[11] Patent Number: 6,153,408
[45] Date of Patent: Nov. 28, 2000

[54] ALTERED MAJOR HISTOCOMPATIBILITY COMPLEX (MHC) DETERMINANT AND METHODS OF USING THE DETERMINANT

[75] Inventors: Jean-Pierre Abastado; Estelle Mottez; Philippe Kourilsky, all of Paris; Armanda Casrouge, Draveil; David Ojcius, Vincennes; Yu-Chun Lone, Paris, all of France

[73] Assignee: Institut Pasteur and Institut National de la Sante et de la Recherche Medicale, Paris, France

[21] Appl. No.: 08/370,476

[22] Filed: Jan. 9, 1995

Related U.S. Application Data

[63] Continuation of application No. 08/117,575, Sep. 7, 1993, abandoned, which is a continuation-in-part of application No. 08/072,787, Jun. 7, 1993, abandoned, which is a continuation-in-part of application No. 07/801,818, Dec. 5, 1991, abandoned, which is a continuation of application No. 07/792,473, Nov. 15, 1991, abandoned.

[51] Int. Cl.[7] .......................... C07K 19/00; C12N 15/62; C12N 15/85; A61K 39/385
[52] U.S. Cl. ............... 435/69.7; 435/252.3; 435/320.1; 530/350; 530/386; 530/391; 530/394; 530/395; 536/234
[58] Field of Search ..................... 530/350, 386, 530/392, 394, 395, 391; 435/69.7, 252.3, 320.1; 536/23.4

[56] References Cited

U.S. PATENT DOCUMENTS

| | | | |
|---|---|---|---|
| 4,478,823 | 10/1984 | Sanderson | 424/88 |
| 4,946,778 | 8/1990 | Ladner | 435/69.6 |
| 5,242,687 | 9/1993 | Tykocinski et al. | 424/93 |
| 5,260,422 | 11/1993 | Clark et al. | 530/403 |
| 5,528,498 | 6/1996 | Huston et al. | 530/350 |
| 5,583,031 | 12/1996 | Stern | 435/240.2 |

FOREIGN PATENT DOCUMENTS 9112332   8/1991   WIPO .

OTHER PUBLICATIONS

Lone, Y.–C., et al., International Immunology, vol. 6, No. 10, "Role of the CDR1 region of the TCR B–chain in the binding to purified MHC–peptide complex", pp. 1561–1565, 1994.

Abastado, J.–P., et al., Journal of Experimental Medicine, vol. 182, No. 8, "Dimerization of Soluble Major Histocompatibility Complex–Peptide Complexes Is Sufficient for Activation of T Cell Hybridoma and Induction of Unresponsiveness", pp. 439–447, 1995.

Gill, R. F., et al., Journal of Immunological Methods, vol. 176, "Systematic Identification of H–2 Kd binding peptides and induction of peptide specific CTL", pp. 245–253, 1994.

Quesnel, A., et al., Peptide Research, vol. 8, No. 1, "Use of Synthetic Peptide Libraries for the H–2Kd Binding Motif Identification", pp. 44–51, 1995.

Germain, R. N., in Fundamental Immunology, 3rd Edition, Paul, W. E., Ed., Raven Press, New York, "Antigen Processing and Presentation", pp. 646–650, 1993.

(List continued on next page.)

*Primary Examiner*—Robert A. Wax
*Assistant Examiner*—William W. Moore
*Attorney, Agent, or Firm*—Finnegan, Henderson, Farabow, Garrett & Dunner, L.L.P.

[57] ABSTRACT

An altered MHC class I determinant comprises $\alpha_1$, $\alpha_2$, $\alpha_3$, $\beta_2$-microglobulin ($\beta_2$m) polypeptide domains encoded by a mammalian MHC class I locus in which the $\alpha_3$ domain is covalently linked to the $\beta_2$M domain. An altered MHC class II determinant comprises $\alpha_1$, $\alpha_2$, $\beta_1$, and $\beta_2$ polypeptide domains encoded by a mammalian MHC class II locus, in which the domains are covalently linked to form a polypeptide comprising the $\beta_2$-$\alpha_2$-$\alpha_1$-$\beta_1$ domains in sequence. The altered MHC class I and class II determinants can be associated with an antigen to elicit an immune response. The invention can be used in the immunization or treatment of diseases such as AIDS, multiple sclerosis, lupus erythematosus, toxic shock or snake bite.

42 Claims, 19 Drawing Sheets

OTHER PUBLICATIONS

Smiley, S.T., et al., Proceedings of the National Academy of Sciences, U.S.A., vol. 93, "Truncation of the class II beta–chain cytoplasmic domain influences the level of class II/invariant chain–derived peptide complexes", pp. 241–244, 1996.

Ocjius, P. M. et al., 1993, Biochemical and Biophysical Research Communications, 197(3): 1216–1222.

Mottez, E., et al., 1991, European Journal of Immunology, 21: 467–471.

Maryanski, J. L., et al., 1989, European Journal of Immunology, 19: 193–196.

Novotny, J., et al., 1989, Research in Immunology, 140: 145–158.

Abastado, J.–P. et al., 1989, Research in Immunology, 140: 581–594.

Godeau, F., et al., 1992, The Journal of Biological Chemistry, 267(34): 24223–24229.

Jaulin, C., et al., 1992, Journal of Immunology 149(12): 3990–3994.

Ojcius, P. M., et al., 1993, European Journal of Immunology 23: 1118–1124.

Choppin, J., et al., 1990, Journal of Experimental Medicine, 172: 889–899.

Mottez et al., "A single–chain murine class I major transplantation antigen", Eur. J. Immunol. 21: 467–471 (1991).

Rock et al., "Reassociation with beta2–microglobulin is necessary for Db class I major histocompatibility complex binding of an exogenous influenza peptide", Proc. Natl. Acad. Sci. USA 88: 301–304 (1991).

Rock et al., "Dissociation of beta2–microglobulin leads to the accumulation of a substantial pool of inactive class I MHC heavy chains on the cell surface", Cell 65: 611–620 (1991).

Elliot et al., "Peptide–induced conformational change of the class I heavy chain", Nature 351: 402–406 (1991).

Huston et al., "Protein engineering of antibody binding sites: Recovery of specific activity in an anti–digoxin single–chain Fv analogue produced in *Escherichia coli*", Proc. Natl. Acad. Sci. USA 85: 5879–5883 (1988).

Novotny et al., "A soluble, single–chain T–cell receptor fragment endowed with antigen–combining properties", Proc. Natl. Acad. Sci. USA 88: 8646–8650 (1991).

Roitt et al., ed. "Immunology", Gower Medical Publishing, 1985 p. 4.7.

FIG. 5(B)

SC-10
AAG CTG GGG GGG ATC GGA TCC GGT GGC GGT TCG ATC CAG
TTC GAC CCC CCC TAG CCT AGG CCA CCG CCA AGC TAG GTC
Gly Gly Ile Gly Ser Gly Gly Gly Gly Ser

SC-13
AAG CTG GGG GGG ATC GGA TCA GGC GGA TCC GGT GGC GGT TCG ATC CAG
TTC GAC CCC CCC TAG CCT AGT CCG CCT AGG CCA CCG CCA AGC TAG GTC
Gly Gly Ile Gly Ser Gly Gly Ser Gly Gly Gly Gly Ser

SC-15
AAG CTG GGG GGG ATC GGA TCC GGA TCC GGT GGC GGC CGT TCG ATC CAG
TTC GAC CCC CCC TAG CCT AGG CCT AGG CCA CCG CCG CCA AGC TAG GTC
Gly Gly Ile Gly Ser Gly Gly Ser Gly Gly Gly Gly Ser

SC-17
AAG CTG GGG GGG ATC GGA TCA GGC TCT GGA GGT GGC GGA TCC GGT GGC GGC CCT CCG GGT TCG ATC CAG
TTC GAC CCC CCC TAG CCT AGT CCG AGA CCT CCA CCG CCT AGG CCA CCG CCG GGA AGC CCA AGC TAG GTC
Gly Gly Ile Gly Ser Gly Gly Ser Gly Gly Gly Gly Ser Gly Gly Gly Gly Ser

SC-19
AAG CTG GGG GGG ATC GGA TCA GGC GGA GGT GGA TCT GGA GGT GGC GGA TCC GGT GGC GGC CCT AGG CCA CCG CCT AGG CCA CCG GGT TCG ATC CAG
TTC GAC CCC CCC TAG CCT AGT CCG CCT CCA CCT AGA CCT CCA CCG CCT AGG CCA CCG CCG GGA TCC CCA AGC TAG GTC
Gly Gly Ile Gly Ser Gly Gly Ser Gly Gly Gly Gly Ser Gly Gly Gly Gly Ser

SC-21
AAG CTG GGG GGG ATC GGA TCA GGC GGA GGT GGA TCC GGT GGA GGT GGC GGA TCC GGT GGC GGC GGT TCG ATC CAG
TTC GAC CCC CCC TAG CCT AGT CCG CCT CCA CCT AGG CCA CCT CCA CCG CCT AGG CCA CCG CCA AGC TAG GTC
Gly Gly Ile Gly Ser Gly Gly Ser Gly Gly Gly Gly Ser Gly Gly Gly Gly Ser

FIG. 6(A)
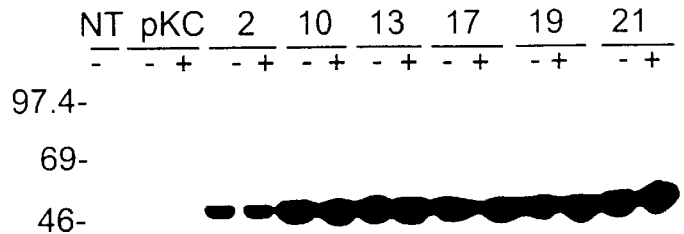
FIG. 6(B)
FIG. 6(C)
FIG. 6(D)

TCRcDNA V+C CW3P-> 1-phase Translation
DNA sequence 819 b.p. ATGCGTCCTGGC ... TGGTCCAGTTGA LINEAR ►LEADER
1/1                                    31/11                              ►Vα8p71
ATG CGT CCT GGC ACC TGC TCA GTT CTT GTG CTC CTC CTA ATG CTC agg agg tca aat ggc
Met arg pro gly thr cys ser val leu val leu leu leu met leu arg arg ser asn gly
61/21                                  91/31
gac gga gac TCA GTG ACC CAG ACA GAA GGC CTG GTC ACT CTC ACC GAG GGG TTG CCT GTG
asp gly asp ser val thr gln thr glu gly leu val thr leu thr glu gly leu pro val
121/41                                 151/51
ATG CTG AAC TGC ACC TAT CAG CAT ATT TAC TCA AAT CCT TTC CTT TTC TGG TAT GTG CAC
met leu asn cys thr tyr gln his ile tyr ser asn pro phe leu phe trp tyr val his
181/61                                 211/71
TAT CTC AAT GAA TCC CCT CGG CTA CTC CTG AAG AGC TCC ACA GAC AAC AAG AGG ACC GAG
tyr leu asn glu ser pro arg leu leu leu lys ser ser thr asp asn lys arg thr glu
241/81                                 271/91
CAC CAA GGG TTC CAC GCC ACT CTC CAT AAG AGC AGC AGC TCC TTC CAT CTG CAG AAG TCC
his gln gly phe his ala thr leu his lys ser ser ser ser phe his leu gln lys ser
301/101                                331/111
TCA GCG CAG CTG TCA GAC TCT GCC CTG TAC TAC TGT GCT ttg agt gag ggg ggc ttt gca
ser ala gln leu ser asp ser ala leu tyr tyr cys ala leu ser glu gly gly phe ala
361/121    ►JαpHDS58                   391/131              ►Cα
agt gcg ctg ACA TTT GGA TCT GGC ACA AAA GTC ATT GTT CTA CCA GAC ATC CAG AAC CCA
ser ala leu thr phe gly ser gly thr lys val ile val leu pro asp ile gln asn pro
421/141                                451/151
GAA CCT GCT GTG TAC CAG TTA AAA GAT CCT CGG TCT CAG GAC AGC ACC CTC TGC CTG TTC
glu pro ala val tyr gln leu lys asp pro arg ser gln asp ser thr leu cys leu phe
481/161                                511/171
ACC GAC TTT GAC TCC CAA ATC AAT GTG CCG AAA ACC ATG GAA TCT GGA ACG TTC ATC ACT
thr asp phe asp ser gln ile asn val pro lys thr met glu ser gly thr phe ile thr
541/181                                571/191
GAC AAA ACT GTG CTC GAC ATG AAA GCT ATG GAT TCC AAG AGC AAT GGG GCC ATT GCC TGG
asp lys thr val leu asp met lys ala met asp ser lys ser asn gly ala ile ala trp
601/201                                631/211
AGC AAC CAG ACA AGC TTC ACC TGC CAA GAT ATC TTC AAA GAG ACC AAC GCC ACC TAC CCC
ser asn gln thr ser phe thr cys gln asp ile phe lys glu thr asn ala thr tyr pro

FIG. 9A

```
661/221                              691/231
AGT TCA GAC GTT CCC TGT GAT GCC ACG TTG ACT GAG AAA AGC TTT GAA ACA GAT ATG AAC
ser ser asp val pro cys asp ala thr leu thr glu lys ser phe glu thr asp met asn
721/241                              751/251
CTA AAC TTT CAA AAC CTG TCA GTT ATG GGA CTC CGA ATC CTC CTG CTG AAA GTA GCC GGA
leu asn phe gln asn leu ser val met gly leu arg ile leu leu leu lys val ala gly
781/261                              811/271
TTT AAC CTG CTC ATG ACG CTG AGG CTG TGG TCC AGT TGA
phe asn leu leu met thr leu arg leu trp ser ser OPA
```

THE COMPOSITION OF TCR α CW$^3$/1.1:LEADER, V$_α$ 8$_p$ 71, J$_α$ pHDS58, C$_α$

FIG. 9A (CONT.)

B2-CW3 TCR CDNA2 [1 TO 909] -> 1-Phase Translation

DNA SEQUENCE  909 b.p.    ATGGGCTGTAGG ... AAAAATTCCTGA LINEAR

```
  ┌─►LEADER
  │1/1                              31/11                    ┌─►Vβ10
  │atg ggc tgt agg ctc cta agc tgt gtg gcc ttc tgc ctc ttg gga ata ggc│CCT TTG GAG
   Met gly cys arg leu leu ser cys val ala phe cys leu leu gly ile gly│pro leu glu
   61/21                                   91/31
   ACG GCT GTT TTC CAG ACT CCA AAC TAT CAT GTC ACA CAG GTG GGA AAT GAA GTG TCT TTC
   thr ala val phe gln thr pro asn tyr his val thr gln val gly asn glu val ser phe
   121/41                                  151/51
   AAT TGT AAG CAA ACT CTG GGC CAC GAT ACT ATG TAT TGG TAC AAG CAA GAC TCT AAG AAA
   asn cys lys gln thr leu gly his asp thr met tyr trp tyr lys gln asp ser lys lys
   181/61                                  211/71
   TTG CTG AAG ATT ATG TTT AGC TAC AAT AAT AAG CAA CTC ATT GTA AAC GAA ACA GTT CCA
   leu leu lys ile met phe ser tyr asn asn lys gln leu ile val asn glu thr val pro
   241/81                                  271/91
   AGG CGC TTC TCA CCT CAG TCT TCA GAT AAA GCT CAT TTG AAT CTT CGA ATC AAG TCT GTA
   arg arg phe ser pro gln ser ser asp lys ala his leu asn leu arg ile lys ser val
   301/101                                 331/111                   ┌─►Jβ1.2
   GAG CCG GAG GAC TCT GCT GTG TAT CTC TGT GCC AGC AGC CTC GGC TCC GAC TAC│ACC TTC
   glu pro glu asp ser ala val tyr leu cys ala ser ser leu gly ser asp tyr│thr phe
                             ┌─►Cβ 391/131
   361/121                   │
   GGC TCA GGG ACC AGG CTT TTG GTA CTC│GAG GAT CTG AGA AAT GTG ACT CCA CCC AAG GTC
   gly ser gly thr arg leu leu val leu│glu asp leu arg asn val thr pro pro lys val
   421/141                                 451/151
   TCC TTG TTT GAG CCA TCA AAA GCA GAG ATT GCA AAC AAA CAA AAG GCT ACC CTC GTG TGC
   ser leu phe glu pro ser lys ala glu ile ala asn lys gln lys ala thr leu val cys
   481/161                                 511/171
   TTG GCC AGG GGC TTC TTC CCT GAC CAC GTG GAG CTG AGC TGG TGG GTG AAT GGC AAG GAG
   leu ala arg gly phe phe pro asp his val glu leu ser trp trp val asn gly lys glu
   541/181                                 571/191
   GTC CAC AGT GGG GTC AGC ACG GAC CCT CAG GCC TAC AAG GAG AGC AAT TAT AGC TAC TGC
   val his ser gly val ser thr asp pro gln ala tyr lys glu ser asn tyr ser tyr cys
   601/201                                 631/211
   CTG AGC AGC CGC CTG AGG GTC TCT GCT ACC TTC TGG CAC AAT CCT CGA AAC CAC TTC CGC
   leu ser ser arg leu arg val ser ala thr phe trp his asn pro arg asn his phe arg
```

FIG. 9B

```
661/221                                 691/231
TGC CAA GTG CAG TTC CAT GGG CTT TCA GAG GAG GAC AAG TGG CCA GAG GGC TCA CCC AAA
cys gln val gln phe his gly leu ser glu glu asp lys trp pro glu gly ser pro lys
721/241                                 751/251
CCT GTC ACA CAG AAC ATC AGT GCA GAG GCC TGG GGC CGA GCA GAC TGT GGA ATC ACT TCA
pro val thr gln asn ile ser ala glu ala trp gly arg ala asp cys gly ile thr ser
781/261                                 811/271
GCA TCC TAT CAT CAG GGG GTT CTG TCT GCA ACC ATC CTC TAT GAG ATC CTA CTG GGG AAG
ala ser tyr his gln gly val leu ser ala thr ile leu tyr glu ile leu leu gly lys
841/281                                 871/291
GCC ACC CTA TAT GCT GTG CTG GTC AGT GGC CTA GTG CTG ATG GCC ATG GTC AAG AAA AAA
ala thr leu tyr ala val leu val ser gly leu val leu met ala met val lys lys lys
901/301
AAT TCC TGA
asn ser OPA
```

THE COMPLETION OF TCR β CW β1.1:LEADER, V β1.0, J β1.2, Cβ

FIG 9B (CONT.)

| PEPTIDE | SEQUENCE |
|---|---|
| CW3 | RYLKNGKETL |
| Y81 | YIPSAEKI |

FIG. 11

○ ALTERED Kd MOLECULE

∼ CW3 PEPTIDE

|| a-z/b-z TCR

⊥ SF1.1.1.1 ANTI-Kd ANTIBODY

ALTERED MAJOR HISTOCOMPATIBILITY COMPLEX (MHC) DETERMINANT AND METHODS OF USING THE DETERMINANT

CROSS-REFERENCE TO RELATED APPLICATION

This application is a continuation of application Ser. No. 08/117,575, filed Sep. 7, 1993, now abandoned which is a continuation-in-part of application Ser. No. 08/072,787, filed Jun. 7, 1993 (Atty. Docket No. 05243.0001-00000), now abandoned which is a continuation-in-part of application Ser. No. 07/801,818, filed Dec. 5, 1991 (Atty. Docket No. 03495.0106-01000), now abandoned, which is a continuation of application Ser. No. 07/792,473, filed Nov. 15, 1991 (Atty. Docket No. 03495-0106) and now abandoned. The entire disclosure of application Ser. Nos. 08/072,787, 07/801,818 and 07/792,473 are relied upon and incorporated by reference herein.

BACKGROUND OF THE INVENTION

This invention relates to an altered major histocompatibility complex (MHC) determinant and to the altered MHC determinant in association with an antigen. This invention also relates to the use of the altered MHC determinant in diagnostic applications and for treating or immunizing a mammal.

The major histocompatibility complex is a series of genes that code for protein molecules responsible for cell—cell recognition and interaction. The MHC of mammalian species contains three groups of genes: class I, class II, and class III. Class I and class II genes code for cell surface recognition molecules. Class III genes code for certain complement components.

The ability of cells to recognize other cells as self or as originating from another genetically different individual (non-self) is an important property in maintaining the integrity of tissue and organ structure. Class I and class II MHC products control recognition of self and non-self. The major histocompatibility system thus prevents an individual from being invaded by cells from another individual. For example, transplants from one individual generally cannot survive in another individual because of histocompatibility differences.

Histocompatibility similarities are required for cellular cooperation in induction of the immune response, and they provide a mechanism to ensure that T cells and B cells of a given individual can recognize each other for cooperation, yet recognize foreign structures at the same time. For instance, T lymphocytes, when presented with an antigen in the proper manner, react in one of two ways: through the generation of T cytotoxic lymphocytes ($T_c$) or through amplification by T helper cells ($T_h$) or suppression by T suppressor cells ($T_s$) of the effects of other T or B cells. In general, T lymphocytes only recognize the antigen and respond to it when it is presented on the surface of antigen-presenting cell. This antigen-presenting cell may vary according to the type of T lymphocyte involved. Thus, in the generation of cytotoxic responses, lymphocytes and possibly macrophages present the antigen to the $T_c$ cells, while in the other types of T response the presenting cell may be a macrophage and perhaps dendritic cells.

T cells need to recognize two structures, a foreign antigen and an MHC gene product, for their subsequent activation. The process of generating $T_c$ cells and a cytotoxic response requires that the antigen be presented to the T cells in association with an MHC class I gene product. On the other hand, for B cells to be activated, binding to the antigen is necessary, plus a second signal usually given by a $T_h$ lymphocyte. However, the $T_h$ lymphocytes require the presentation of the antigen in a processed form by an antigen-presenting cell in the context of an MHC class II determinant.

In the case of B cell activation, it has been established that whatever the antigen-presenting cell is, it must process the antigen before presenting it to the $T_h$ lymphocytes. This involves taking up the antigen, sequestering it in intracellular compartments, and re-expressing the antigen or a portion thereof on the surface of the antigen-presenting cell in association with a class II MHC determinant. The $T_h$ cell must be able to recognize the processed antigen and class II markers on both the antigen-presenting cell and the B cell. When each of these requirements is fulfilled, the B cell will be stimulated to proliferate, which greatly increases the number of cells capable of synthesizing specific antibody. These then differentiate into plasma cells, which secrete large amounts of antibody. A similar response employing class II receptors on $T_s$ suppressor cells and class II MHC markers on macrophages and B cells may be operative in induction of T suppressor activity, which turns off antibody production.

Much remains to be understood of the interactions between antigens and MHC class I and class II molecules, and of the way in which T cell receptors recognize MHC-antigen complexes. For instance, a large proportion of MHC molecules is likely to be occupied by a variety of preexisting (probably endogenous) peptides. This obscures the interpretation of peptide-binding assays and hampers crystallographic studies of peptide-MHC complexes. It would be extremely useful to be able to isolate peptide-free MHC molecules, which could be loaded by a single type of peptide.

In addition, there exists a need in the art for knowledge of the peptide motifs of individual MHC alleles to aid in making T-cell epitope predictions, to aid in synthetic or recombinant vaccine development, and for intervention in autoimmune diseases or graft rejection.

SUMMARY OF THE INVENTION

This invention aids in fulfilling these needs in the art. More particularly, this invention provides a MHC class I determinant comprising $\alpha_1$, $\alpha_2$, $\alpha_3$, and $\beta_2$-microglobulin polypeptide domains encoded by a mammalian MHC class I locus. The $\alpha_3$ domain has a carboxyl terminus, and the $\beta_2$-microglobulin domain has an amino terminus that is covalently linked to the carboxyl terminus of the $\alpha_3$ domain.

This invention also provides a MHC class II determinant comprising $\alpha_1$, $\alpha_2$, $\beta_1$, and $\beta_2$ polypeptide domains encoded by a mammalian MHC class II locus. The domains are covalently linked to form a polypeptide comprising the $\beta_2$-$\alpha_2$-$\alpha_1$-$\beta_1$ domains in sequence.

In addition, this invention provides a recombinant DNA molecule comprising the MHC class I determinant or the MHC class II determinant of the invention inserted in a vector.

Further, this invention provides a host transformed with the vector of the invention.

Also, this invention provides a composition comprising an antigen bound to the MHC class I determinant or the MHC class II determinant of the invention.

Moreover, this invention provides a method of eliciting an immune system response in a mammal. The method comprises administering to the mammal an effective amount of the MHC class I or class II determinant of the invention, with or without association with an antigen.

Although native MHC molecules can be highly complicated structures not lending themselves to convenient manipulation, the present invention demonstrates the feasibility of creating MHC-antigen complexes between any of a variety of molecules capable of fulfilling the task of target recognition. These molecules are easier to handle and refold during and after denaturing treatments. These constructs are useful in the analysis of functional interactions between the various domains comprising the MHC molecules.

Moreover, this invention makes it possible to intervene in the functioning of the immune system. The immune system cells are capable of recognizing the altered MHC determinants and compositions of the invention and to respond to the presence of a potential pathogen with an effector appropriate to its lineage, e.g., cytotoxic T lymphocytes would respond by cytotoxic activity against the target, and B lymphocytes are activated to synthesize antibody. Macrophages and granulocytes carry out their effector functions, including cytokine release, phagocytosis, and reactive oxygen generation after intervention by the altered MHC determinants and compositions of the invention. Similarly, with an antigen or peptide portion typical as a marker for tumor cells, the immune system response to the tumor is beneficially elevated. In addition, with an antigen capable of causing recognition of immune cells having an inappropriate reactivity with self-determinants, this invention makes it possible to selectively target cells for destruction.

BRIEF DESCRIPTION OF THE DRAWINGS

This invention will be described in greater detail by referring to the drawings in which:

FIG. 6 shows the immunodetection of intracellular SC-$K^d$ molecules:

(A) Immunoprecipitation of SC-$K^d$-2, -10, -13, -17, -19, -21 by mAb 34-1-2. NT refers to "non-transfected" and pKC refers to transfection by the vector. Transfections were made in the absence (−) or in the presence (+) of a peptide (NPR⁻) added at a concentration of $10^{-4}$ M in the culture medium.

(B) Immunoprecipitation of SC-$K^d$-2, -15 by monoclonal antibody (mAb) 34-1-2 (left), F23-1 (middle) and 20-8-4 (right). Symbols as above.

(C) Immunoprecipitation of SC-$K^d$-15 treated (+) and non-treated (0) with Endo H.

(D) Overexposed autoradiogram [3 weeks instead of 2 days in (A) and (B)] showing the presumptive monkey $\beta_2$-microglobulin band, which is co-precipitated by 34-1-2 in larger relative amounts with SC-$K^d$-2 than with SC-$K^d$-15 (on top, with a 2-day exposure).

Figure 7:
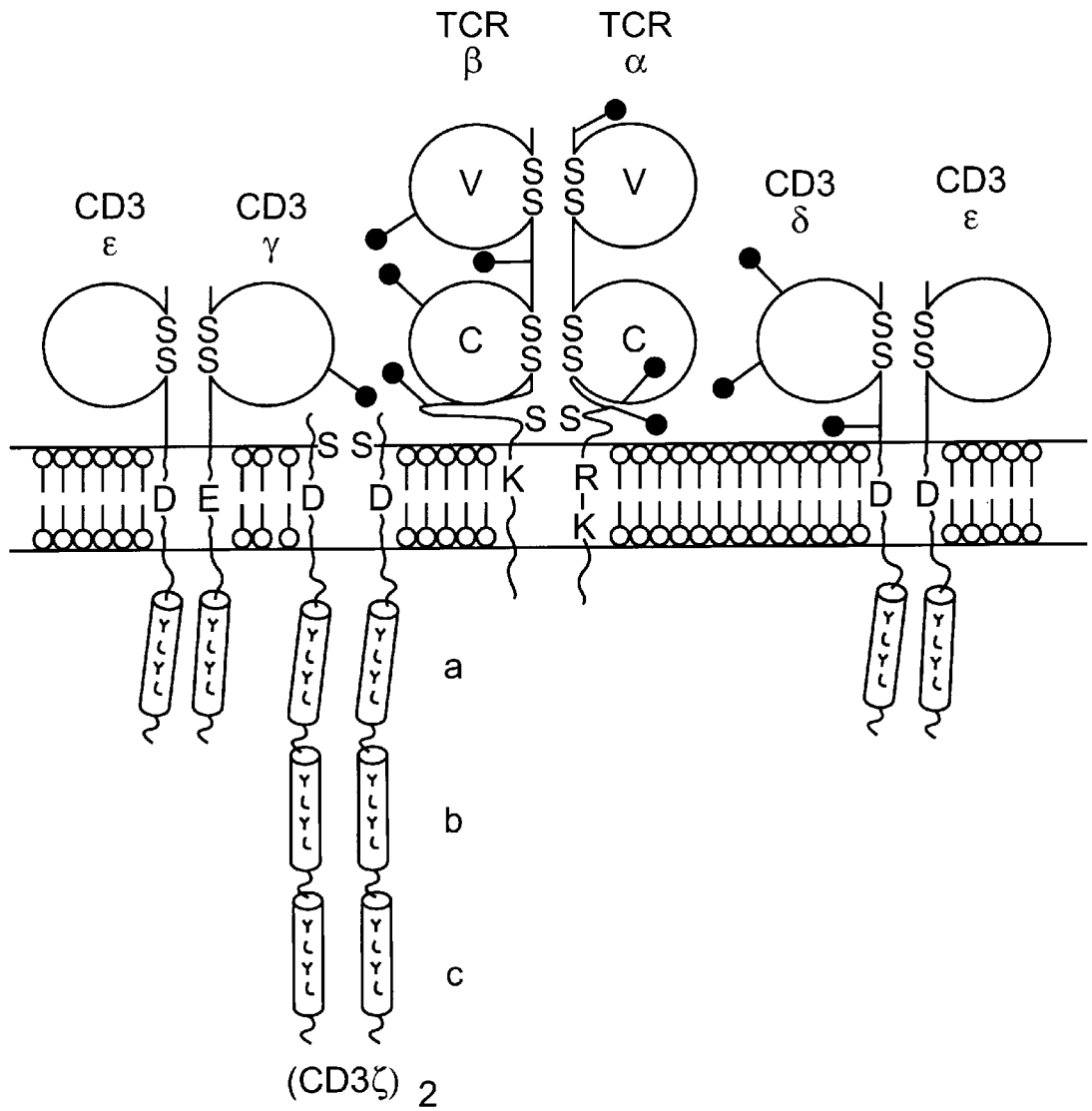

FIG. 7 depicts the CD3-TCR complex.

Figure 8:
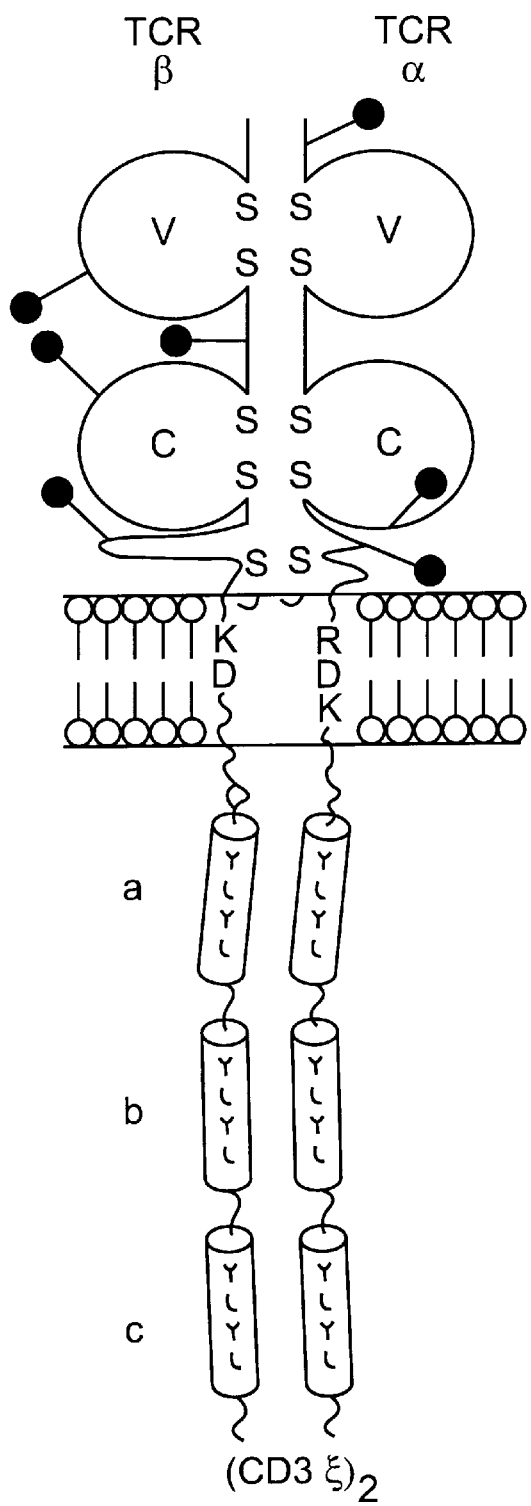

FIG. 8 depicts the TCRα-ξ/β-ξ fusion construct.

FIG. 9 is the nucleotide sequence of the α and β chains of the TCR of the CW3/1.1 CTL clone.

Figure 10:
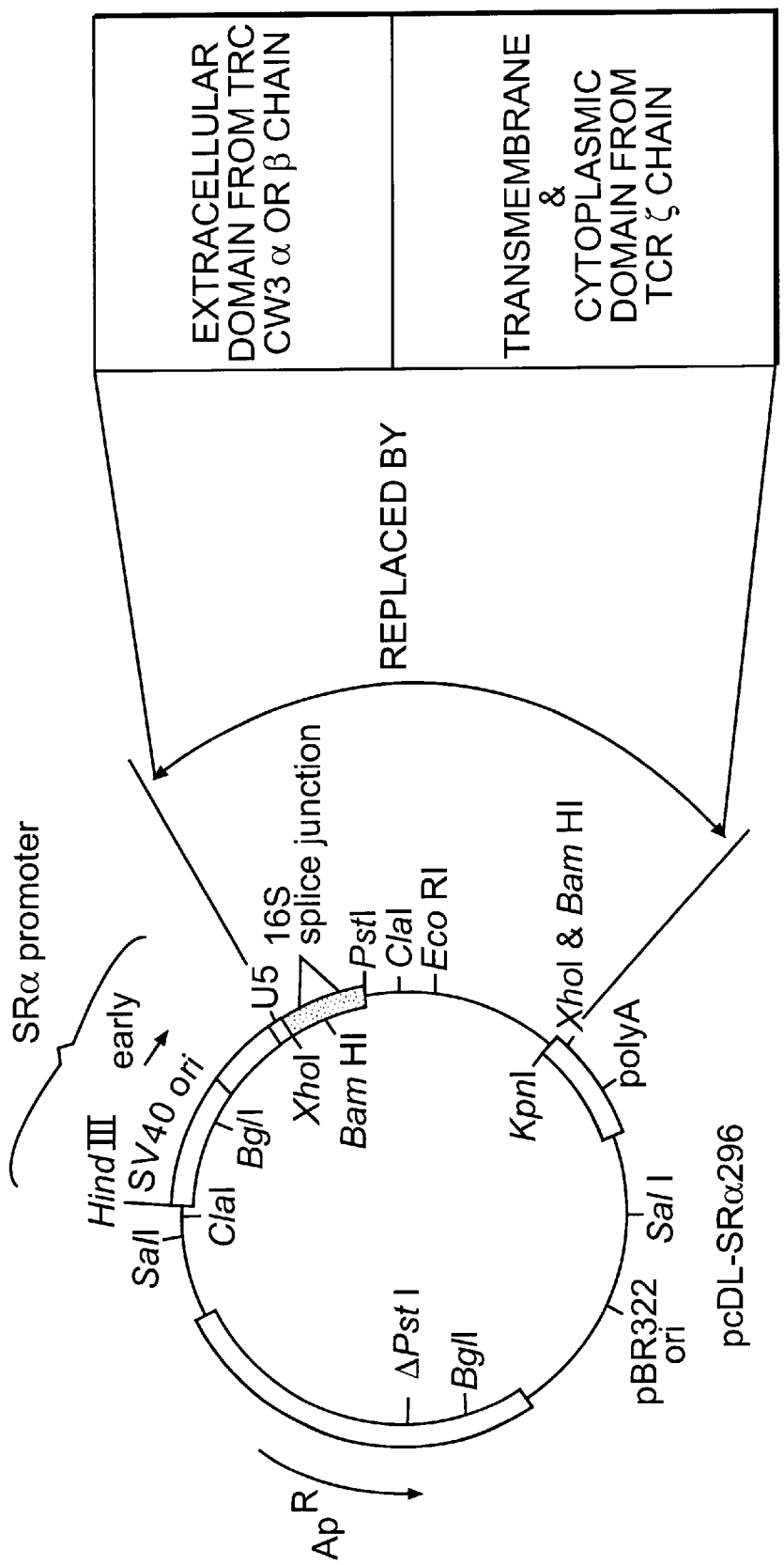

FIG. 10 is a plasmid map of pCDL-SRα296.

FIG. 11 is the nucleotide sequence of peptides CW3 and Y81.

Figure 12:
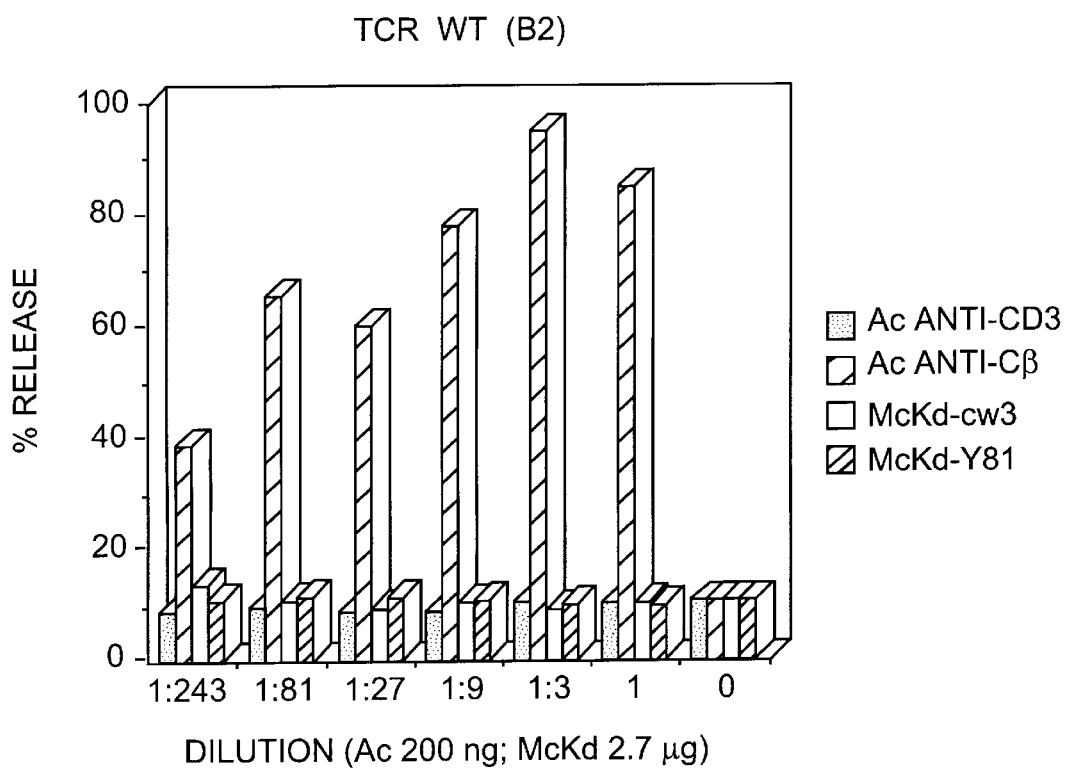

FIG. 12 is a diagram which shows that the altered MHC $K^d$ molecule does not activate the RBL-transfectant.

Figure 13:
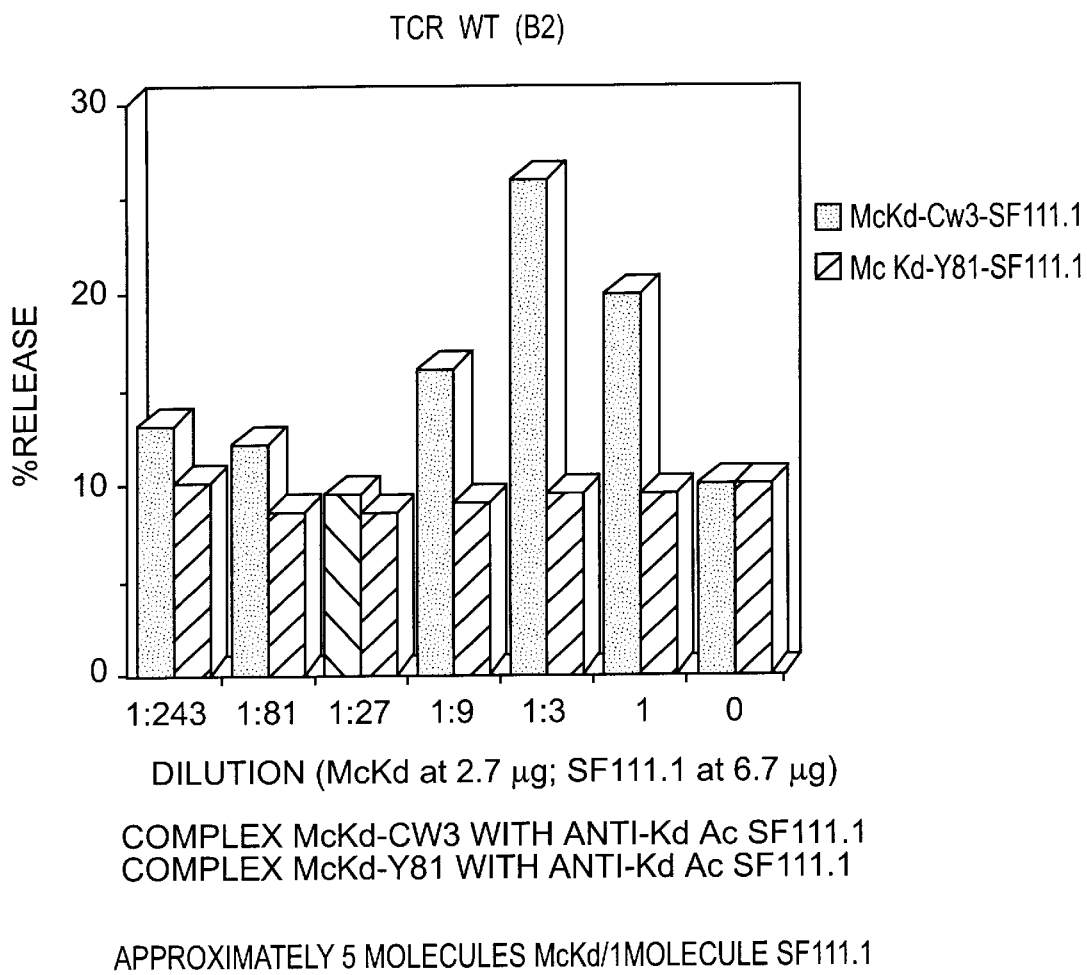

FIG. 13 is a diagram showing that the altered $K^d$ molecule activates the RBL transfectant in the presence of the SF1-1.1.1 antibody.

Figure 14:
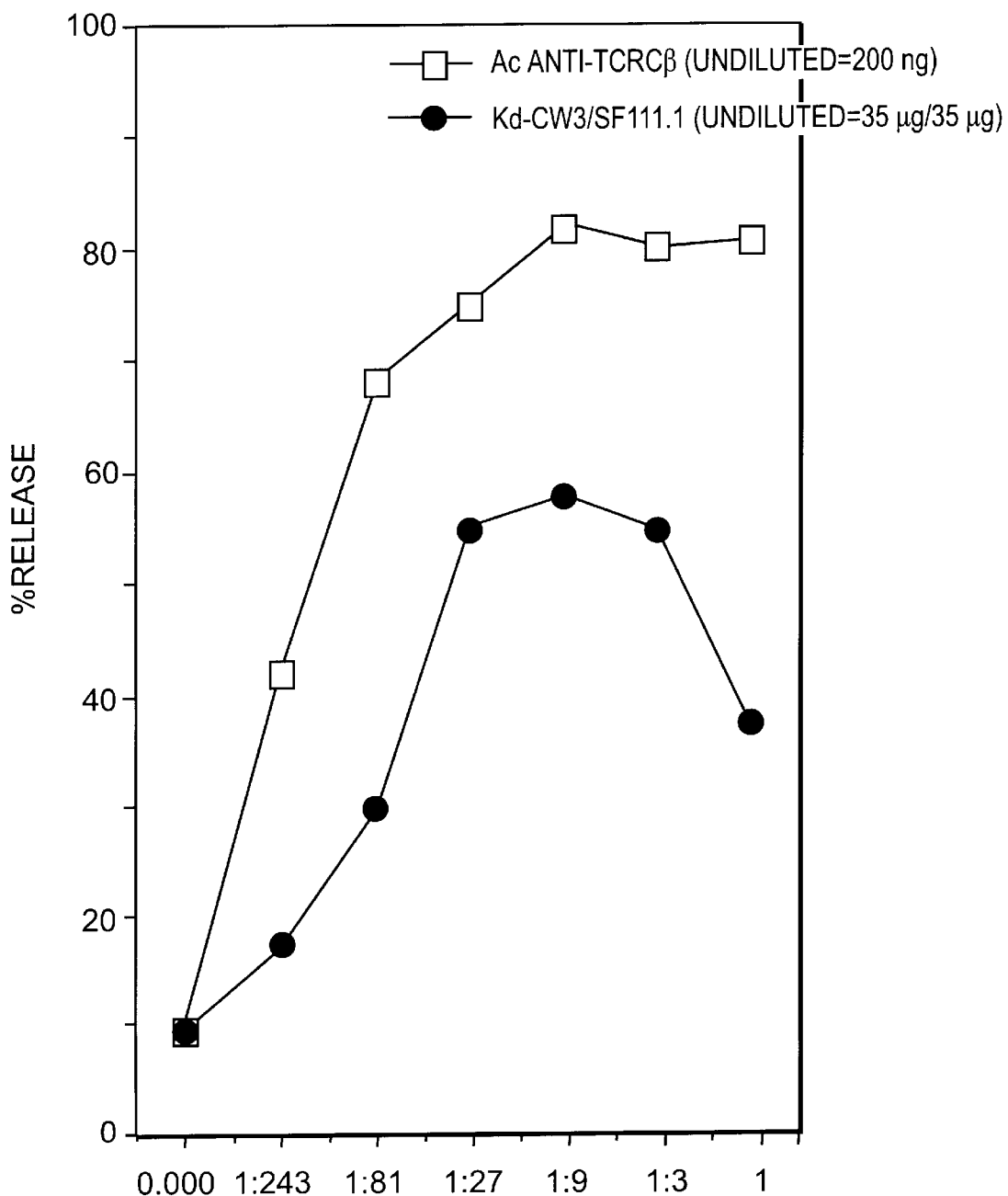

FIG. 14 is a graph which shows the release of serotonin from RBL-2H3 transfectant cells expressing the modified TCR α-ξ-/βξ which were incubated with altered $K^d$ molecules complexed with the SF1-1.1.1 antibody (anti-$K^d$) and the $CW^3$ peptide or with anti-Cβ antibody.

Figure 15:
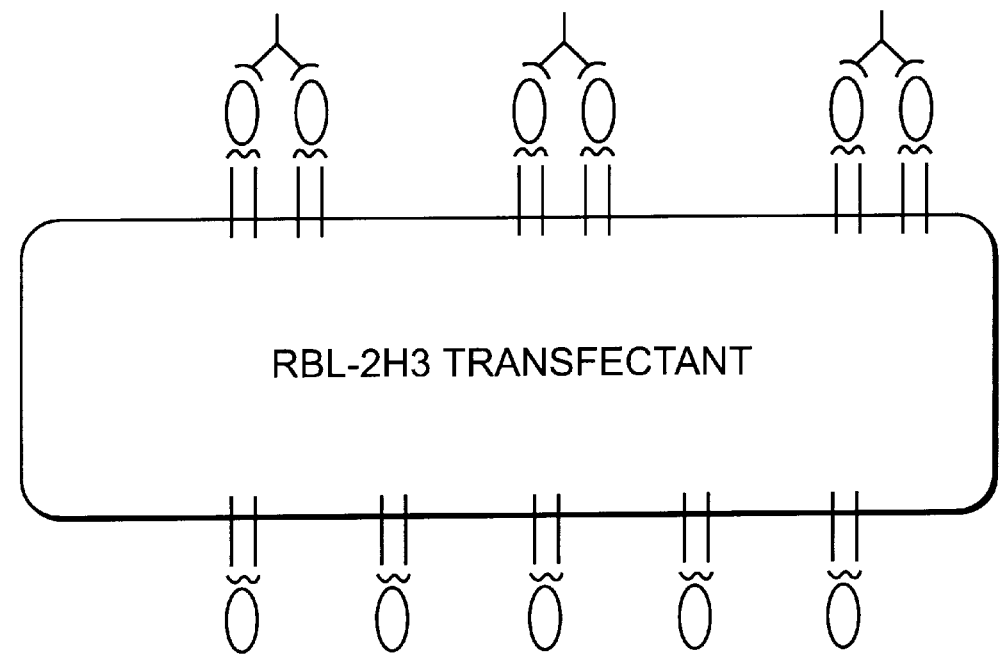

FIG. 15 is a schematic diagram showing the TCR-peptide-MHC complex and the TCR aggregation induced by the anti-$K^d$ antibody.

DETAILED DESCRIPTION OF PREFERRED EMBODIMENT

The invention concerns construction of functional molecules capable of activating the immune system and capable of presenting antigens to the immune system to elicit an antigenic response. More particularly, it concerns the regulation of the immune system response by presenting antigen via an altered MHC determinant so as to cause T-cells to respond to the determinant or the presented antigen. The invention also concerns a method of immunization and therapy for diseases as varied as AIDS, lupus erythematatosus, multiple sclerosis, toxic shock, and snake bite.

1. Major Histocompatibility Complex ("MHC")

All nucleated cells express class I MHC gene products on their surface. Class II gene products are expressed on some cells, such as B cells and macrophages, but not on other cells. This invention provides an altered major histocompatibility complex determinant of a mammal.

The term "major histocompatibility complex" is abbreviated herein as "MHC". The term is used in describing this invention in a generic sense to refer to the set of genes that code for histocompatibility markers in mammals. Exemplary of the mammalian species from which the altered MHC determinants of the invention can be based are the species identified in Table 1.

TABLE 1

| MHC nomenclature of mammalian species | |
|---|---|
| Species | MHC designation |
| Chimpanzee | ChLA |
| Dog | DLA |
| Guinea pig | GPLA |
| Human | HLA |
| Mouse | H-2 |
| Pig | SLA |
| Rabbit | RLA |
| Rat | RT1 |
| Rhesus monkey | RhLA |

Where reference is made herein to the MHC of a particular mammalian species, the MHC designation in TABLE 1 will be employed.

2. Class I And Class II Major Histocompatibility Complex Gene Products

Figure 1:
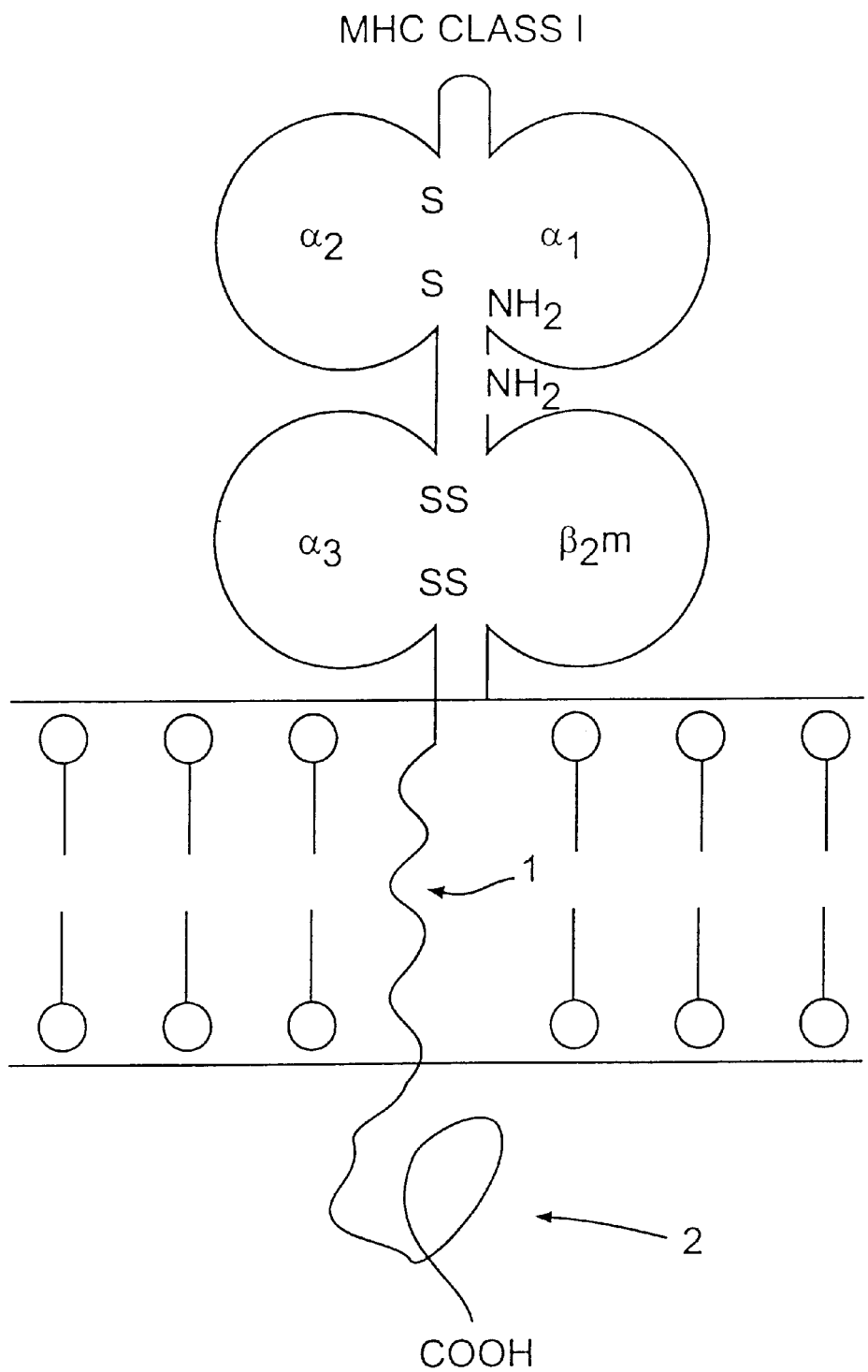
FIG. 1 depicts the orientation of an MHC class I molecule and $\beta_2$-microglobulin in a cell membrane.

Class I MHC gene products are glycoproteins that are noncovalently bound to a peptide termed $\beta_2$-microglobulin, which is abbreviated "$\beta_2$m" or "$\beta_2$M". The class I component is referred to as the heavy chain and the $\beta_2$-microglobulin as the light chain. The orientation of the MHC class I molecule and $\beta_2$-microglobulin in a cell membrane is illustrated in FIG. 1.

Referring to the Figure, the heavy chain structure is organized with three exposed domains, $\alpha_1$, $\alpha_2$, and $\alpha_3$, which extend from the cell surface and are attached to a hydrophobic transmembrane domain 1 and a short cytoplasmic anchor segment 2 within the cell. Two of the outer domains ($\alpha_2$ and $\alpha_3$) have intrachain disulfide bonds (forming loops with considerable homology with Ig).

The light chain ($\beta_2$-microglobulin) shown in the Figure is about the same size as one of the $\alpha$ domains of the heavy chain. Each domain is immunoglobulin-like, consisting of a folded $\beta$ pleated sheet structure held together by a disulfide bond at the ends, giving a plane-like surface. The $\beta_2$ chain folds with the $\alpha_3$ domain of the heavy chain, and the $\alpha_1$ and $\alpha_2$ domains also pair.

The $\beta_2$-microglobulin gene is located on a chromosome different from that containing the MHC class I gene product. Its structure is highly conserved, whereas that of the heavy chains varies extensively from one individual to another because of differences in amino acid sequences of the external domains. The polymorphism of the heavy chain is contributed primarily by the $\alpha_1$ domain and to a lesser degree by the $\alpha_2$ domain.

Figure 2:
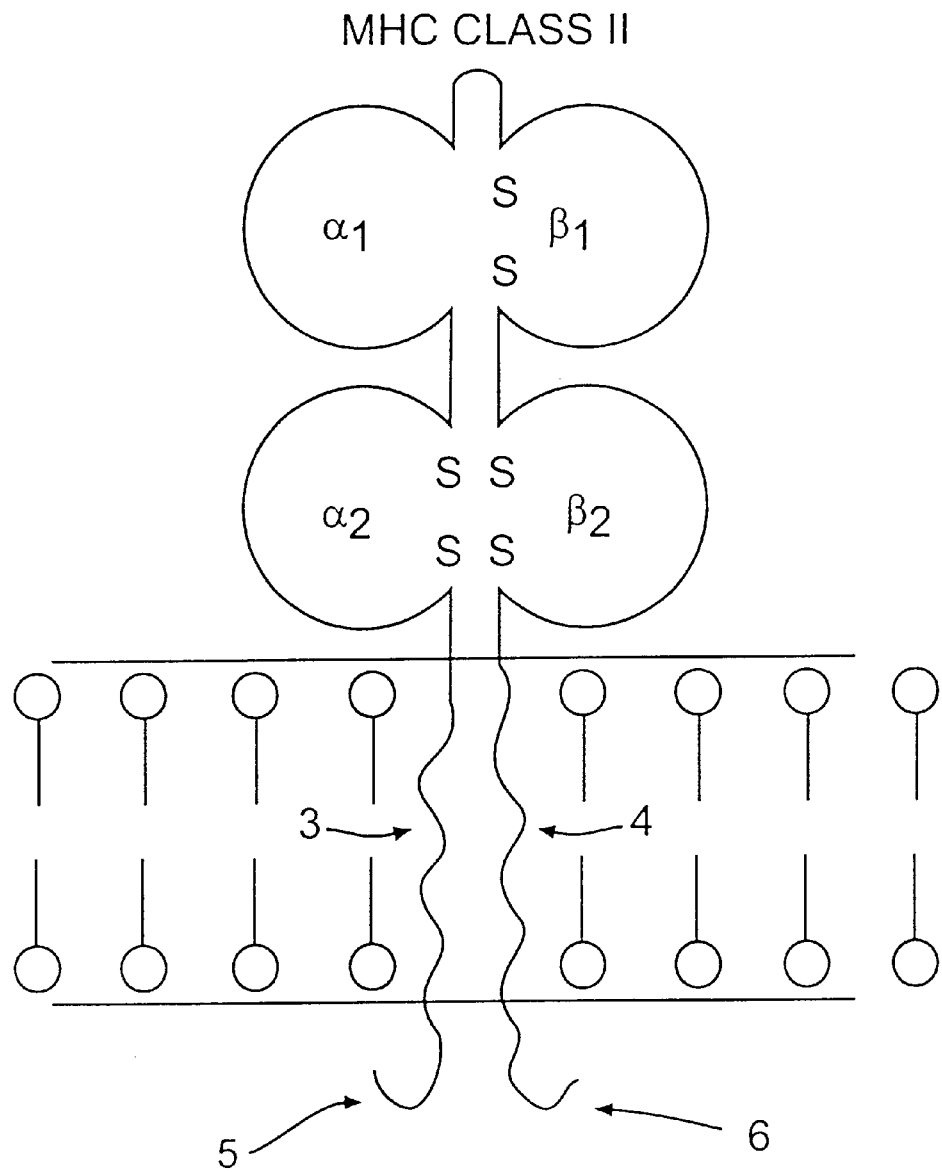
FIG. 2 depicts the orientation of an MHC class II molecule in a cell membrane.

The products of the class II genes are less well characterized. In the mouse, the class II gene product (Ia) consists of two polypeptide chains ($\alpha$ and $\beta$, FIG. 2). The $\alpha$ and $\beta$ chains are divided into two external domains ($\alpha_1$ and $\alpha_2$ or $\beta_1$ and $\beta_2$), transmembrane domains 3 and 4 in FIG. 2, and cytoplasmic domains 5 and 6. Cystein residues that participate in disulfide bridge formation are indicated by S in FIG. 2.

The class I and class II MHC gene products may be glycosylated.

3. Altered Class I And Class II MHC Determinants Of The Invention

This invention involves altered determinants corresponding to products of class I and class II MHC loci. This invention also involves an altered MHC class I or class II determinant with an antigen to form a composition that can be recognized by the immune system of a mammal to initiate an immune or cytolytic response.

Figure 3A:
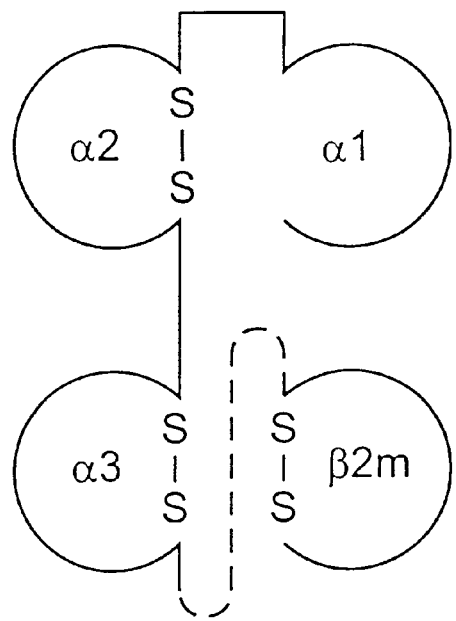
FIG. 3A diagrammatically depicts an altered class I MHC determinant of the invention.

An altered class I MHC determinant substantially free of associated antigen is diagrammatically depicted in FIG. 3A in

TABLE 3

HLA class II loci

| Allele | Allele | Allele | Allele |
| --- | --- | --- | --- |
| Dw1a | DR1 | DQw1 | DPw1 |
| Dw2 | DR2 | DQw2 | DPw2 |
| Dw3 | DR3 | DQw3 | DPw3 |
| Dw4 | DR4 | DPw4 | |
| Dw5 | DR7 | DPw5 | |
| Dw8 | DRw8 | DPw6 | |
| Dw9 | DRw9 | | |
| Dw10 | DRw10 | | |
| Dw11 | DRw11 | | |
| Dw12 | DRw12 | | |
| Dw13 | DRw13 | | |
| Dw14 | DRw14 | | |
| Dw17 | | | |
| Dw18 | | | |
| Dw19 | | | |

"w" designates workshop specificity not yet given accepted status according to WHO nomenclature rules.

The polypeptide employed in this invention can be based on an MHC determinant other than human species. Thus, for example, the polypeptide can be encoded by any of the genetic loci described in Table 4, which identifies MHC loci of the mouse.

TABLE 4

H-2 MHC loci

| Class | I | II II II | II | I | I |
| --- | --- | --- | --- | --- | --- |
| Products | K | Aβ Aα Eβ | Eα | D | L |

It will be understood that the present invention is intended to encompass the altered MHC class I and class II determinants of the invention in the form in which they are prepared in situ or in purified form. In addition, the invention encompasses the altered determinants whether or not fully glycosylated and whether obtained using the techniques described herein or other methods. In a preferred embodiment of this invention, the altered MHC class I and class II determinants are totally free or substantially free of one or more of the following components: mammalian tissue and mammalian tissue components, nucleic acids, extraneous proteins and lipids, and adventitious microorganisms, such as bacteria and viruses. It will also be understood that the invention encompasses equivalent determinants having substantially the same biological and immunogenic properties. Thus, this invention is intended to cover variants of MHC determinants.

Depending upon the use to be made of the altered MHC class I and class II determinants, it may be desirable to label them. Examples of suitable labels are radioactive labels, enzymatic labels, fluorescent labels, chemiluminescent labels, and chromophores. The methods for labeling the altered determinants of the invention do not differ in essence from those widely used for labeling immunoglobulin. The need to label may be avoided using labeled antibody to the altered determinants or anti-immunoglobulin to the antibodies to the altered determinants as an indirect marker.

5. Joining The Polypeptide Domains Of the Altered MHC Determinant

The domains of the altered MHC determinants correspond to domains encoded by naturally occurring MHC loci and variants thereof that encode MHC products capable of effecting a cytotoxic response by appropriate T cells or inducing an immune response by the lymphocyte. The altered MHC class I and class II determinants of the invention differ from naturally occurring mammalian MHC gene products in that domains of the gene products are covalently linked, such as by means of a spacer. For example, in class I NHC gene products in nature, the class I heavy chain is always non-covalently associated with $\beta_2$-microglobulin. In contrast, the altered class I determinant of the invention comprises the class I heavy chain covalently linked to the $\beta_2$m domain. Similarly, the altered MHC class II determinant of the invention is comprised of a polypeptide chain in which the $\beta_2$-$\alpha_2$-$\alpha_1$-$\beta_1$ domains are covalently linked. These domains are never linked in this way in nature. The altered MHC class I and class II determinants are the same as the corresponding MHC gene products in nature in other respects.

The altered MHC determinants of the invention can be obtained from DNA constructs encoding the MHC domains such that there is readthrough translation. For example, in the case of class I MHC determinants, the DNA construct contains a DNA sequence encoding the $\alpha_1$, $\alpha_2$, and $\alpha_3$ domains linked to a DNA sequence encoding the $\beta_2$m domain so that there is readthrough translation from the 5' end of the DNA encoding the $\alpha_1$ domain to the 3' end of the DNA sequence encoding the $\beta_2$m domain. Similarly, the altered class II MHC determinants of the invention can be obtained from DNA constructs in which there can be readthrough translation of a DNA sequence encoding the $\beta_2$-$\alpha_2$-$\alpha_1$-$\beta_1$ domains.

It was surprisingly discovered that despite the covalent linkage of the MHC domains, the resulting altered MHC class I and class II determinants of the invention mimic the unaltered MHC class I and class II gene products that occur in nature.

In one embodiment of this invention, the MHC domains are covalently linked by a spacer, which is a nucleotide sequence encoding a polypeptide that functions as a hinge in the altered determinant. The spacer allows efficient folding or refolding of the domains with respect to each other such that the altered determinant has the ability to bind antigen or to stimulate the immune system.

The nucleotide sequence of the spacer and the corresponding amino acid sequence have not been found to be critical to the successful practice of this invention. Similarly, the size of the spacer has not been found to be critical. The spacer will generally be of a size to encode a polypeptide of about 2 to about 30 amino acids, and preferably about 5 to about 15 amino acids. Particularly preferred spacers encode polypeptides having about 10 to about 15 amino acids.

A typical spacer for use in a DNA construct encoding an altered H-2 determinant of the invention comprises all or part of the following nucleotide sequence:

(SEQ ID NO:15) 5' GATCGGATCCGGAGGCGGTG-GATCCGGTGGCGGCGGTTC 3'

(SEQ ID NO:16) 3' CCTAGGCCTCCGCCACCTAG-GCCACCGCCGCCAAGCTAG 5'

As another example, all or part of the following nucleotide sequence can be employed to form a spacer of up to 15 amino acids for an altered HLA-A2 determinant of the invention:

```
(SEQ ID NO:17) 5" GGT GGC GGT GGA TCA GGC GGT GGT
                  CCA CCG CCA CCT AGT CCG CCA CCA
                  Gly Gly Gly Gly Ser Gly Gly Gly
(SEQ ID NO:18)    GGG TCG GGT GGC GGC GGA TCC 3'
                  CCC AGC CCA CCG CCG CCT AGG
                  Gly Ser Gly Gly Gly Gly Ser
```

Figure 3B:
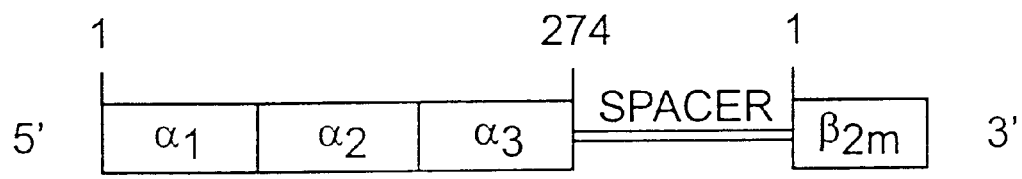
FIG. 3B is a block diagram showing the altered class I MHC determinant of the invention and a spacer covalently linking the MHC gene produce to $\beta_2$-microglobulin.
Figure 4A:
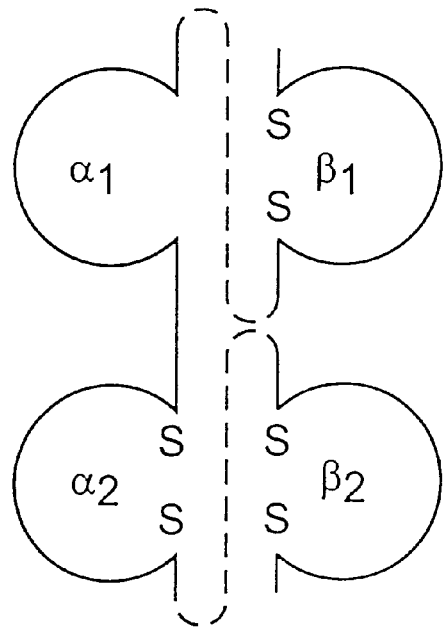
FIG. 4A depicts an altered class II MHC determinant of the invention.
Figure 4B:
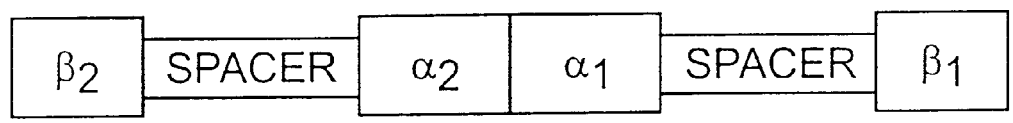
FIG. 4B is a block diagram showing the domains of the altered class II MHC determinant of the invention linked by spacers.

This sequence can be inserted after the nucleotides encoding amino acid 274 of HLA-A2 and before the nucleotides encoding amino acid 1 of human $\beta_2$-microglobulin resulting in the construction depicted in block diagram form in FIG. 3B.

It will be understood that this invention contemplates the use of the altered MHC determinants in non-cross-linked or cross-linked form. It will also be understood that the altered MHC determinant can be loaded with antigen without unfolding the antigen binding domain. Nevertheless, the invention contemplates unfolding the domain, for example in 7M urea, and dialysis.

6. Antigens Presented In Association With The Altered MHC Determinant

T cells can recognize synthetic peptides loaded on MHC class I and class II molecules. This phenomenon is called MHC restriction. The altered MHC class I determinants and class II determinants of this invention are capable of MHC restriction by association with antigens that are recognizable by T cell receptors of mammalian cells. Crystallography of human MHC class I molecules, HLA-A2 and Aw68, revealed a groove made up by the $\alpha_1$ and $\alpha_2$ domains of heavy chains. This groove is believed to be the binding site for antigens. The altered MHC class I determinants of the invention include a binding site of this type for antigens.

More particularly, this invention makes it possible to present antigens to the mammalian immune system and to elicit an immune response in vivo or in vitro. The antigen presented in association with the altered MHC determinant of this invention is generally a peptide. The antigens recognized by MHC class I and class II restricted T cells can be mimicked by artificial peptides. The peptide can also be a naturally occurring peptide. Thus, the peptide can be isolated from a source in which it occurs in nature or the peptide can be chemically synthesized.

When the antigen associated with the altered MHC determinant of this invention is a peptide, the peptide will typically contain about 5 to about 20 amino acid residues, preferably 8, 9 or 10 amino acid residues, when altered class I MHC molecules are used. Longer peptides can be employed with the altered MHC class II determinants of the invention. Octamers, nonomers, and decamers are particularly preferred peptides.

The naturally occurring peptides that normally bind to MHC gene products can be modified at one or more positions by other amino acids. In this event, it will be understood that the modified peptide will not necessarily have the same binding characteristics as the native or unmodified peptide; that is, a distinct allele-specific peptide motif capable of being presented by each MHC determinant may be observed. In any event, the peptide motifs typically contain two anchor positions occupied by a fixed amino acid residue or by one of a few residues with closely related side chains. These anchor positions are not in the same place in the different motifs. In general, the structure of the peptide should match the peptide-binding cleft of the altered MHC determinant. Thus, the allele-specific pockets in the altered MHC determinants of this invention and the side chains of the allele-specific anchor residues should preferably have complementary structures. Following are guidelines for selecting peptide/MHC combinations.

The physical association of antigenic peptides and altered MHC class I and class II determinants of the invention can be monitored using a direct peptide binding assay (PBA) in solid phase or an inhibition peptide binding assay (IPBA) in which the competing peptide is present in a soluble phase. Other tests measuring changes in fluorescence of an appropriately labeled peptide in soluble form when binding to a soluble MHC, or altered MHC molecule, are also available. The ability of different peptides to inhibit the lytic activity of human antiviral cytolytic T cells toward cells incubated with the corresponding target peptide can also be examined as a measure of the effectiveness of antigen binding and presentation.

In general: (a) Binding of a given human T cell-recognized peptide to several HLA class I and class II molecules occurs occasionally. Nevertheless, preferential binding of peptides to their respective restriction molecules is also observed. (b) Binding of HLA molecules to peptides recognized by murine T cells occurs less frequently, but such mechanisms are contemplated by this invention. (c) There exist HIV-1 peptides containing agretopic residues which allow their binding to HLA molecules and are particularly interesting in the scope of the invention. (d) The kinetics of HLA/peptide association depend on the peptide tested and are faster than or similar to those for Ia molecules. (e) Peptide/HLA molecule binding is frequently dependent on length, number of positive charges, and presence of hydrophobic residues in the peptide. (f) A correlation may be observed between a peptide inhibitory effect in the IPBA and its blocking effect in the cytolytic test.

Examples of typical peptides that can be combined with the altered MHC determinants of this invention are given in Table 6.

Table 6

Peptides for Binding to Altered MHC Deteriminants

| Peptide | Sequence | Restricting Element |
| --- | --- | --- |
| Influenza A virus | | |
| Matrix | | |
| M.57–68 | KGILGFVFTLTV | HLA-A2 |
| M.Y⁺57–68 | YKGILGFVFTLTV | HLA-A2 |
| NUCLEOPROTEIN | | |
| N.147–158R⁻ | TYQRTRALVTG | H-2 $K^D$ |
| N.335–349Y⁺ | SAAFEDLRVLSFIRGY | HLA-B37 |
| Haemagglutinin | | |
| H.130–142 | HNTNGVTAACSHE | $Ia^d$ |
| H.305–329 | CPKYVKQNTLKLATGMRNVPEKQTR | HLA-DR |
| Lysozyme; Lys.46–61 | NTDGSTDYGILQINSR | $Ia^k$ |
| λ repressor: λR.12–26 | LEDARRLKAIYEKKK | $Ia^d$ |
| HLA-A2: A2.170–185 | RYLENGKETLQRTDAP | H-2 $K^d$ |

Table 6-continued

Peptides for Binding to Altered MHC Deteriminants

| Peptide | | Sequence | Restricting Element |
|---|---|---|---|
| HIV 1 | | | |
| GAG. | 51–65 | LETSEGCRQILGQLQ | |
| | 205–219 | ETINEEAAEWDRVHP | — |
| | 219–233 | HAGPIAPGQMREPRG | — |
| | 265–279 | KRWIILGLNKIVRMY | HLA-B27 |
| | 378–391 | MQRGNFRNQRKIVK | — |
| | 418–433 | KEGHQMKDCTERQANF | HLA-A2 |
| Env. | 105–117 | HEDIISLWDQSLK | Ia* |
| | 312–327 | IRIQRGPGRAFVTIGK | H-2 $D^d$ |
| | 428–445 | FINMWQEVGKAMYAPPIS | Ia* |
| | 474–489 | RPGGGDMRDNWRSELY | — |
| | 510–521 | VVQREKRAVGIG | — |
| | 584–604 | RILAVERYLKDQQLLGIWGCS | HLA,Cl II* |
| | 827–843 | YVAEGTDRVIEVVQGACR | — |
| | 846–860 | RHIPRRIRQGLERIL | — |
| Nef. | 66–80 | VGFPVTPQVPLRPMT | — |
| | 79–94 | MTYKAAVDLSHFLKEK | — |
| | 113–128 | WIYHTQGYFPDWQNYT | HLA-B17.37 |
| | 132–147 | GVRYPLTFGWCYKLVP | HLA-B18 |
| | 137–145 | LTFGWCYKL | — |
| | 160–174 | ENTSLLHPVSLHGMD | — |
| Vif. | 1–15 | MENRWQVMIVWQVDR | — |
| | 25–40 | VKHHMYVSGKARGWFY | — |
| | 46–60 | SPHPRISSEVHIPLG | — |
| | 60–72 | GDARLVITTYWGL | — |
| | 71–85 | GLHTGERDWHLGQGV | — |
| Ref. | 1–16 | MAGRSGDSDEDLLKAV | — |
| | 18–30 | LIKFLYQSNPPPN | — |
| | 37–50 | ARRNRRRRWRERQR | — |
| Vpr. | 1–14 | MEQAPEDQGPQREP | — |
| | 55–68 | AGVAEIIRILQQLL | — |
| | 68–80 | LFIHFRIGCRHSR | — |

*Not precisely identified restricting element.

Examples of other peptide epitopes that can be associated with the altered MHC determinants of this invention are shown in Table 7.

TABLE 7

Additional Peptides for Binding to Altered MHC Determinants

| Sequence | Protein source |
|---|---|
| T Y Q R T R A L V | Influenza PR8 NP 147–154 |
| S Y F P E I T H I | Self-peptide of P815 |
| I Y A T V A G S L | Influenza JAP HA 523–549 |
| V Y Q I L A I Y A | Influenza JAP HA 523–549 |
| - - - N V G T Y V | Influenza PR8 HA 518–528 |
| - - - E N G K E T | HLA-A24 170–18233 |
| R Y L K N G K E T | HLA-Cw3 170–186 |
| K Y Q A V T T T L | P815 tumour antigen |
| S Y I P S A E K I | Plasmodium berghei CSP 249–260 |
| S Y V P S A E Q I | Plasmodium yoelii CSP 276–288 |
| Known epitopes, aligned | |
| A S N E N M E T M | Influenza NP366–374 |
| S G P S N T P P E I§ | Adenovirus E1A |
| S G V E N P G G Y C L§ | Lymphocyte choriomeningitis virus GP 272–293 |
| S A I N N Y . . . | Simian virus 40 T 192–211 |
| Known epitopes, aligned | |
| R G Y V Y Q G L | Vesicular stomatitis virus NP 52–59 |
| S I I N F E K L | Ovalbumin 258–276§ |
| A P G N Y P A L | Sendai Virus NP 321–332 |
| Known epitopes, aligned | |
| I L K E P V H G V | HIV reverse transcriptase 461–485 |
| F L Q S R P E P T | HIV Gag protein 446–460§ |
| A M Q M L K E . . | HIV Gag protein 193–203§ |
| Q M K D C T E R Q | HIV Gag protein 418–443§ |

The antigens described in Tables 6 and 7 are merely representative of antigens that can be presented to cell receptors in association with the altered MHC determinants of this invention. Other antigens that form complexes with the determinants can also be employed. Using both the direct peptide binding assay (PBA) and the inhibition of peptide binding assay (IPBA), the physical interactions between HLA molecules and peptides can be analyzed. More particularly, the assays can be carried out as follows.

Direct Peptide Binding Assay. Wells of microtiter plates are pretreated with 100 μl 2.5% glutaraldehyde in distilled water for 2 h at 20° C., washed with distilled water, and coated for 16 h at 4° C. with 100 μl of peptide diluted at 5 μg/ml either in carbonate-bicarbonate buffer, pH 9.6, or in PBS, pH 7.4 or pH 5.0. Remaining free sites are blocked by incubation for 2 h at 20° C. with BSA diluted 1% in PBS containing 0.05% Tween 20 (Tw) and 0.02% sodium azoture. After washing, purified $^{125}$I-HLA molecules (100 μl containing $1.5 \times 10^5$ cpm, $10^{-9}$ M) diluted in PBS containing 1% BSA, 0.05% Tw, 0.02% sodium azoture, 1 mM PMSF, and 10 μg/ml trypsin inhibitor are added and incubated for 20 h at 20° C. After extensive washing, the radioactivity of each well is counted.

Inhibition Peptide Binding Assay. Concentrations of 0.1–100 μM of competitor peptides are incubated in tubes for 0–3 h at 20° C. with $^{125}$I-HLA ($10^{-9}$ M) diluted in PBS-BSA-Tw containing the protease inhibitors as mentioned above. Then the mixture is added to microtiter plate wells coated with a peptide that shows significant binding to HLA molecules in the direct test and incubated 20 h at 20° C. After extensive washing, the radioactivity in each well is counted and the percent of inhibition is calculated.

Competition between Peptides in a Lytic Assay. Human antipeptide CTL is generated (37). Briefly, $6–8 \times 10^7$ PBMC are stimulated with 100 μg of a synthetic peptide in 10 ml culture medium (RPMI 1640 supplemented with 100 μg/ml penicillin, 100 μg/ml streptomycin, 2 mM L-glutamin, 2 mM nonessential amino acids, 1 mM sodium pyruvate, 10 mM Hepes, and 10% pooled heat-inactivated human AB serum). After a 7-d incubation, a secondary in vitro stimulation is performed by mixing $5–7 \times 10^6$ effector cells with $2–3 \times 10^7$ irradiated (4,000 rad) autologous PBMC in 10 ml culture medium containing 50–100 μg of peptide.

In most cases, T cell epitopes are recognized in association with only a few, if not a single, MHC restriction elements. In contrast, some peptides can be recognized in association with several H-2 or HLA molecules. Furthermore, a single peptide can be recognized by both MHC class I and class II restricted T cells. Since class I and class II molecules have a similar predicted tertiary structure, including a single antigen binding site, interactions between peptides and these two types of molecules are also contemplated by this invention. Moreover, it will be understood that this invention contemplates the binding of antigens normally associated with the MHC of one species, such as H-2, to the altered MHC determinant of another species, such as HLA.

The formation of compositions comprising antigens bound to the altered MHC determinants of the invention can be based on peptides known to be antigenically involved in diseases such as AIDS (gag, nef, vif, ret, vpr, or env proteins or peptides), multiple sclerosis (myelin basic protein), toxic shock (bacteria), or snake venom (antigenic region for particular snake venom, alkaloid based and proteinaceous based; current snake bite therapy is based on administration of antibodies to the particular venom). These compositions can be formulated so as to allow the target recognition potential of an immune system cell to be specifically redirected to the antigen in presentation with the altered MHC determinant. It will be understood that libraries comprised of different altered MHC determinants of the invention and associated antigens can be prepared. It is thus possible to formulate compositions comprising two or more of the members of the library in any combination or amount, such as for simultaneously or sequentially targeting different receptors.

The extent of loading of the altered MHC determinant with peptide varies. The altered MHC determinant is typically employed in an amount of about 10 to about 1000 μg/ml and the peptide is employed in an amount of about 10 to about 1000 μg/ml.

While this invention has been described with reference to the use of peptides for binding altered MHC determinants, it will be understood that other antigenic materials can be employed. For example, peptides combined with haptens in general can be employed. Peptides can be combined with metals, such as nickel. Peptides can also be combined with carbohydrates. Certain chemicals, such as p-benzoyl arsonate, also bind directly in the groove of MHC materials. Suitable antigens are reviewed by P. Kourilsky and J. M. Claverie in "Advances in Immunology" (1989).

Similarly, the altered MHC determinants of the invention can be loaded with conventional immunotoxins and directed to a T cell associated with autoimmune disease for the purpose of disabling the T cell. Diptheria toxin, or subunits thereof, and Pseudomonas A toxin are examples of suitable immunotoxins.

7. Binding To Lymphocyte Cell Receptors

The altered MHC class I and class II determinants of the invention and compositions comprising antigens bound to the altered determinants are recognizable by receptors on T lymphocytes.

More particularly, the antigen and MHC recognition structure of T cells is referred to herein as the T cell receptor. The T cell receptor involved in antigen and MHC recognition is characterized in Table 8. Variable regions of the α- and β-chains form the antigen binding site and also determine MHC specificity. In the presence of antigen and MHC, the T cell is activated. This results in phosphorylation of at least two subunits of the receptor complex, the δ- and ϵ-chains.

TABLE 8

Surface Structures Involved in Antigen Recognition by Human T Lymphocytes

| Chains | Molecular Weight Nonreduced | Reduced | Function |
|---|---|---|---|
| A. T Cell receptor complex α and β | 90,000 | 41,000–43,000 (two chains) | Dual recognition of antigen and MHC |
| "$T_3$ complex" - δ | 23,000 | 23,000 | Phosphorylated during cell activation |
| γ | 20,000–23,000 | 20,000–23,000 | Unknown |
| ϵ | 20,000 | 20,000 | Phosphorylated during cell activation |
| ζ | 32,000 | 16(two chains) | Unknown |
| B. $T_4$(CD4) | 62,000 | 62,000 | MHC class II recognition |
| C. $T_8$(CD8) | 76,000 | 31,000–33,000 | MHC class I recognition |

Two other chains on the T cell surface, $T_4$ (CD4) and $T_8$ (CD8), are associated with the recognition of the altered class I or class II MHC determinants of the invention, without interacting with antigen. These molecules may normally bind non polymorphic (constant) determinants on class I or class II gene products of the antigen presenting cell. These molecules may also be associated with the T cell receptor.

A summary of the relationship between MHC class I and class II molecules and the type of immune reactive T cells is given in Table 9.

TABLE 9

Restrictions On Lymphoid Cell Activation

| Function | Phenotype | Restriction |
|---|---|---|
| T helper | $CD4^+CD8^-$ | Class II MHC + Antigen |
| DTH | $CD4^+CD8^-$ | Class II MHC + Antigen |

TABLE 9-continued Restrictions On Lymphoid Cell Activation

| Function | Phenotype | Restriction |
|---|---|---|
| CTL | $CD4^-CD8^+$or $CD4^+CD8^-$ | Class I or II MHC + Antigen |
| Suppressor | $CD4^-CD8^+$ | Class I MHC |

T helper cell activation and delayed hypersensitivity effector (DTH) cells are antigen and class II MHC restricted; CTL activities are antigen and class I or class II MHC restricted. Suppression can be class I restricted or unrestricted. Surface phenotype (CD4 or CD8) correlates mainly with MHC recognition of class II ($CD4^+$) or class I ($CD8^+$).

Considering the important regulatory role of class II restricted inducer cells (all of which are $CD4^+$), it is not surprising that a virus such as the AIDS-related virus, which infects T cells through the CD4 marker and thus selectively depletes the CD4 population, can cause the severe immune suppression and other abnormalities of lymphocyte growth seen in AIDS patients. This invention should make it possible to inhibit infection of cells by blocking the susceptible cell surface marker with either the altered MHC class I or class II determinant or by the composition comprising antigen bound to the altered determinant. This invention should also make it possible to mimic antigen binding to the T cell receptor α- and β-chains or to the δ-chains. By cross-linking receptors with the altered determinant of the invention, T cell activation is facilitated. This invention thus makes it possible to stimulate or enhance the function of the immune system.

8. Methods Of Preparing Altered MHC Class I And Class II Determinants

The altered MHC class I and class II determinants of the invention can be prepared according to well known recombinant DNA techniques. More particularly, nucleic acid sequences encoding the domains of class I and class II MHC gene products and $\beta_2$m, and spacers where appropriate, are employed in this invention. A nucleic acid fragment of interest can be ligated to a cloning vehicle. The nucleic acid can be obtained from any source, for example, from plasmids, from cloned DNA or RNA, or from natural DNA or RNA from any source. DNA or RNA can be extracted from a biological material, such as biological fluids or tissue, by a variety of techniques including those described by Maniatis et al., *Molecular Cloning: A Laboratory Manual,* Cold Spring Harbor Laboratory, New York (1982). The nucleic acid will generally be obtained from a higher organism, such as an animal. The nucleic acid sequence can also be chemically synthesized using conventional techniques.

It is not necessary that the nucleic acid fragment to be ligated be present in a pure form. The nucleic acid to be ligated can contain more than one specific nucleic acid sequence, which can be the same or different. The specific nucleic acid fragment to be ligated can be a fraction of a larger molecule or the fragment can constitute an entire gene or assembly of genes encoding the domains of interest. The DNA can be a single-stranded or double-stranded form. If the fragment is in single-stranded form, it can be converted to double-stranded form using DNA polymerase according to conventional techniques.

The nucleic acid fragment to be ligated can have cohesive ends compatible with any combination of sites in a cloning vehicle. Alternatively, the nucleic acid fragment can have one or more blunt ends that can be ligated to corresponding blunt ends in the cloning sites of the vehicle. The nucleic acid fragment to be ligated can be further processed, if desired, by successive exonuclease deletion, such as with the enzyme Bal 31. In the event that the nucleic acid fragment to be ligated does not contain a desired combination of cohesive ends, the fragment can be modified by adding a linker, an adaptor, or homopolymer tailing.

If it is difficult to determine which fragment in a complicated mixture of nucleic acid sequences is desired for ligation, or if it is desired to ligate more than a single nucleic acid fragment, mixtures of nucleic acid fragments can be employed. This procedure can be utilized to generate a small library of clones that contain all compatible fragments in the original nucleic acid mixture.

The cloning vehicle employed in practicing the invention can be any double-stranded DNA molecule capable of transporting the nucleic acid fragment to be ligated into the host cell and capable of replicating within the cell. More particularly, the cloning vehicle must contain at least one DNA sequence that can act as the origin of replication in a host cell. In addition, the cloning vehicle must contain two or more sites for insertion of the nucleic acid sequence to be ligated. These sites will ordinarily correspond to restriction enzyme sites at which cohesive ends can be formed, and which are complementary to the cohesive ends on the nucleic acid fragment to be ligated to the vehicle. In general, this invention can be carried out with plasmid, bacteriophage, or cosmid cloning vehicles having these characteristics.

It is preferred that the plasmid carry one or more genes responsible for a useful characteristic, such as selectable marker, displayed by the host cell. In one type of strategy, plasmids having genes for resistance to two different drugs are chosen. For example, insertion of the DNA fragment of interest into a gene for an antibiotic inactivates the gene and destroys drug resistance. The second drug resistance gene is not affected when bacterial cells are transformed with the recombinants, and colonies containing the gene of interest can be selected by resistance to the second drug and susceptibility to the first drug. Preferred antibiotic markers are genes imparting chloramphenicol, ampicillin, or tetracycline resistance to the host cell.

When a plasmid is employed, the plasmid can be derived from bacteria or some other organism or the plasmid can be synthetically prepared. The plasmid can replicate independently of the host cell chromosome or an integrative plasmid (episome) can be employed. The plasmid can make use of the DNA replicative enzymes of the host cell in order to replicate or the plasmid can carry genes that code for the enzymes required for plasmid replication. A number of different plasmids can be employed in practicing this invention. Typical of the plasmids that can be utilized are pBR322, pBR325, Co1E1, RP4, and the 2 μm circle that occurs in many strains of the yeast *Saccharomyces cerevisiae.* The cloning vehicle can also be a bacteriophage. It will be understood that this invention can be practiced with phage vectors that proliferate by a lytic cycle or by lysogenic infection.

Cloning can be carried in procaryotic or eucaryotic cells. The host for replicating the cloning vehicle will of course be one that is compatible with the vehicle and in which the vehicle can replicate. Cloning can be carried out in bacterial or yeast cells, although cells of fungal, animal, and plant origin can also be employed. The preferred host cells for conducting cloning work are bacterial cells, such as *E. coli,* as well as species of Streptomyces, Bacillus, and Pseudomonas. The use of *E. coli* cells is particularly preferred because most cloning vehicles, such as bacterial plasmids and bacteriophages, replicate in these cells. Yeast cells can also be employed for cloning work. Also preferred are strains of *Saccharomyces cerevisiae.* Animal cells, such as COS monkey cells, are preferred where post-translational processing of the altered MHC determinant is desired. For example, the altered MHC class I and class II determinants of the invention can be prepared in glycosylated form in COS cells. This invention thus contemplates the preparation and use of the altered determinants of the invention in glycosylated or non-glycosylated form.

Expression control sequences can be included in the vector of this invention. These include the operator, promoter and ribosome binding and interaction sequences (including sequences such as the Shine-Dalgarno sequences), the lactose operon of *E. coli* ("the lac system"), the corresponding sequences of the tryptophan synthetase system of *E. coli* ("the trp system"), the major operator and promoter regions of phage λ ($O_L P_L$ and $O_R P_R'$), and the control region of the phage fd coat protein. DNA fragments containing these sequences can be excised by cleavage with restriction enzymes from the DNA isolated from transducing phages that carry the lac or trp operons, or from the DNA of phage λ or fd. These fragments can then be manipulated in order to obtain a limited population of molecules such that the essential controlling sequences can be joined very close to, or in juxtaposition with, the initiation codon of the coding sequence for the desired gene product. The product is then inserted into a cloning vehicle for transformation of the appropriate hosts and the level of production measured. Cells giving the most efficient expression can be selected.

To shorten the distance between the particular expression control sequence and the initiation codon of the chosen gene fragment, the particular fragment may be treated lightly with a combination of nucleases acting specifically at or near its terminus or used in exonuclease and polymerase-linked repair reactions to remove some or all of those nucleotides of the fragment preceding the fragment's start codon. Alternatively, a fragment can be similarly shortened with exonuclease treatment or polymerase-linked repair reactions and then cleaved to produce one fragment to permit fusion to another fragment before attachment to the expression control sequence.

The nucleotide sequences encoding domains of class I and class II mammalian gene products are known in the art and can be employed in practicing this invention. For example, following are primary structural data for $\beta_2$m molecules from several different species that can be employed in practicing this invention.

```
SEQ ID NO:
                                 10        20        30        40        50
                                 |         |         |         |         |
     59         Mouse β2m  IQKTPQIQVYSRHPPENGKPNILNCYVTQFHPPHIEIQMLKNGKKIPKVE
     60           Rat β2m  --------------------F-----S-----Q---EL--------NI-
     61    Guinea Pig β2m  VHLA-RV-------A----Q-FI----SG----Q--VEL-------DN--
     62        Rabbit β2m  V-RA-NV-------A------F-----SG----Q-D-EL---V---EN--
     63         Human β2m  --R--K---------A----S-F-----SG---SD-VDL--D-ER-E---
     64        Bovine β2m  --RP-K-----------Y-----YG----Q---DL----E--KS--

60        70        80        90       99
                                           |         |         |         |        |
                Mouse β2m  MSDMSFSKDWSFYILAHTEFTPTETDTYACRVKH SMAEPKTVYWDRDM
                  Rat β2m  ---L---------------------V-------VTLK-----------
           Guinea Pig β2m  ---L------T--L-V-AA---NDS-E-S---S-ITLS---I-K--PNK
               Rabbit β2m  Q--L--N------L-V------NNKNE-S-----VTLK--M--K----Y
                Human β2m  H--L---------L-YY-------K-E-----N-VTLSQ--I-K-----
               Bovine β2m  Q--L---------L-S-A----DSK-E-S-----VTLEQ-RI------L
```

The straight lines indicate homology to the sequence listed at the top. The single letter code for amino acids is used where A is Ala; C, Cys; D, Asp; E, Glu; F, Phe; G, Gly; H, His; I, Ile; K, Lys; L, Leu; M. Met; N, Asn; P, Pro; Q, Gln; R, Arg; S, Ser; T, Thr; V, Val; W, Trp; Y, Tyr. Position 85 of mouse $\beta_2$m is Ala for C57BL/6 mice and Asp for BALB/c. Source: Paul, *Fundamental Immunology*, 2nd Ed., Raven Press, N.Y. (1989), page 500.

Exemplary of other sequences that can be employed in this invention are those in the following compilation of sequences for murine class I molecules encoded within H-2, Q, and TL subregions.

| SEQ ID NO: | | 1   5    10   15   20   25   30   35   40   45   50   55   60   65   70   75   80   85   90 |
|---|---|---|
| | | EXON 2 |
| 65 | H-2K$^b$ | GPHSLRYFVTAVSRPGLGEPRYMEVGYVDDTEFVRFDSDAENPRYEPRARWMEQEGPEYWERETQKAKGNEQSFVDLRTLLGYYNGSKG |
| 66 | H-2K$^d$ | ------------------FIA------Q----D---F----P------EQ--R--SD--W---S---AQR----- |
| 67 | H-2K$^k$ | -------H---------K-FIS-----Q-------------------------V-----------I--N--A-R---A--- |
| 68 | H-2K$^q$ | -------H---*-*K--FIS-----Q-------------------VE----------VE--N--I--D------R----A--- |
| 69 | H-2D$^d$ | -S---------------F-------------N--------------------I-----------RR--------A-R---A--- |
| 70 | H-2D$^p$ | ------M--E------K--------------N----------MK-V-----------------Q--N-DH------S-N------ |
| 71 | H-2D$^b$ | ------M--E------IS------NK----------------------P-----------------Q--W---S-N----A-- |
| 72 | H-2L$^d$ | ------M--E------IS------NK----------------Q--P-----------I--I---Q--W---N----A-- |
| 73 | Q-7$^d$(27.1) | -Q----Q--H--------------Q-------M--------------------------M-----H----GS--AQS------ |
| 74 | Q-7$^b$ | -Q----Q--H----WFIS-----Q-------M-------------------------I---H----GS--AQS------ |
| 75 | Q-8$^b$ | -----H--W--V---FII-----Q-------M-------------------------H-E----S--AQR------ |
| 76 | Q-9$^b$ | -Q----Q--H--------WFIS-----Q-------M-------------------------I---H----GS--AQS------ |
| 77 | Q-10$^b$ | -S---M--E-S---FII-----Q-------T--M--P-----------R-------H-S---H--ES |
| 78 | PH-2$^d$-37 | S-------T---------------------M--I-----------------W--RDMGRN--N--------ND |
| 79 | 17.3A | -S----Y--L---AIS--W--IA--L---Q-A---AG-TGT-KLS-P-V-----A---EIVTA-A--F--EN-Q-M-D--L-QN |
| 80 | C25.1 | -S----Y--L---AIS--W--IA--L---Q-------N-SG-TAT-KLS-P-V-----A---EIVTS-A--F--EN-Q-M-D--L-QN |
| 81 and 82 | T1a$^a$-1 | -S----K--Y--L---IAG--L---Q-RC-E-AG-SAT-KL--P-V-----A---EIVTS-A--F--EN-Q-M-D--SL-QN |

| | | 91  95   100  105  110  115  120  125  130  135  140  145  150  155  160  165  170  175  180 |
|---|---|---|
| | | EXON 3 |
| 65 | H-2K$^b$ | GSHTIQVISGCEVGSDGRLLRGYQQYAYDGCDYIALNEDLKTWTAADMAALITKHKWEQAGEAERLRAYLEGTCVEWLRRYLKNGNATLLRT |
| 66 | H-2K$^d$ | ------F-RMF--D---W-----F--R-----------T----RR-------D-YY------E-------EL--E-------- |
| 67 | H-2K$^k$ | ------F-RMY-----W-----E-----------------------D-----------QL---P------ |
| 68 | H-2K$^q$ | ------RMY-----------E-V-----------------------A---R------A----S-H-------- |
| 69 | H-2D$^d$ | -----L-WMA--D-E-----W-F-----------------Q---RR------A---D------E-------- |

-continued

| SEQ ID NO: | | | | | | | | | |
|---|---|---|---|---|---|---|---|---|---|
| 70 | H-2D$^p$ | ------GMR-D----W------E-F-----P--------Q--RR------A--T-----A-------EL------C- |
| 71 | H-2D$^b$ | ----L-QM----DL--W------L-F--E-R--------Q--RR----S-A--HYK----E-------H-------- |
| 72 | H-2L$^d$ | ---T-L-WMY-D----------E-F----R---------Q--RR------A--YY-----E-------H-------- |
| 73 | Q-7$^d$(27.1) | ----L-WMY-DM---------L-F--E-R------V---Q--RR------I--KDQ------MQS-----QL--KE- |
| 74 | Q-7$^b$ | ----L-WMY-DM---------L-F--E-R------V---Q--RR------I--KDQ------MQS-----QL--KE- |
| 75 | Q-8$^b$ | ----L-WMY-D-----E----L-F--E-R----------Q--L-------I--D------A--QS-----QLRKE--C- |
| 76 | Q-9$^b$ | ----L-WMY-DM---------L-F--E-R------V---Q--RR------I--KDQ------M-S-----QL--KE- |
| 77 | Q-10$^b$ | -----WMY-K-----F----L------R----------V--I--RR------A--YY-----AE-----L--EL-KE- |
| 78 | PH-2$^d$-37 | E---L-WMY--D--P------C-E-----Q---S----RS--N-I-SQ-S---S-AVD--HQQ-----Q--P-----H---RL--E---Q-S |
| 79 | 17.3A | ------MY----EFF-S-F-A-E-HG----Q-------E--RS-------YT-LR-T----P-KDS-L---E-RKK-QEC- |
| 80 | C25.1 | ------MY----EFF-S-F-A-E-HG----R-------T--E--RS-----YT-LR-T----P-KDS-L---E-RKK-QEC- |
| 81 and 82 | T1a$^a$-1 | ------MY----$$$-N-F-A-E-HG----R-------E--RS-------YT-LR-T----P-KDS-F---E-RKK-QECA |
| 83 | T1a$^a$-3 | FS$$S-S-F-A-E-HG----R--------V--------E--RS-------YT-LR-T----P-KDS-L---E-RKK-QEC- |

| SEQ ID NO: | | 185 190 195 200 205 210 215 220 225 230 235 240 245 250 255 260 265 270 |
|---|---|---|
| | | EXON 4 |
| 65 cont. | H-2K$^b$ | DSPKAHVTHHSRPEDKVTLRCWALGFYPADITLTWQLNGEELIQDMELVETRPAGDGTFQKWASVVVPLGKEQYTCHVYHQGLPEPLTLRW |
| 66 cont. and 85 | H-2K$^d$ | -------Y-P-SQVD---------------------------D-T--------------A---------N----H-K--- |
| 67 cont. | H-2K$^k$ | ----------------R------------------------T------------------------------------- |
| 68 cont. and 86 | H-2K$^q$ | ------------------------------------------T------------------------K---------- |
| 69 cont. and 87 | H-2D$^d$ | -P-----------R---GD-----------------------T-E------------------K----E---GKE |
| 70 cont. and 88 | H-2D$^p$ | -P-------P-S-G---------------------------T--------------AL----N----E-E--- |
| 71 cont. and 89 | H-2D$^b$ | ---------P-SKGE---------------------------T------------------------N----R--E--- |
| 72 cont. and 89 | H-2L$^d$ | ---------P-SKGE---------------------------T------------------------N----R--E--- |
| 73 cont. | Q-7$^d$(27.1) | -P-------P-SYGA----------------------T--T---V------------------N----N-E-----GRW |
| 74 cont. | Q-7$^b$ | -P-------P-SYGA----------------------T--T----------------------N----N-E-----GRW |
| 75 cont. | Q-8$^b$ | -P-------P-SYGA----------------------T------------------------N----N-E--- |
| 77 cont. | Q-10$^b$ | -P--T----PGS-GD-----P----------------T-Q----------------------N------E--- |
| 78 cont. and 90 and 91 | PH-2$^d$-37 | -P-------P-S-E-----------------------T------------------A---------E--- |
| 79 cont. and 92 | 17.3A | -P--T----A---GD--------H-------------T----------------------A---S-E--K--- |
| 80 cont. and 93 | C25.1 | -P--T----P---GY----------R-----------T----------------A-----------K--E--- |
| 82 cont. and 94 | T1a$^a$-1 | -P--T----P---GY----------------------T---------------AL---S-E--K--- |
| 84 and 95 83 cont. and 96 | T1a$^a$-2 T1a$^a$-3 | -P--T----P---GY----------------------T---------------AL---S-E--K-------E--- -P--T----P---GY----------------------------------------A---S-E--K---E--- |
| | | 275 280 285 290 295 300 305 310 315 320 325 330 335 340 345 350 |
| | | EXON 5 EXON 6 EXON 7 EXON 8 |

-continued

| SEQ ID NO: | | EPPPSTVSNMATVAVLVVLGAAIVTGAVVAFVMKMRRRNT | GGKGGDYALAP | GSQTSDLSLPDCK | YMVHDPHSLA |
|---|---|---|---|---|---|
| 65 cont. | H-2K$^b$ | | | | |
| 66 cont. and 85 | H-2K$^d$ | KL------------TVII------------S--- | ----VN------ | ---------G--- | ---------- |
| 67 cont. | H-2K$^k$ | ------------TVII------------------ | ------------ | -------------- | ---------- |
| 68 cont. and 86 | H-2K$^q$ | ---A---TVII------------S---------- | ------------ | -------------- | ---------- |
| 69 cont. and 87 | H-2D$^d$ | ---S--KT-TVII--P-----VVIL--M------S---- | ------------ | ---S--M------ | - |
| 70 cont. and 88 | H-2D$^p$ | --------D-Y-VI-----------VFII--------M--S--- | ----T------ | ---S-EM--R--- | A |
| 71 cont. and 89 | H-2D$^b$ | --------D-Y-VI-----G----MAII------S-------- | ------------ | ---S-EM--R--- | A |
| 73 cont. | Q-7$^d$(27.1) | -----Y------I-V-D---VAII-------NS---X | ------------ | -------------- | |
| 74 cont. | Q-7$^b$ | -----Y------I-V-D---VAII-------NS---X | ------------ | -------------- | |
| 75 cont. | Q-8$^b$ | ------------M-I-----V-WPSLELWWIIX | ------------ | -------------- | |
| 77 cont. | Q-10$^b$ | ------------D-I-SHI-D-LWPSLKLWWYLX | ------------ | -------------- | |
| 78 cont. and 90 and 91 | PH-2-37 | ------------VII-------------V-IL-------S---HI | -V--CS---HVL | --KSFQT--DWPQ- | A |
| 79 cont. and 92 | 17.3A | ---Q-SMP-RT---RA-SS---M-IL-FMSGS---MWM--K-N | --N-D-NTA-Y | QNEREH-----TSGX | |
| 80 cont. and 93 | C25.1 | -L-QTSMP-RT---RA-SS---M-IL-FMSGS---MWM--K-N | --N-D-NTA-Y | QNEREH-----TPRAESEALGVEAGMKDLPSAPPLVSX | |
| 82 cont. and 94 | T1a$^a$-1 | ---Q-SMP-RT---RA-SS---M-IL-FMSGG---MWM--K-N | --N-D-NTA-C | QNEREH-----SPRAESEALGVEAGMKDLPSAPPLVSX | |
| 84 and 95 | T1a$^a$-2 | ---Q-SMP-RT---RA-SS---M-IL-FMSGS---MWM--K-K | --N-D-NTA-C | QNEREH-----SPRAESEALGVEAGLKDLPS | |
| 83 cont. | T1a$^a$-3 | ---Q-SMPTRTI-RA-AA---MVIL-VMTGSG-MWM--K-K | --NRD-NTA-C | QNEREH-----SAGDESDALGVEAGLKELPTAPPLVPX | |

The above sequences are grouped by exon where exons 2, 3, and 4 encode the extracellular domains, exon 5 encodes the transmembrane region, and exons 6, 7, and 8 encode the intracytoplasmic portions of the molecules. A indicates identity with the prototype; * indicates an unidentified residue; and § indicates a deletion used to facilitate alignment of the sequences. Stop codons are represented by x in some sequences. Source: Paul, supra, at pages 502–503.

The deduced protein sequences for members of the HLA-A2/A28 family are shown below. Sequences designated with A2 are serologically indistinguishable and have been selected by functional assays. The A28 family is divided into A68 and A69 specificities based on serologic data. Paul, supra, at page 511.

| SEQ ID NO: | | LEADER PEPTIDE |
|---|---|---|
| | | -20                -10 |
| 97 | HLA-A2.1 | MAVMAPRTLVLLLSGALALTQTWA |
| 98 | A2.4a | ------------------------ |
| 99 | A2.3 | ------------------------ |
| 100 | A2(Lee) | ------------------------ |
| 101 | A2.2Y | ------------------------ |
| 102 | AW69 | ------------------------ |
| 103 | AW68.2 | ------------------------ |
| 104 | AW68.1 | ------------------------ |

α₁ DOMAIN

| | | 10         20         30         40         50         60         70         80         90 |
|---|---|---|
| 97 cont. | HLA-A2.1 | GSHSMRYFFTSVSRPGRGEPRFLAVGYVDDTCFVRFDSDAASQRMEPRAPWIEQEGPEYWDGETRKVKAHSQTHRVDLGTLRGYYNISEA |
| 98 cont. | A2.4a | ---------Y------------------------------------------------------------------------------- |
| 105 | A2.4b | ---------Y------------------------------------------------------------------------------- |
| 106 | A2.1/.3 | ----------------------------------------------------------------------------------------- |
| 99 cont. | A2.3 | ---------Y------------------------------------------------------------------------------- |
| 100 cont. | A2(Lee) | ---------Y------------------------------------------------------------------------------- |
| 107 | A2.2F | --------------------------------------R-------------------------------------------------- |
| 101 cont. | A2.2Y | ---------Y----------------------------R-------------------------------------------------- |
| 108 | A2.4c | ---------Y----------------------------R-------------------------------------------------- |
| 102 cont. | AW69 | ---------Y-----------------------------------------------N------------------------------- |
| 103 cont. | AW68.2 | ---------Y-M---------------------------------------------RN--N---Q---D------------------- |
| 104 cont. | AW68.1 | ---------Y-----------------------------------------------RN--N---Q---D------------------- |
| | | 100        110        120        130        140        150        160        170        180 |

α₂ DOMAIN

-continued

| SEQ ID NO: | | |
|---|---|---|
| 97 cont. | HLA-A2.1 | DSHTVQRMYGCDVGSDWRFLRGYHQYAYDGKDYIALKEDLRSWTAADMAAQTTKHKWEAAHVAEQLRAYLEGTCVEWLRRYLENGKETLQRT |
| 98 cont. | A2.4a | ------------------------------------------------------------------------------------------ |
| 105 cont. | A2.4b | ---------C-------------------------------------------------------------------------------- |
| 106 cont. | A2.1/.3 | ------------------------------------------------------------------------------------------ |
| 99 cont. | A2.3 | -----------------------------------------------------------------------T--E--W------------ |
| 100 cont. | A2(Lee) | ------F------G---------------------------------------------------------------------------- |
| 107 cont. | A2.2F | ---------L--------------------------------------------------------W----------------------- |
| 101 cont. | A2.2Y | ---------L--------------------------------------------------------W----------------------- |
| 108 cont. | A2.4c | ---------L--------------------------------------------------------W----------------------- |
| 102 cont. | AW69 | ------L-------P-G-------------------------------------------------W----------------------- |
| 103 cont. | AW68.2 | ------L-M----------G-----R-D--------------------------------------W----------------------- |
| 104 cont. | AW68.1 | ------L-M----------G-----R-D--------------------------------------W----------------------- |

α₃ DOMAIN

| | | |
|---|---|---|
| 97 cont. | HLA-A2.1 | DAPKTHMTHHAVSDHEATLRCWALSFYPAEITLTWQRDGEDQTQDTELVETRPAGDGTFQKWAAVVVPSGQEQRYTCHVQHEGLPKPLTLRW |
| 98 cont. | A2.4a | ------------------------------------------------------------------------------------------ |
| 105 cont. | A2.4b | ------------------------------------------------------------------------------------------ |
| 106 cont. | A2.1/.3 | ------------------------------------------------------------------------------------------ |
| 99 cont. | A2.3 | ---------------------------------------------E------------------------------------------- |
| 100 cont. | A2(Lee) | ------------------------------------------------------------------------------------------ |
| 107 cont. | A2.2F | ------------------------------------------------------------------------------------------ |
| 101 cont. | A2.2Y | ------------------------------------------------------------------------------------------ |
| 108 cont. | A2.4c | ------------------------------------------------------------------------------------------ |
| 102 cont. | AW69 | ------------------------------------------------------------------------------------------ |
| 103 cont. | AW68.2 | ------------------------------------------------------V---------------------------------- |
| 104 cont. | AW68.2 | ------------------------------------------------------V---------------------------------- |

| SEQ ID NO: | TRANSMEMBRANE REGION | | | CYTO. 1 | CYTO. 2 | CYTO. 3 |
| --- | --- | --- | --- | --- | --- | --- |
| | | 280 290 300 310 | | 320 | 330 340 | |
| 97 cont. | HLA-A2.1 | EPSSQPTIPIVGIIAGLVLFGAVITGAVVAAVMWRRKSS | | DRKGGSYSQAA | SSDSAQGSDVSLTACK | V |
| 98 cont. | A2.4a | ------------------------------------- | | ----------- | ---------------- | - |
| 99 cont. | A2.3 | ------------------------------------- | | ----------- | ---------------- | - |
| 100 cont. | A2(Lee) | ------------------------------------- | | ----------- | ---------------- | - |
| 101 cont. | A2.2Y | ------------------------------------- | | ----------- | ---------------- | - |
| 102 cont. | AW69 | ------------------------------------- | | ----------- | ---------------- | - |
| 103 cont. | AW68.1 | ------------------------------------- | | ----------- | ---------------- | - |
| 104 cont. | AW68.2 | ------------------------------------- | | ----------- | ---------------- | - |

Amino acid sequences of representative class II α chains deduced from cDNA clones are shown below. Residues identical to DRα sequence are indicated by hyphens. Numbering is in reference to the DRa sequence. Paul, supra, at page 519.

deduced from cDNA clones are shown below. Residues identical to DRε sequence are indicated by hyphens. Numbering is in reference to the DRβ sequence. Paul, supra, at page 520.

```
SIGNAL SEQUENCES
                -20       -10
                 |         |
DRα         MAISGVPVLGFFIIAVLMSAQESWA
DQα1         -ILNKALL--ALALTTV--PCGG
DPα    (MRPEDR)-FHIRAVI-RALSL-F-L-LRGAG-
DNα            --LRAGL----HTLMT-L-P--AG-
I-Aα           -PR-RALI--VLALTTML-LCGG
I-Eα           --TIGAL--R--F------S-K---

α1 DOMAIN
              10        20        30        40        50        60        70        80
               |         |         |         |         |         |         |         |
DRα     IKEEHV IIQAEFYLNPDQSGEFMFDFDGDEIFHVDMAKKETVWRLEEFGRFASFEAQGALANIAVDKANLEIMTKRSNYTPITN
DQα1    ED-VAD--ASCGVNL-QFYGP--QYTHE-----Q-Y--LER---A--WP--SK-GG-DP----R-M--A-H---N---I--Y-S-AA--
DPα       --AD-- STY-A-VQTHRPT-----E--E--M-Y--LD------H-----QAF------G-----ILNN--NTLIQ---H-QA--
DNα       T-AD-MGSYGPA--QSYGA--Q-THE----EEQL-S--LK-S-A----P---D--R-DP--G--G--AI--H-D-LVE-----RSRAI-
I-Aα    EDDIEAD--GSYGIT--QS-GDI-QYT-E-----L-Y--LD------M-P--AQLRR--P--G-Q---TG-H----L-----S--A--
I-Eα       -----T --------L--KR--------------IE-S--I------AK------------------DV-KE---N--DA-

α2 DOMAIN
           90       100       110       120       130       140       150       160       170
            |         |         |         |         |         |         |         |         |
DRα     VPPEVTVLTNSPVELREPNVLICFIDKFTPPVVNVTWLRNGKPVTTGVSETVFLPREDHLFRKFHYLPFLPSTEDVYDCRVEHWGLDEPLLKHW
DQα1    EV-----FSK---T-GQ--T---LV-NIF-----I---S--QS--ED----S--SKS---S-F-IS---T----ADEI---K-------Q------
DPα     D------FPKE----GQ--T---H----F---L-----C--EL--E--A-SL----T-YS--H-----T-V--A--F---------Q------
DNα     ---R------PK-R---GQ--I---IV-NIF---I-I------QT--E--AQ-SFYSQP------------V--A------Q-------A---R--
I-Aα    EA-QA--FPK---L-GQ--T-----V-NIF---I-I------S--S--D--Y--S-FVNR-YS-H-LS--T-I--DD-I---K------E--V----
I-Eα    -A------SR--N-G---I--------S------------R---E---------D----------T-----D-F---E-D----E---R-A-

CONNECTING PEPTIDE    TRANSMEMBRANE REGION    CYTOPLASMIC REGION
           180       190               200       210         220
            |         |                 |         |           |
DRα     EFDAPSPLPETTE            NVVCALGLTVGLVGIIIGTIFII  KGLRKSNAAERRGPL
DQα1    -PEI-A-MS-L--            T-------S---M--VV--V---  Q---SVG-SRHQ---
DPα     -AQE-IQM-----            T-L-----VL----F-V--VL--  -S--SGHDPRAQ-T-
DNα     -LQV-I-P-DAM-            TL------AI----FLV--VL--  M-TYV-SVPR
I-Aα    -PEI-A-MS-L--            T-------S-----VV------  Q---SGGTSRHP---
I-Eα    --EEKTL----K-            --------F------VV-I-L-M  --IK-R-VV---QGAL
```

Amino acid sequences of representative class II β chains

```
SIGNAL SEQUENCES
           -30       -20       -10
            |         |         |
DRβ        MVCLKLPGGSCMTALTVTLMVLSSPLALA
DQβ    MSWKKS-RI--DLRVATV-LM-AI---S--EG
DPβ        MV-QVSAAPRTV---AL----LTSVVQG
DOβ         MGSGWVPWVV--L-N-TR-D-SMTQG
I-Aα       MALQIPSLLLS-AV-V-------RTEG
I-Eα       MVW--RVP-VA-VILL-T---P-V--V

α1 DOMAIN
             10        20        30        40        50        60        70        80        90
              |         |         |         |         |         |         |         |         |
DRβ     GDTRPRFLWQLKFECHFFNGTERVRLLERCIYNQEESVRFDSDVGEYRAVTELGRPDAEYWNSQKDLLEQRRAAVDTYCRHNYGVGESFTVQRR
DQβ1    R-SPED-VY-F-GL-Y-T-------GVT-H---R--Y--------V-----PQ---V--------EV--GA--S--RV-----E-AYRGIL---
DPβ     RA-PENY-F-GRQ--YA----Q-  F---Y---R--F---------F----------E---------I---EE--VP-RM-----EL-GPM-L---
DOβ     T-SPED-VI-A-AD-Y-T----K-QFVV-F-F-L--Y---------MFV-L-K--Q----Q---RL----RS-Q---GV-----RL-AP---G-K
I-Aα    -NSERH-VA---G--Y-T---Q-I-SVN-Y---R--W----------------------PEI--RT--E---V-----EGV-TH-SL--
I-Eα    R--P-----EYVTS-----Y---QH--F---F---R--NL-----------------N-----PEI--DA--S---------EISDKFL-R--

α2 DOMAIN
            100       110       120       130       140       150       160       170       180
             |         |         |         |         |         |         |         |         |
DRβ     VEPKVTVYPSKTQPLQHHNLLVCSVSGFYPGSIEVRWFRNGQEEKAGVVSTGLIQNGDWTFQTLVMLETVPRSGEVYTCQVEHPSVTSPLTVEW
```

-continued

```
DQβ    ---T--IS--R-EA-N-----I---TD---SQ-K------D---T------P--R--------I-----MT-QR-D----H-----LQ--I----
DPβ    -Q-R-N-S---KG----------H-TD------Q----L-----T------N--R--------I-----MT-QQ-D--------T-LD--V----
DOβ    -Q-E-----ER-PL-HQ----H---T-----D-KIK--L-----R---M---P-R--------V----MT-EL-H-----L-D-S-LL--VS---
I-Aα   EQ-N-AISL-R-EA-N---T------TD---AK-K----------TV--S--Q--R--------V----MT-HQ------H-----LK--I----
I-Eα   ---T-----T-----E---------D----N---------K--ET-I-----VR-------------W--Q-------------L-D-V----
```

```
        CONNECTING PEPTIDE    TRANSMEMBRANE REGION    CYTOPLASMIC REGION
        190                   200       210           220       230
        |                     |         |             |         |
DRβ     RARSESAQSKM           LSGVGGFVLGLLFLGAGLFI    YFRNQKGHSGLQPTGFLS
DQβ     --Q--------           -----------I---L--I-    RQ-SR-      -L-H
DPβ     K-Q-D-R--T            -T-A-------IIC-V-I-M    HR-SK-VQR-SA
DOβ     --Q--YSWR--           ---IAA-L---I--LV-IV-    QL-A---YVRT-MS-NEVSRAVLLPQSC
I-Aα    --Q----R---           ---I--C---VI---L----    RH-S---PR-PP-A-L-Q
I-Eα    K-Q-T---N--           --------------------    -------Q-E-----L--
```

It will be understood that this invention encompasses biochemical variants of class I and class II MHC domains. For example, following is a comparison of the polymorphic residues in DQα first domain sequences. Numbers correspond to amino acid residues. Identity with the DR1 DQw1.1 sequence is indicated by a hyphen; parentheses mark deleted amino acids; and a blank space indicates that no sequence data are available. Paul, supra, at page 524.

residues in DQβ first domain sequences. Numbers correspond to amino acid residues. Identity with the DR1 DQw1.1 sequence is indicated by a hyphen, and a blank space indicates that no sequence data are available. Paul, supra, at page 525.

```
              11 18 25 26 34 40 41 45 47 48 50 51 52 53 54 55 61 64 66 69 75 76 80
              |  |  |  |  |  |  |  |  |  |  |  |  |  |  |  |  |  |  |  |  |  |  |

DR1 DQw1.1    C  F  Y  T  E  E  R  A  R  W  E  F  S  K  F  G  G  R  M  A  I  M  Y

DR2 DQw1.2    -  -  -  -  Q  -  -  -  -  -  -  -  -  -  -  -  -  -  -  -  -  -  -

DR2 DQw1.AZH  -  -  -  -  Q  -  -  -  -  -  -  -  -  -  -  -  -  -  -  -  -  -  -

DRw6 DQw1.18     F  -  Q  -  K  -  -  -  -  -  -  -  -  -  -  -  -  -  -  -  -  -

DRw6 DQw1.19     -  -  Q  -  -  -  -  -  -  -  -  -  -  -  -  -  -  -  -  -  -  -

DRw8 DQ1         F  -  Q  -  K  -  -  -  -  -  -  -  -  -  -  -  -  -  -  -  -  -

DR3 DQw2      Y  S  -  -  Q  G  -  V  C  L  V  L  R  Q  R  [  ]  F  T  I  L  S  L  S

DR4 DQw3.1    Y  S  -  S  -  -  -  V  Q  L  L  -  R  R  R  R  F  T  I  L  -  V  S

DR4 DQw3.2    Y  S  -  S  -  -  -  V  Q  L  L  -  R  R  R  R  F  T  I  L  -  V  S

DR5 DQw3.1    Y  S  -  -  Q  G  -  V  C  L  V  L  R  Q  R  [  ]  F  T  I  L  S  L  S

DR9 DQw3      Y  S  -  S  -  -  -  V  Q  L  L  -  R  R  R  R  F  T  I  L  -  V  S

DR8 DQblank   Y  S  -  -  Q  G  -  V  C  L  V  L  R  Q  R  [  ]  F  T  I  T  -  L  S
```

Similarly, following is a comparison of the polymorphic

```
              3  9 13 14 26 28 30 37 38 45 46 47 52 53 55 56 57 66 67 70 71 74 75 77 84 85 86 87 89 90
              |  |  |  |  |  |  |  |  |  |  |  |  |  |  |  |  |  |  |  |  |  |  |  |  |  |  |  |  |  |

DR1 DQw1.1    S  Y  G  L  G  T  H  Y  V  G  V  Y  P  Q  R  P  V  E  V  G  A  S  V  R  E  V  A  Y  G  -

DR2 DQw1.2    -  F  -  M  L  -  Y  -  A  -  -  -  -  -  -  -  -  D  -  -  -  T  E  L  T  -  -  -  F  -  -

DR2 DQw1.12   P  L  A  M  Y  -  Y  D  -  -  -  -  -  -  -  -  -  D  D  I  R  T  E  L  T  -  -  -  F  -  -

DR2 DQw1.AZH  -  -  -  -  -  -  -  -  -  -  -  -  -  -  -  -  -  S  -  -  -  -  -  -  -  -  -  -  -  -
```

-continued

```
DRw6 DQw1.18           L  -  -  -  A  -  -  -  -  -  -  -  D  -  -  -  T  E  L  T
DRw6 DQw1.19  -  -  -  M  L  -  -  -  A  -  -  -  -  -  -  -  -  -  -  R  T  E  L  T  -  -  -  G  -  -
DR3  DQw2              M  L  S  S  I  -  -  E  F  L  L  L  -  A  D  I  R  K  A  -  -  Q  L  E  L  T  -
DR7  DQw2     -  -  -  M  L  S  S  I  -  -  E  F  L  L  L  -  A  D  I  R  K  A  -  -  Q  L  E  L  T  T
DR4  DQw3.1   -  -  A  M  Y  -  Y  -  A  E  -  -  -  -  L  P  -  D  -  -  R  T  E  L  T  Q  L  E  L  T  T
DR4  DQw3.2   -  -  -  M  L  -  Y  -  A  -  -  -  -  -  L  P  -  A  -  -  R  T  E  L  T  Q  L  E  L  T  T
DR5  DQw3.1   -  -  A  M  Y  -  Y  -  A  E  -  -  -  -  L  P  -  D  -  -  R  T  E  L  T  Q  L  E  L  T  T
DR9  DQw3.3   -  -  -  M  L  -  Y  -  A  -  -  -  -  -  L  P  -  D  -  -  R  T  E  L  T  Q  L  E  L  T  T
DR8  DQblank  -  F  -  M  -  -  Y  -  A  -  -  -  -  -  L  -  L  D  D  I  E  D  -  -  T  Q  L  E  L  T  T
```

Genes encoding other MHC gene products can be determined from the physical map of the MHC gene complex for the mammalian species of interest.

9. Antibodies To Altered Determinants And Compositions Of The Invention

The altered MHC class I and class II determinants of the invention and compositions containing antigens bound to the determinants are useful for the preparation of antibodies that recognize these substances. The antibodies have diagnostic uses, application in mammalian therapy, and use in the study of MHC and cellular processes.

More particularly, polyclonal or monoclonal antibodies can be used in a variety of applications. Among these the neutralization of MHC gene products by binding to the gene products on cell surfaces. They can also be used to detect MHC gene products in biological preparations or in purifying corresponding MHC gene products or the altered MHC class I and class II determinants of the invention, such as by affinity chromatography.

Antibodies according to the present invention can be prepared by any of a variety of methods. For example, cells expressing an altered determinant or a functional derivative thereof can be administered to an animal in order to induce the production of sera containing polyclonal antibodies that are capable of binding the altered determinant. In addition, antibodies can be prepared to a variety of altered MHC class I and class II determinants of the invention and compositions containing antigens bound to the determinants in a similar manner.

In a preferred method, the antibodies are monoclonal antibodies, which can be prepared using hybridoma technology (Kohler et al., *Nature* 256:495 (1975); Kohler et al., *Eur. J. Immunol.* 6:511 (1976); Kohler et al., *Eur. J. Immunol.* 6:292 1976); Hammerling et al., In: *Monoclonal Antibodies and T-Cell Hybridomas*, Elsevier, N.Y., pp. 563–681 (1981)). In general, such procedures involve immunizing an animal with the altered MHC determinant or the altered MHC-antigen composition. Splenocytes of the animals are extracted and fused with a myeloma cell line. After fusion, the resulting hybridoma cells can be selectively maintained in HAT medium, and then cloned by limiting dilution as described by Wands, J. R., et al. *Gastroenterology* 80:225–232 (1981). The hybridoma cells obtained are then assayed to identify clones secreting antibodies capable of binding the altered MHC determinant or the composition.

See also 2,658,197 (A1) [90 01769], Feb. 14, 1990, "Restricted Monoclonal Antibodies That Recognize A Peptide That Is Associated With An Antigen Of A Major Histocompatibility Complex, Use In Diagnosis and Treatment," Huynh Thien Duc Guy, Pririe Rucay, Philippe Kourilsky; National Institute of Health and Medical Research.

The antibodies can be detectably labeled. Examples of labels that can be employed in the present invention include, but are not limited to, enzymes, radioisotypes, fluorescent compounds, chemiluminescent compounds, bioluminescent compounds and metal chelates.

Examples of enzymes include malate dehydrogenase, staphylococcal nuclease, delta-V-steroid isomerase, yeast alcohol dehydrogenase, alpha-glycerophosphate dehydrogenase, triose phosphate isomerase, biotin-avidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase.

Examples of isotopes are $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se. Among the most commonly used fluorescent labeling compounds are fluoroscein, isothiocyanate, rhodamine, phycoerythrin, phycocyanin, allophycocyanin, o-phthaldehyde and fluorescamine.

Examples of typical chemiluminescent labeling compounds are luminal, isoluminol, theromatic acridinium ester, imidazole, acridinium salts, oxalate ester, and dioxetane.

Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art. Bioluminescent compounds for purposes of labeling include luciferin, luciferase and aequorin.

The antibodies and antigen of the present invention are ideally suited for the preparation of a kit. Such kit may comprise a carrier means being compartmentalized to receive one or more container means, such as vials, tubes and the like, each of said container means comprising the separate elements of the assay to be used.

10. Diagnostic Applications

The altered MHC class I and class II determinants, compositions containing antigens bound to the altered determinants, and antibodies to these substances are useful in diagnostic applications. For example, the altered determinants can be used to target lymphocyte receptors, such as CD4+ and CD8+ receptors of T lymphocytes, and the resulting bound determinant can be assayed, for instance, by means of an antibody to the bound determinant. In addition, it will be understood that the altered MHC determinants of the invention can be labeled in the manner previously described for antibodies. In this case, the label on the altered MHC determinant can be detected and quantified. Compositions comprising an antigen bound to an altered determinant of the invention can be used in a similar manner with MHC-restricted receptors recognizing the antigen and the determinant.

Typical examples of assays based on the antibodies of the invention are radioimmunoassays (RIA), enzyme immunoassays (EIA), enzyme-linked immunosorbent assays (ELISA), and immunometric or sandwich immunoassays, including simultaneous sandwich, forward sandwich, and reverse sandwich immunoassays.

In the preferred mode for preforming the assays it is desirable to employ blockers in the incubation medium to assure that non-specific proteins, protease, or human antibodies to immunoglobulins present in the experimental sample do not cross-link or destroy the antibodies and yield false positive or false negative results. Nonrelevant (i.e. non-specific) antibodies of the same class or subclass (isotype) as those used in the assays (e.g. IgG, IgM, etc.) can be used as blockers. In addition, a buffer system should be employed. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors can be added to the buffer.

Well known solid phase immunoadsorbents, such as glass, polystyrene, polypropylene, dextran, nylon and other materials, in the form of tubes, beads, and microtiter plates formed from or coated with such materials, can be employed in the present invention. Immobilized antibodies can be either covalently or physically bound to the solid phase immunoadsorbent by techniques, such as covalent bonding via an amide or ester linkage, or by adsorption.

11. Immunization and Therapeutic Administration

In another embodiment of this invention, the altered MHC class I and class II determinants and compositions containing antigens bound to the determinants and antibodies to these substances can be administered to a mammal to produce a therapeutic effect. For example, immune responses to self components represent a failure of immunological tolerance. As a result, clones of T cells and B cells emerge bearing receptors for self-antigens, which can lead to the production of self-directed antibodies, cytotoxic T cells, and inflammatory T cells. Such a breakdown in tolerance produces an autoimmune response that can cause autoimmune diseases. Administration of the altered determinants, compositions, or antibodies of the invention can intervene in these processes. Thus, for example, this invention can be utilized to treat T cell mediated autoimmune diseases, such as thyroiditis and multiple sclerosis.

This invention also provides altered MHC class I and class II determinants for use in therapeutic or vaccine compositions. Conventional modes of administration can be employed. For example, administration can be carried out by oral, respiratory, or parenteral routes. Intradermal, subcutaneous, and intramuscular routes of administration are preferred when the vaccine is administered parenterally.

The ability of the altered determinants and compositions of the invention to exhibit a therapeutic or immunizing effect can be enhanced by emulsification with an adjuvant, incorporation in a liposome, coupling to a suitable carrier, or even in cells, or by combinations of these techniques. For example, the altered determinants and compositions can be administered with a conventional adjuvant, such as aluminum phosphate and aluminum hydroxide gel, in an amount sufficient to mediate humoral or cellular immune response in the host. Similarly, these reagents can be bound to lipid membranes or incorporated in lipid membranes to form liposomes. The use of nonpyrogenic lipids free of nucleic acids and other extraneous matter can be employed for this purpose.

In addition, any of the common liquid or solid vehicles can be employed, which are acceptable to the host and do not have any adverse side effects on the host nor any detrimental effects on the reagents of the invention. Conveniently, phosphate buffered saline at a physiological pH can be employed as the carrier. One or more injections may be required, particularly one or two additional booster injections. It will be understood that conventional adjuvants, such as SAF-1, complete Freund's adjuvant and incomplete Freund's adjuvant, or oil-based adjuvants, such as mineral oil, can be administered with the reagents of the invention to elicit an increased antibody or cell-mediated immune response.

The immunization schedule will depend upon several factors, such as the susceptibility of the host and the age of the host. A single dose of the reagents of the invention can be administered to the host or a primary course of immunization can be followed in which several doses at intervals of time are administered. Subsequent doses used as boosters can be administered as needed following the primary course.

In an initial protocol, the mouse can be injected with about 10 to about 20 $\mu$g of the altered MHC determinant of the invention per injection. The usual vaccine dosages can be employed in humans.

In addition to the antibodies produced for kits and diagnostic assays, antibodies of the present invention can be humanized by procedures well known in the art (using either chimeric antibody production or CDR grafting technology). U.S. Pat. No. 4,816,567 Cabilly et al., EPA 0120694 Publication No., assigned to Celltech, EPA 0173494 Publication No. assigned to Stanford University, and EPA 0125023 Publication No. assigned to Genentech, describing chimeric antibody procedures and EPA 0194276 Publication No. assigned to Celltech describing CDR grafting procedures.

The humanized antibodies would be prepared from antibodies obtained against specific MHC-antigen complexes. The humanized antibodies could then be used therapeutically in humans so as to avoid the problems associated with the use of non-human antibodies in human therapy.

This invention will now be described in greater detail in the following Examples.

EXAMPLE I

Engineering of Single-Chain Murine Class I Major Transplantation Antigen

Single-chain mouse $K^d$ molecules (SC-$K^d$) were engineered by connecting residue 276 of $K^d$ heavy chain to the first residue of $\beta_2$-microglobulin through spacers of various lengths, and expressed intracellularly in monkey COS-1 cells. Labeled SC-$K^d$ molecules were found to react with several monoclonal antibodies, which recognize native $K^d$ molecules. SC $K^d$-15 (with a spacer of 15 residues) was studied in more detail. It could be purified and shown to regain a native-like structure after treatment with denaturing agents. Purified SC-$K^d$-15 could bind certain peptides in a manner qualitatively similar to that of $K^d$.

Plasmid constructs

Figure 5A:
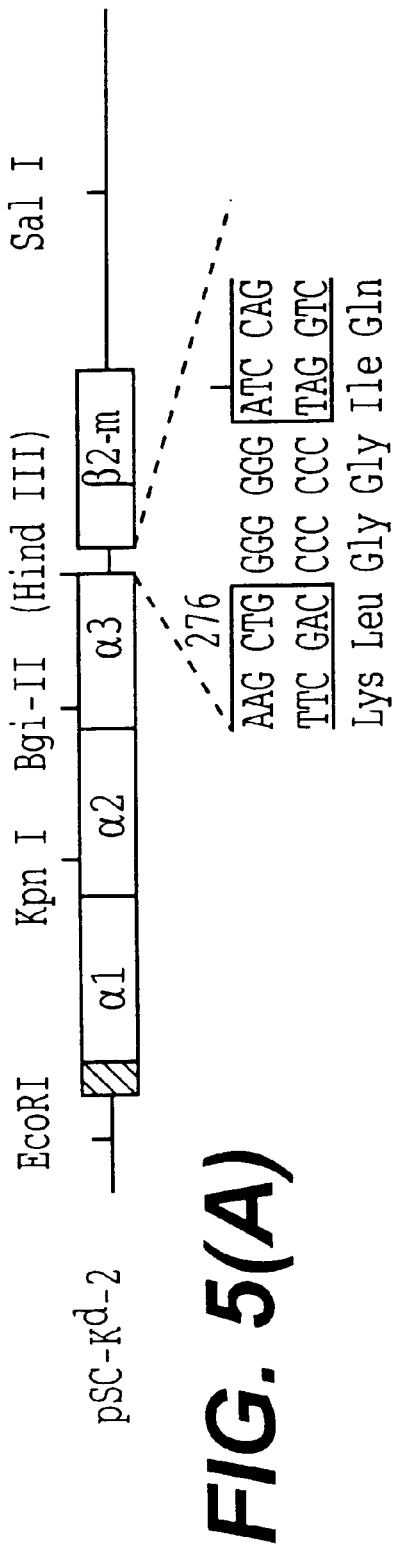
FIG. 5 depicts DNA constructs of the parental plasmid, pSC-$K^d$-2, in (A) (SEQ ID NO:1 and SEQ ID NO:2). Various spacers are depicted in (B) Spacer SC-10 corresponds to SEQ ID NO:3 and SEQ ID NO:4; spacer SC-13 corresponds to SEQ ID NO:5 and SEQ ID NO:6; spacer SC-15 corresponds to SEQ ID NO:7 and SEQ ID NO:8; spacer SC-17 corresponds to SEQ ID NO:9 and SEQ ID NO:10; spacer SC-19 corresponds to SEQ ID NO:11 and SEQ ID NO:12; and spacer SC-21 corresponds to SEQ ID NO:13 and SEQ ID NO:14.

A full-length $K^d$ cDNA (Lalanne, J. -L., Delarbre, C., Gachelin, G., and Kourilsky, P., *Nucleic Acids Res.,* 1983. 11:1567) was cut by Hind III (at the level of residue 276) and fused in phase, by a Gly—Gly coding linker, to $\beta_2$m cDNA (Daniel, F., Morello, D., LeBail, O., Chambon, P., Cayre, Y., and Kourilsky, P., *EMBO J.* 1983. 2:1061) in which a Bam HI site overlapping the first Ile codon of mature $\beta_2$m had been introduced by site-directed mutagenesis. The block was cloned in a mammalian expression vector, pKC3 (kindly provided by Dr. Hanahan, U.C.S.F.), which contains the SV40 promoter and origin of replication, yielding pSC-$K^d$-2 (shown in Gene Constructs discussion, FIG. 5A). Synthetic linkers of different lengths were then ligated at the Bam HI site of pSC-$K^d$-2 (FIG. 5B). For example, the SC-$K^d$-15 liner was:

5' GATCGGATCCGGAGGCGGTGGATCCG-GTGGCGGCGGTTC 3'

3' CCTAGGCCTCCGCCACCTAGGCCACCGC-CGCCAAGCTAG 5'

Bam HI digestion of pSC-$K^d$-15 and religation yielded pSC-$K^d$-10. pSC-$K^d$-13, -17, -19 and -21 were obtained by cloning the appropriate linkers into the Bam HI site of pSC-$K^d$-10. All spacers and junctions were sequenced.

Transfection and immunoprecipitation

COS-1 cells (about $3.5 \times 10^6$ cells in 60-mm plates) grown in DMEM supplemented with 10% newborn serum, penicillin, streptomycin and L-glutamine, were transfected one day after plating with 0.5 ml calcium phosphate mixture containing 5 µg of CsCl-purified plasmid DNA. Transfection efficiencies were occasionally monitored with pCH110 plasmid expressing *E. coli* β-galactosidase (Pharmacia, Uppsala, Sweden). Thirty-six hours after transfection, cells were radiolabeled with [$^{35}$S] methionine (45 µCi/plate=1.67 m Bq/plate) for 4 h at 37° C., then washed once in PBS and collected in 1 ml lysis buffer (10 mM Tris-HCl, pH 7.4, 1 mM EDTA, 150 mM NaCl, 1% w/v NP40, BSA 10 mg/ml) containing 20 mM iodoacetamide and 1 IU/ml aprotinin. Lysates were precleared with protein A-Sepharose for 1 h at 4° C., and SN were incubated for 18 h at 4° C. with either 30 µl of culture SN or 5 µl of purified mAb and protein A-Sepharose. The beads were washed three times and the proteins were eluted in Laemmli buffer with 2-ME and analyzed by SDS-PAGE on 12% gels. Gels were fixed, treated with Amplify (Amersham Int., Amersham, GB), dried and visualized by autoradiography with use of Kodak (Rochester, N.Y.) XAR-X-ray film.

For endoglycosidase H (Endo H) treatments, samples were equilibrated in 0.5% SDS, 1 M 2-ME, boiled for 2 min., precipitated with 15% trichloroacetic, rinsed with acetone and resuspended in 50 µl 50 mM sodium citrate, pH 5.5, 0.1% SDS, 20 mM2-ME. Endo H (Boehringer-Mannheim, Mannheim, FRG) was added to a final concentration of 150 mU/ml, samples were incubated at 37° C. for 24 h, and then analyzed by SDS PAGE.

Immunoaffinity purification of SC-$K^d$-15 protein

COS-1 cells (usually $10^7$ cells) were transfected with pSC-$K^d$-15 DNA, labeled and lysed as above. SN were precleared with protein A-Sepharose for 1 h at 4° C. then incubated for 18 h at 4° C. with 100 µl mAb 34.1.2 covalently bound to protein A beads. After the final wash in PBS, SC-$K^d$-15 was eluted from the matrix with an equal volume of 3 M thiocyanate for 10 min on ice. After an overnight dialysis in PBS containing 0.1% NP40, 0.05% Tween and 0.2% BSA, SC-$K^d$-15 was used in direct binding test as below. Its purity was assessed by SDS-PAGE.

Peptides and Peptide Binding Assays

Peptides used in this study are described in Choppin et al. (Choppin, J., Martinon, F., Gomard, E., Bahraoui, E., Connan, F., Bouillot, F., and Levy, J. -P, *J. Exp. Med.,* 1990. 172:889 and references therein), except for HLA-Cw3 and HLA-A24 described in Maryanski, J. Ll, Pala, P., Cerottini, J. -C, and Corradin, G., *J. Exp. Med.* 1988. 167:1391. Binding assays were performed as described in Choppin, J., Martinon, F., Gomard, E., Bahraoui, E., Connan, F., Bouillot, F., and Levy, J. -P, *J. Exp. Med.,* 1990. 172:889. DR3, DRw13, and $K^d$ molecules were also purified and iodinated as in Choppin, J., Martinon, F., Gomard, E., Bahraoui, E., Connan, F., Bouillot, F., and Levy, J. -P,*J. Exp. Med.,* 1990. 172:889.

Gene Constructs

The C-terminal part of the $K^d$ heavy chain truncated in the hinge region was hooked to the N-terminal part of $\beta_2$-microglobulin with an appropriate spacer. From the 3-D structure of $K^d$ (Prochnicka-Chalufour, A., Casanova, J. -L, Kourilsky, P., and Claverie, J. -M, *Res. Immunol.,* 1989. 140:133) modeled after the HLA-A2 structure of Bjorkmann et al. (Bjorkmann, P. J., Saper, M. A., Samraoui, B., Bennet, W. S., Strominger, J. L., and Wiley, D. C., *Nature* 1987. 329:506), the minimal length of a polyglycine type of spacer was estimated to be 11 residues, starting from residue 276 in the $K^d$ amino acid sequence (which allows the use of a convenient restriction site in the $K^d$ cDNA).

Two full-length cDNA clones encoding $K^d$ (Lalanne, J. -L, Delarbe, C., Gachelin, G., and Kourilsky, P., *Nucleic Acids Res.,* 1983. 11:1567) and $\beta_2$-microglobulin (Daniel, F., Morello, D., LeBail, O., Chambon, P., Cayre, Y. and Kourilsky, P., *EMBO J.* 1983. 2:106) were connected by synthetic oligonucleotides encoding the spacers. The latter were designed as repeats of several glycines and one serine, (see discussion Plasmid Constructs). A series of pSC-$K^d$-coding of cDNA with spacers of 2, 10, 13, 15, 17, 19 and 21 amino acid residues were thus obtained. The verified sequences are shown in FIG. 6.

Expression of SC-Kd in transfected monkey COS-1 cells

COS-1 cells (in which the recombinant plasmids replicate) were transiently transfected for 36 h and labeled with [$^{35}$] methionine for 4 h. SC-$K^d$ molecules were not directly detectable by electrophoresis of SN or cell extracts. For immunoprecipitation, mAb 34-1-2 (Ozato, L., Mayer, N. and Sachs, D. H., *Transplantation,* 1982. 34:113), which reacts with native $K^d$ and $D^d$.

SN contained 20–50 fold less immunoprecipitable material than cellular extracts. This is not unexpected because the $K^d$ heavy chain truncated at the level of the Hind III site is not secreted by COS-1 cells (Chambon, P., D.E.A.. thesis, University of Paris, 1987). In cellular extracts, bands corresponding to proteins with an apparent molecular mass of about 52 kDa were specifically precipitated, and their mobility decreased slightly as the length of the spacer increased (FIG. 6A, SC-$K^d$-2,-10, -13,-17,-19,-21; for SC-$K^d$-15, see FIG. 6B). No band was seen with mock-transfected cells and 34-1-2 (FIG. 8A, lanes NT and pKC), nor with transfected cells and an irrelevant antibody (F23, 1; FIG. 6B). After the results of Townsend et al. (Townsend, A., Ohlen, C., Bastin, J., Ljunggren, H. -G., Foster, L., and Karre, K., *Nature* 1989. 340:443) with the RMA-S mutant cell line, whether the addition of large amounts of an immunogenic peptide (influenza NPR$^-$) was investigated and found to have no effect (FIGS. 6A and 6B). In much of the following work, SC-$K^d$-15 was arbitrarily chosen as the prototype SC-$K^d$ molecule.

In separate studies using baculovirus vectors, it has been verified that 34-1-2 reacts very poorly with the $K^d$ heavy chain expressed in insect cells in the absence of mouse β$_2$-microglobulin (about 20- to 50-fold fold less than K$^d$ associated to β$_2$-microglobulin). Reactivity with 34-1-2 is thus a strong indication that K$^d$ heavy chain is properly associated with β$_2$-microglobulin. To probe other parts of the K$^d$ molecule, other K$^d$-specific mAb (97-G and 20-8-4 (Ozato, L., Mayer, N. and Sachs, D. H., *Transplantation*, 1982. 34:113 and Rebai, N., Mercier, P., Kristensen, T., Devaux, C., Malissen, B., MAwas, C., and Pierres, M., *Immunogenetics* 1983. 17:57) were used and identical results were obtained. As an example, the SC-K$^d$-2 and SC-K$^d$-15 bands precipitated by mAb 20-8-4 are shown in FIG. 6B. The exact specificity of 97-G is not known, but the epitope recognized by 20-8-4 has been shown to include residues 82 and 89 belonging to the first domain of K$^d$ (Abastado, J. -P., Jaulin, C., Schutze, M. -P., Langlade-Demoyen, P., Plata, F., Ozato, K., and Kourilsky, P., *J. Exp. Med.* 1987. 166:327. Thus, this epitope is properly folded in SC-K$^d$-2 and SC-K$^d$-15 (as well as in other SC-K$^d$ molecules.

The state of glycosylation of intracellular SC-K$^d$-15 was assessed by treatment with Endo H. The molecule appears to be fully Endo H sensitive (FIG. 6C) and, after treatment, its apparent molecular mass is about 45 kDa, which fits the expected molecular mass of non-glycosylated SC-K$^d$-15 devoid of its signal peptide (390 amino acids). These results suggest that most of the SC-K$^d$-15 molecules are found in the endoplasmic reticulum in a high-mannose form.

With all three mAb, the precipitated SC-K$^d$-2 band was always 5–10 fold less intense than that obtained with SC-K$^d$ molecules with longer spacers. However, the Gly—Gly spacer is unlikely to allow proper association of β$_2$-microglobulin to the heavy chain. A 12-kDa band, presumably monkey β$_2$-microglobulin, is co-precipitated in relatively much higher amounts with SC-K$^d$-2 than with other SC-K$^d$ (FIG. 6D). This suggests that monkey β$_2$-microglobulin may associate better with SC-K$^d$-2 than with other SC-K$^d$ where the longer spacer permits proper folding of the murine β$_2$-microglobulin over the K$^d$ heavy chain, which could explain the detection of some SC-K$^d$-2 molecules. In any case, monkey β$_2$-microglobulin does not play a compulsory role in the folding of SC-K$^d$-15 since it has been possible to produce immunoprecipitable SC-K$^d$-15 in insect cells infected by a recombinant baculovirus.

Purification and peptide binding

The reactivity of SC-K$^d$ molecules with three distinct mAb provided evidence for their native-like character Nevertheless, it was necessary to purify these molecules, check their ability to fold back after treatments which separate heavy chain from β$_2$m, and finally test whether they were able to bind peptides.

A solid-phase matrix, made of 34-1-2 coupled to protein A beads, was used to purify $^{35}$S-labeled SC-K$^d$-15 from lysates of transiently transfected COS-1 cells. Treatment with 3 M sodium thiocyanate eluted the protein with a reasonable yield (about 70%) as assessed by a second immunoprecipitation with 34-1-2. After electrophoresis, the purified material ran as a single 52-kDa band. This confirmed that reactivity with 34-1-2 can be regained in the absence of detectable monkey β$_2$-microglobulin. This eluting treatment would normally dissociate heavy chain from β$_2$-microglobulin (Elliott, T., and Eisen, H. N., *Proc. Natl. Acad. Sci., USA* 1990. 87:5213). In addition 6 M urea was also used with similar results (not shown).

K$^d$ molecules isolated from the spleen of BALB/c mice were then purified and iodinated. They were purified by affinity chromatography on a 20-8-4 mAb column and compared binding of peptides by the latter and by $^{35}$S-labeled SC-K$^d$-15 in the assay of Bouillot et al. (Bouillot, M., Choppin, J., Cornille, F., Martinon, F., Papo, T., Gomard, E., Fournie-Zaluski, M. -C., and Levey, J. -P., *Nature* 1989. 339:473 and Choppin, J., Martinon, F., Gomard, E., Bahraoui, E., Connan, F., Bouillot, F., and Levy, J. -P, *J. Exp. Med.*, 1990. 172:889).

Two peptides from HIV viral proteins (env 312–327 and vpr 68–80), known to bind strongly to several MHC molecules (Choppin, J., Martinon, F., Gomard, E., Bahraoui, E., Connan, F., Bouillot, F., and Levy, J. -P, *J. Exp. Med.*, 1990. 172:889), showed significant binding to SC-K$^d$-15 as well as to the HLA-DR3 or DR213 positive control (Table 10; results shown in duplicate). In a separate experiment, the binding of SC-K$^d$-15) and that of conventional K$^d$ were compared (Table 10). As above, peptide env 312–327 was found to bind to both molecules, but three peptides known to be immunogenic (HLA-A24 170–182, HLA-Cw3 170–182 and influenza NPR- 147–158; (Maryanski, J. L., Pala, P., Cerottini, J. -C. and Corradin, G., *J. Exp. Med.* 1988. 167:1391 and Bodmer, H. C., Pemberton, R. M., Rothbard, J. B., Askonas, B. A., *Cell* 1989. 52:253), showed no detectable binding, either to the SC-K$^d$ nor to the K$^d$ molecules. In a competition experiment in which the env 312–327 peptide is bound to plastic, it was seen that the vpr 68–80 peptide competed efficiently, while the Cw3 170–182 peptide (which did not bind in the direct assay) did not. In summary, SC-K$^d$-15 bound in the HIV peptides env 312–327 and vpr 68–80 to a significant extent, albeit somewhat less efficiently than conventional K$^d$ (but the optimal conditions may be different for K$^d$ and SC-K$^d$-15 and efforts have not been made to optimize binding to SC-K$^d$-15 at this stage).

There was no detectable binding of three immunogenic peptides neither to SC-K$^d$-15 nor to K$^d$. It is possible that these peptides bind much less efficiently than the two above-described HIV peptides and that the assay, as carried out here, is not sensitive enough to detect binding. Similar observations have been made before (Choppin, J., Martinon, F., Gomard, E., Bahraoui, E., Connan, F., Bouillot, F., and Levy, J. -P, *J. Exp. Med.*, 1990. 172:889).

In conclusion, not ignoring the difficulties associated with the interpretation of such peptide binding experiments, this example demonstrates that the behavior of SC-K$^d$-15 is qualitatively similar to that of conventional K$^d$. This is clear preliminary evidence that SC-K$^d$-15 is capable of binding peptides in a manner similar to that of K$^d$.

In conclusion, this example demonstrates the engineering of single-chain K$^d$ molecules which so far display the expected properties with respect to (a) reactivity with three mAb, one of which probes proper association with β$_2$-microglobulin and another one an epitope belonging to the first domain, (b) efficient refolding upon treatment with 3 M sodium thiocyanate or 6 M urea, and (c) binding of certain peptides. Above 10 residues or so, the length of the spacer between K$^d$ heavy chain and murine β$_2$-microglobulin does not seem critical. All experiments described have been performed with trace amounts of metabolically labeled SC-K$^d$ molecules. Production in large amounts should yield material useful for peptide and TcR binding studies.

TABLE 10

Binding of peptides to purified MHC molecules[1/]

| | $^{35}$S-labeled SC-Kd | $^{125}$I-labeled HLA-DR3/DRw13 |
|---|---|---|
| (A) | | |
| Input (cpm) | 10,000 | 200000/200000 |
| nef 66–80 | 475 | 2325/1388 |
| (30 µg/ml; pH 9.6) | 397 | 1822/1290 |
| env 312–327 | 750 | 6782/19957 |
| (30 µg/ml; pH 9.6) | 712 | 3778/22637 |
| vpr 68–80 | 710 | 18582/21838 |
| (10 µg/ml, pH 5) | 621 | 18245/20593 |

[1/] Experiments were carried out in duplicate.

| | $^{35}$S-labeled SC-Kd | $^{125}$I-labeled H-2K |
|---|---|---|
| (B) | | |
| Input (cpm) | 6000 | 100000 |
| No coated peptide | 228 | 1471 |
| | 223 | 1595 |
| A24 170–182 | 284 | 1060 |
| (10 µg/ml; pH 9.6) | 229 | 1302 |
| Cw3 170–182 | 169 | 1340 |
| (10 µg/ml; pH 9.6) | 117 | 1384 |
| NPR 147–158 | 214 | 1257 |
| (10 µg/ml; pH 9.6) | 171 | 1259 |
| env 312–327 | 390 | 13772 |
| (5 µg/ml; pH 9.6) | 377 | 13764 |
| env 312–327 | 42 | 359 |
| + vpr 68–80 | 41 | 409 |
| env 312–327 | 367 | 15378 |
| + Cw3 170–182 | 375 | 15835 |

EXAMPLE II

Preparation of an HLA-β2-Microglobulin (MHC Class I) Peptide Complex

The "empty" (i.e. devoid of peptide) MHC class I molecule is produced in vast amounts in the periplasm of the *E. coli* strain harboring the recombinant plasmid. Inclusion bodies can be isolated, washed briefly in 6 M urea, and then dissolved in 8 M urea, or 6 M urea+3 M isothiocyanate. The solubilized MHC class I molecules are then mixed with a 100 fold (or more) molar excess of a peptide specifically presented by HLA-A2 or MHC class I, such as Influenza virus or HIV peptides described as optimal nonapeptides by Falk et al. (Nature (1991) 351, 290). The MHC class I peptide mixture in a dialysis bag is then dialyzed in a small volume of 6 M urea plus peptide, then 4 M urea plus peptide, then 2 M urea plus peptide, then large volumes of buffer. The MHC class I peptide complex is then purified by conventional methods (such as those described in "Protein Purification Applications", Harris E. L. V. & Angal S. (Eds.) IRL Press, Oxford, 1990).

EXAMPLE III

Immunization

For immunization, the complex is usually coupled to a protein carrier, as it is done for synthetic vaccines. Usual vaccination protocols (with several immunizations and a recall injection) should be used. The antibody response should be mainly focussed on the peptide presented by the SC-A2 molecule. In a typical experiment, mice will be injected on the base of the tail of 100 µl of complete Freund adjuvant together with 100 λ of the SC-A2 peptide complex itself coupled to a carrier such as ovalbumin of KLM. Immunization is repeated once or twice, in the following weeks. One month later, mice are boosted and the response is tested.

EXAMPLE IV

Identification and Sequencing of T-cell Region Capable of Binding HLA-A2-β2 Microglobulin The sequences disclosed by the invention in Examples I and II provide for a method of identifying the interaction responsible for the T-cell recognition of $HLA\text{-}A_2\text{-}\beta_2$-microglobulin (MHCI).

In detail, using the sequences disclosed in Examples I and II, it is possible to isolate the proteins which bind to these sequences. This is accomplished using one of the methods of purifying a protein which binds to a specific DNA sequence. Such procedures are well known in the art. Preferably, a protein which binds to a specific DNA sequence can be purified using affinity chromatography.

Specifically the amino acid sequence corresponding to the $HLA\text{-}A_2\text{-}\beta_2$-microglobulin binding domain is immobilized on an appropriate matrix, such as Sepharose, and used as an affinity matrix for the purification of the proteins which bind to the particular sequence (Arcangioli B, et al., *Eur. J. Biochem.* 179:359–364 (1989).

Preferably the DNA binding protein is extracted from human T-cells. The protein extract, obtained from the T cell is applied to a column which contains the immobilized DNA sequence of interest. Proteins which are not capable of binding to the DNA sequence are washed off the column. Proteins which bind to the DNA sequence are removed from the column using a salt gradient. The proteins eluted from such a column are enriched for the proteins which bind to the specific DNA sequences immobilized on the matrix. The DNA binding protein can then be further purified using procedures known in the art such as ion exchange chromatography, high performance liquid chromatography, and size exclusion chromatography.

During the purification of the DNA binding protein, the protein can be assayed using a gel retardation assay. (Garner, M. M. et al., *Nucl. Acid Res.* 9:3047 and Fried, M. et al., *Nucl. Acid Res.* 9:6506 (1981).

Once the DNA binding protein has been purified, a partial amino acid sequence can be obtained from the N-terminal of the protein. Alternatively, the protein can be tryptically mapped and the amino acid sequence at one of the fragments can be determined by one of the methods known in the art.

The deduced amino acid sequence can be used to generate an oligonucleotide probe. The encoding sequence can be based on codons which are known to be more frequently used by the organism. Alternatively, the probe can consist of a mixture of all the possible codon combinations which could encode the polypeptide.

A probe complementary to the amino acid sequence can be used to screen either a cDNA or genomic library for the genomic sequences which encode the DNA binding protein. Once the gene encoding the DNA binding protein has been obtained, the sequence of the DNA can be determined, the gene can be used to obtain large amounts of the protein from a recombinant host, or the sequence can be used in mutational analysis to further define the functional regions within the protein which interacts with the DNA.

Alternatively, proteins which bind to T-cell epitope can be isolated by identifying a clone expressing the protein using the technique of Southwestern blotting (Sharp, Z. D. et al., *Biochim Biophys Acta,* 1048:306–309 (1990), Gunther, C. V. et al., *Genes Dev.* 4:6657–679 (1990), and Walker, M. D. et al., *Nucleic Acids Res.* 18:1159–1166 (1990)).

In a Southwestern blot, a labeled DNA sequence is used to screen a cDNA expression library whose expressed proteins have been immobilized on a filter via colony or plaque transfer. The labeled DNA sequences will bind to colonies or plaques which express a protein capable of binding to the particular DNA sequence. Clones expressing a protein which binds to the labeled DNA sequence can be purified and the cDNA insert which encodes the DNA binding protein can be isolated sequenced. The isolated DNA can be used to express large amounts of the protein for further purification and study, used in isolating the genomic sequences corresponding to the cDNA, or used to generate functional derivative of the binding protein.

EXAMPLE V

Cell Activation Due to Recognition of the Antigenic CW3 Peptide Presented by the Altered MHC $K^d$ determinant Specific interactions between the T-cell receptor (TCR) and the peptide-MHC complex were studied using a very sensitive functional assay. The test results showed that the peptide-MHC complex formed with the altered $K^d$ is biologically functional. Further, the complex is not only capable of interacting with and being recognized by the TCR in a specific manner, but is also capable of triggering a cellular response.

The functional assay employed below was developed in light of several observations. The different chains constituting the TCR complex share a number of salient characteristics with the immunoglobulin family. Namely, they are organized into functional domains, and the domains carry out their functions independently of each other. Hence, the association of two different domains gives rise to the accumulation of the two functions. A schematic representation of the TCR α/β chains and the associated components of the CD3 complex is shown in FIG. 7.

In the case of the α/β chains of the TCR, the variable domain, Vα/Vβ, is responsible for the specific interaction with and the recognition of the peptide-MHC complex. Concerning the ξ chain of the CD3 complex, the cytoplasmic domain transduces the signal from the TCR ectodomain to the inside of the cell, where it sets off a cascade of intracellular events. The transmembrane domain on the ξ chain, on the other hand, regulates the levels of the TCR complex that reach the cell surface. Thus, in forming a complex with the TCR α and β chains, the ξ chain stabilizes the complex and permits its export to the surface.

For further discussion see, Irving et al., (1991) Cell 64, 891–901; and Romeo et al., (1991) Cell 64, 1037–1046. In addition, Letourneur et al., ((1991) PNAS, USA 88, 8905–8909) show that when the cytoplasmic domain of ξ is attached to heterologous proteins such as CD4 and CD8, the cytoplasmic domain of ξ is sufficient for inducing cell activation when the extracellular domains of CD4 or CD8 are cross-linked by antibodies against CD4 or CD8. Engel et al., ((1992) Science 256, 1318–1321) demonstrate that when the transmembrane and cytoplasmic domains of the CD3 ξ chain are attached to the extracellular domains of the TCR α and β chains, the cytoplasmic domain of ξ can induce cell activation when the α/β extracellular domains bind to the antigen-MHC determinant or are cross-linked by an antibody against the TCR.

Chimeric TCRs were constructed by attaching the transmembrane and cytoplasmic domains of the CD3 ξ chain to domains of the TCR α and β chains. As the ξ chain, when attached to heterologous proteins, induces dimerization and export of the dimer to the cell surface, the ξ chain was attached to the extracellular domains of the α and β chains as shown in FIG. 8. The nucleotide sequence for the α/β chains was derived from the TCR of a murine cytotoxic CD8+ clone (CW3/1.1) specific for an HLA CW3 peptide (amino acids 170–179). This TCR recognizes the CW3 peptide when it is presented by the MHC molecule, $K^d$ (for a complete description of this cytotoxic clone, see Pala et al. (1988) J. Immunol. 140: 871–877). The detailed sequences of the α/β chains is shown in FIGS. 9a and 9b.

All chimeras α-ξ/β-ξ were constructed by the polymerase chain reaction (PCR). PCR products were directly cloned into the expression vector pCDL-SRα296, and their sequence was confirmed by complete DNA sequencing. Construction of the chimeric protein in the expression vector pCDL-SRα296 is shown in FIG. 10.

Chimeric constructs were stably transfected into the rat basophilic leukemia line, RBL-2H3. Cells were harvested by trypsinisation and resuspended in complete media (DMEM), 10% fetal calf serum, 20 mM Hepes, 2mM glutamine, penicillin (100 U/ml), streptomycin (100 μg/ml), and gentamicin (150 μg/ml), to a concentration of $1 \times 10^7$ cells per 0.25 ml of culture media. Cells were transfected with 20 μg of Sal I-linearised DNA, consisting of 10 μg of the CW3 1.1 α and 10 μg of the CW3 1.1 β constructs; to this were added 2 μg of pfneo linearised by EcoRI, which was used to confer resistance to G418 (Geneticin, Gibco). A charge of 250 V and 450 μF was applied at room temperature with a gene electroporator, and after a 10 min recovery period the cells were put into culture. Selection with active G418 (0.5 mg/ml) was begun after 18 to 24 hours, and the concentration was increased to 1 mg/ml 2 to 4 days later.

Cell activation was induced in the transfected RBL cells and resulted in the secretion of serotonin. Transfected RBL cells that expressed the TCR α-ξ/β-ξ0 heterodimer on their cell surface were cultured for 24 hours in complete media at $4 \times 10^4$ cells/200 μl per well in 96-well flat-bottom plates (Costar) with [$^3$H]Serotonin (Dupont) at a final concentration of 2 μCi/ml (0.2 μCi per well).

For studies involving cell activation by antibody, cells were washed twice with medium and incubated for 1 hr at 37° C. with serial dilutions of monoclonal antibody (mAb) H57-197 (anti-TCR α/β) or mAb 145-2C11 (anti-CD3). Monoclonal antibodies H57-197 (anti-TCR α/β) and 145-2C11 (anti-CD3) are available from PharMingen (San Diego, Calif.) (Cat. Nos. 01301D and 01081D, respectively).

Following centrifugation, the [$^3$H]serotonin levels in the supernatant were measured by counting the radioactivity of 100 μl aliquots from each well using a Packard liquid scintillation counter.

Cell activation was also studied by incubating washed cells for 1 hr at 37° C. with serial dilutions of one of the following: (i) altered $K^d$ molecule complexed with CW3 peptide; (ii) altered $K^d$ molecule complexed with an irrelevant peptide (Y81); or (iii) altered $K^d$ molecule complexed with the SF1-1.1.1 antibody (anti-$K^d$) and either the CW3 peptide or the Y81 peptide. (The sequence of peptides CW3 and Y81 are shown in FIG. 11.) After incubating for 1 hr, the percentage of serotonin released into the culture medium was measured as described above.

When the α/β chains were cross-linked using the monoclonal antibody H57-197, which is directed against the TCR, the transfected cells secreted serotonin as shown in FIG. 12. As expected, an antibody against the CD3 complex had no effect on RBL-2H3 degranulation. However, neither soluble $K^d$ molecules loaded with the CW3 peptide nor with a peptide derived from *Plasmodium berghei* (Y81, a negative control) had an effect on cell activation (FIG. 12). This lack of effect of the soluble $K^d$ was overcome when $K^d$ was incubated with the RBL-2H3 cells in the presence of SF1-1.1.1, a monoclonal antibody specific for a region of $K^d$ that does not interfere with TCR interaction. Monoclonal antibody SF1-1.1.1 (anti-$K^d$) is available from the American Type Culture Collection (Rockville, Md.) (Cat. No. HB158). Thus, a bivalent $K^d$/SF1-1.1.1 complex, formed from the co-incubation of $K^d$ and SF1-1.1.1 at a concentration ratio of 5 to 1, was able to trigger serotonin release (FIG. 13). Furthermore, the effect is specific, since cells are activated if the $K^d$ is preloaded with CW3, but not when $K^d$ is preloaded with Y81. FIG. 14 shows the concentration dependence of the RBL-2H3 stimulation when $K^d$ and SF1-1.1.1 are co-incubated at a molar ratio of 2 to 1.

The experimental results described above demonstrate that the peptide-MHC complex formed with the single-chain $K^d$ molecule is biologically functional, in the sense that it is recognized by a TCR in the same manner as the native MHC molecule loaded with the right peptide. In addition, the recognition event retains the same specificity as expected for the TCR sequence used. Thus, the peptide/MHC complex is properly recognized when the recombinant $K^d$ protein is loaded with the CW3 peptide, but not when it is loaded with another peptide that is capable of binding to $K^d$ but which was not used for generating the specific CTL clone. Since a bivalent peptide/MHC complex was required to trigger a response of the TCR-transfected cells, any approach in which multivalent $K^d$ structures are formed, such as recombinant techniques linking the $K^d$ proteins through covalent bonds or latex beads to which monovalent $K^d$ proteins could be absorbed, would be expected to stimulate the cells in a comparable manner. Finally, the specific interaction between the CW3/$K^d$-specific TCR leads to activation of the transfected cells, presumably through the ξ chains attached to the extracellular α/β domains of the TCR. Hence, both the single-chain MHC protein and the α-ξ/β-ξ TCR heterodimer are biochemically and biologically functional in every sense of the word. The recombinant proteins described herein should therefore be useful in therapeutic strategies in which specific immune responses are required.

While this invention has been described in connection with specific embodiments thereof, it will be understood that it is capable of further modifications and this application is intended to cover variations, uses, or adaptations of the invention following, in general, the principles of the invention and including such departures from the present disclosure as come within the art to which the invention pertains and as may be applied to the essential features hereinbefore set forth as follows in the scope of the appended claims.

What is claimed is:

1. A MHC class I determinant comprising $\alpha_1$, $\alpha_2$, $\alpha_3$, and $\beta 2$-microglobulin polypeptide domains encoded by a mammalian MHC class I locus, wherein the $\alpha_3$ domain has a carboxyl terminus, and the $\beta_2$-microglobulin domain has an amino terminus covalently linked to said carboxyl terminus by a flexible peptide linker.

2. The MHC class I determinant as claimed in claim 1, wherein said mammalian MHC class I locus is an HLA locus.

3. The MHC class I determinant as claimed in claim 1, wherein said mammalian MHC class I locus is an H-2 locus.

4. The MHC class I determinant as claimed in claim 1, wherein said determinant is substantially free of contaminating peptides.

5. The MHC class I determinant as claimed in claim 1, wherein said determinant is substantially free of transmembrane and cytoplasmic regions encoded by said mammalian MHC class I locus.

6. The MHC class I determinant as claimed in claim 1, wherein said flexible peptide linker is a polypeptide spacer.

7. The MHC class I determinant as claimed in claim 6, wherein said spacer comprises about 2 to about 30 amino acids.

8. A MHC class I determinant comprising $\alpha_1$, $\alpha_2$, $\alpha_3$, and $\beta_2$-microglobulin polypeptide domains encoded by a mammalian MHC class I locus, wherein the $\alpha_3$ domain has a carboxyl terminus, and the $\beta_2$-microglobulin domain has an amino terminus covalently linked to said carboxyl terminus by a $(Gly_4 Ser)_n$ spacer, wherein n is an integer between 1 and 4.

9. The MHC class I determinant as claimed in claim 8, wherein n is 3.

10. The MHC class I determinant as claimed in claim 8, wherein said mammalian MHC class I locus is an HLA locus.

11. The MHC class I determinant as claimed in claim 8, wherein said mammalian MHC class I locus is an H-2 locus.

12. The MHC class I determinant as claimed in claim 8, wherein said determinant is substantially free of contaminating peptides.

13. The MHC class I determinant as claimed in claim 8, wherein said determinant is substantially free of transmembrane and cytoplasmic regions encoded by said mammalian MHC class I locus.

14. A MHC class I determinant comprising endogenous mammalian $\alpha_1$, $\alpha_2$, $\alpha_3$, and $\beta 2$-microglobulin polypeptide domains encoded by a mammalian MHC class I locus, wherein the $\alpha_3$ domain has a carboxyl terminus, and the $\beta_2$-microglobulin domain has an amino terminus covalently linked to said $\alpha_3$ domain carboxyl terminus by a peptide flexible linker.

15. The MHC class I determinant as claimed in claim 14, wherein said mammalian MHC class I locus is an HLA locus.

16. The MHC class I determinant as claimed in claim 14, wherein said mammalian MHC class I locus is an H-2 locus.

17. The MHC class I determinant as claimed in claim 14, wherein said determinant is substantially free of contaminating peptides.

18. The MHC class I determinant as claimed in claim 14, wherein said determinant is substantially free of transmembrane and cytoplasmic regions encoded by said mammalian MHC class I locus.

19. A recombinant DNA molecule comprising a DNA sequence encoding the MHC class I determinant of claim 1 inserted in a vector.

20. The recombinant DNA molecule as claimed in claim 19, wherein said molecule contains an expression control sequence operably linked to said DNA sequence.

21. A recombinant DNA molecule comprising a DNA sequence encoding the MHC class I determinant of claim 8 inserted in a vector.

22. The recombinant DNA molecule as claimed in claim 21, wherein said molecule contains an expression control sequence operably linked to said DNA sequence.

23. A recombinant DNA molecule comprising a DNA sequence encoding the MHC class I determinant of claim 14 inserted in a vector.

24. The recombinant DNA molecule as claimed in claim 23, wherein said molecule contains an expression control sequence operably linked to said DNA sequence.

25. A host transformed with the vector of claim 19.

26. A host transformed with the vector of claim 20.

27. A host transformed with the vector of claim 21.

28. A host transformed with the vector of claim 22.

29. A host transformed with the vector of claim 23.

30. A host transformed with the vector of claim 24.

31. A composition comprising an antigen bound to the MHC class I determinant as claimed in claim 1.

32. The composition as claimed in claim 31, wherein said antigen is a peptide.

33. The composition as claimed in claim 32, wherein said peptide is a peptide of HIV.

34. The composition as claimed in claim 33, wherein said peptide is env, gag, nef, ref, vif, or vpr of HIV.

35. A composition comprising an antigen bound to the MHC class I determinant as claimed in claim 8.

36. The composition as claimed in claim 35, wherein said antigen is a peptide.

37. The composition as claimed in claim 36, wherein said peptide is a peptide of HIV.

38. The composition as claimed in claim 37, wherein said peptide is env, gag, nef, ref, vif, or vpr of HIV.

39. A composition comprising an antigen bound to the MHC class I determinant as claimed in claim 14.

40. The composition as claimed in claim 39, wherein said antigen is a peptide.

41. The composition as claimed in claim 40, wherein said peptide is a peptide of HIV.

42. The composition as claimed in claim 41, wherein said peptide is env, gag, nef, ref, vif or vpr of HIV.

* * * * *

SEQUENCE LISTING (1) GENERAL INFORMATION:

(iii) NUMBER OF SEQUENCES: 127

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:1:

AAGCTGGGGG GGATCCAG                                                      18

(2) INFORMATION FOR SEQ ID NO:2:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:2:

Lys Leu Gly Gly Ile Gln
1              5

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

AAGCTGGGGG GGATCGGATC CGGTGGCGGC GGTTCGATCC AG                42

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:4:

Gly Gly Ile Gly Ser Gly Gly Gly Gly Ser
1               5                   10

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

AAGCTGGGGG GGATCGGATC AGGCGGATCC GGTGGCGGCG GTTCGATCCA G        51

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:6:

Gly Gly Ile Gly Ser Gly Gly Ser Gly Gly Gly Gly Ser
1               5                   10

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

AAGCTGGGGG GGATCGGATC CGGAGGCGGT GGATCCGGTG GCGGCGGTTC GATCCAG    57

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: double (D) TOPOLOGY: linear (ii) MOLECULE TYPE: peptide (xi) SEQUENCE DESCRIPTION: SEQ ID NO:8:

Gly Gly Ile Gly Ser Gly Gly Gly Ser Gly Gly Gly Ser
1               5                  10                  15

(2) INFORMATION FOR SEQ ID NO:9:

(i) SEQUENCE CHARACTERISTICS:
           (A) LENGTH: 63 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:9:

AAGCTGGGGG GGATCGGATC AGGCTCTGGA GGTGGCGGAT CCGGTGGCGG CGGTTCGATC          60

CAG                                                                         63

(2) INFORMATION FOR SEQ ID NO:10:

(i) SEQUENCE CHARACTERISTICS:
           (A) LENGTH: 17 amino acids
           (B) TYPE: amino acid
           (D) TOPOLOGY: linear (ii) MOLECULE TYPE: peptide (xi) SEQUENCE DESCRIPTION: SEQ ID NO:10:

Gly Gly Ile Gly Ser Gly Ser Gly Gly Gly Ser Gly Gly Gly Gly
1               5                  10                  15

Ser (2) INFORMATION FOR SEQ ID NO:11:

(i) SEQUENCE CHARACTERISTICS:
           (A) LENGTH: 69 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:11:

AAGCTGGGGG GGATCGGATC AGGTGGAGGA TCTGGAGGTG GCGGATCCGG TGGCGGCGGT          60

TCGATCCAG                                                                   69

(2) INFORMATION FOR SEQ ID NO:12:

(i) SEQUENCE CHARACTERISTICS:
           (A) LENGTH: 19 amino acids
           (B) TYPE: amino acid
           (D) TOPOLOGY: linear (ii) MOLECULE TYPE: peptide (xi) SEQUENCE DESCRIPTION: SEQ ID NO:12:

Gly Gly Ile Gly Ser Gly Gly Gly Ser Gly Gly Gly Ser Gly Gly
1               5                  10                  15

Gly Gly Ser (2) INFORMATION FOR SEQ ID NO:13:

(i) SEQUENCE CHARACTERISTICS:
    (A) LENGTH: 75 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:13:

AAGCTGGGGG GGATCGGATC AGGCGGAGGT GGAGGATCTG GAGGTGGCGG ATCCGGTGGC        60

GGCGGTTCGA TCCAG        75

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:14:

Gly Gly Ile Gly Ser Gly Gly Gly Gly Ser Gly Gly Gly Gly Ser
1               5                   10                  15

Gly Gly Gly Gly Ser
            20

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

GATCGGATCC GGAGGCGGTG GATCCGGTGG CGGCGGTTC        39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

GATCGAACCG CCGCCACCGG ATCCACCGCC TCCGGATCC        39

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..45
    (xi) SEQUENCE DESCRIPTION: SEQ ID NO:17:

```
GGT GGC GGT GGA TCA GGC GGT GGT GGG TCG GGT GGC GGC GGA TCC         45
Gly Gly Gly Gly Ser Gly Gly Gly Gly Ser Gly Gly Gly Gly Ser
  1               5                  10                  15
```

(2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:18:

```
Gly Gly Gly Gly Ser Gly Gly Gly Gly Ser Gly Gly Gly Gly Ser
  1               5                  10                  15
```

(2) INFORMATION FOR SEQ ID NO:19:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:19:

```
Lys Gly Ile Leu Gly Phe Val Phe Thr Leu Thr Val
  1               5                  10
```

(2) INFORMATION FOR SEQ ID NO:20:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:20:

```
Tyr Lys Gly Ile Leu Gly Phe Val Phe Thr Leu Thr Val
  1               5                  10
```

(2) INFORMATION FOR SEQ ID NO:21:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:21:

```
Thr Tyr Gln Arg Thr Arg Ala Leu Val Thr Gly
  1               5                  10
```

(2) INFORMATION FOR SEQ ID NO:22:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:22:

```
Ser Ala Ala Phe Glu Asp Leu Arg Val Leu Ser Phe Ile Arg Gly Tyr
  1               5                  10                  15
```

(2) INFORMATION FOR SEQ ID NO:23:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:23:

```
His Asn Thr Asn Gly Val Thr Ala Ala Cys Ser His Glu
 1               5                  10
```

(2) INFORMATION FOR SEQ ID NO:24:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:24:

```
Cys Pro Lys Tyr Val Lys Gln Asn Thr Leu Lys Leu Ala Thr Gly Met
 1               5                  10                  15
Arg Asn Val Pro Glu Lys Gln Thr Arg
                20                  25
```

(2) INFORMATION FOR SEQ ID NO:25:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:25:

```
Asn Thr Asp Gly Ser Thr Asp Tyr Gly Ile Leu Gln Ile Asn Ser Arg
 1               5                  10                  15
```

(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:26:

```
Leu Glu Asp Ala Arg Arg Leu Lys Ala Ile Tyr Glu Lys Lys Lys
 1               5                  10                  15
```

(2) INFORMATION FOR SEQ ID NO:27:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:27:

```
Arg Tyr Leu Glu Asn Gly Lys Glu Thr Leu Gln Arg Thr Asp Ala Pro
 1               5                  10                  15
```

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:28:

Leu Glu Thr Ser Glu Gly Cys Arg Gln Ile Leu Gly Gln Leu Gln
1            5                  10                15

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:29:

Glu Thr Ile Asn Glu Glu Ala Ala Glu Trp Asp Arg Val His Pro
1            5                  10                15

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:30:

His Ala Gly Pro Ile Ala Pro Gly Gln Met Arg Glu Pro Arg Gly
1            5                  10                15

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:31:

Lys Arg Trp Ile Ile Leu Gly Leu Asn Lys Ile Val Arg Met Tyr
1            5                  10                15

(2) INFORMATION FOR SEQ ID NO:32:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:32:

Met Gln Arg Gly Asn Phe Arg Asn Gln Arg Lys Ile Val Lys
1            5                  10

(2) INFORMATION FOR SEQ ID NO:33:

(i) SEQUENCE CHARACTERISTICS:
        (A) LENGTH: 16 amino acids (B) TYPE: amino acid
            (D) TOPOLOGY: linear (ii) MOLECULE TYPE: peptide (xi) SEQUENCE DESCRIPTION: SEQ ID NO:33:

Lys Glu Gly His Gln Met Lys Asp Cys Thr Glu Arg Gln Ala Asn Phe
1               5                   10                  15

(2) INFORMATION FOR SEQ ID NO:34:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:34:

His Glu Asp Ile Ile Ser Leu Trp Asp Gln Ser Leu Lys
1               5                   10

(2) INFORMATION FOR SEQ ID NO:35:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:35:

Ile Arg Ile Gln Arg Gly Pro Gly Arg Ala Phe Val Thr Ile Gly Lys
1               5                   10                  15

(2) INFORMATION FOR SEQ ID NO:36:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:36:

Phe Ile Asn Met Trp Gln Glu Val Gly Lys Ala Met Tyr Ala Pro Pro
1               5                   10                  15
Ile Ser (2) INFORMATION FOR SEQ ID NO:37:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:37:

Arg Pro Gly Gly Gly Asp Met Arg Asp Asn Trp Arg Ser Glu Leu Tyr
1               5                   10                  15

(2) INFORMATION FOR SEQ ID NO:38:

(i) SEQUENCE CHARACTERISTICS:
        (A) LENGTH: 12 amino acids
        (B) TYPE: amino acid
        (D) TOPOLOGY: linear

```
    (ii) MOLECULE TYPE: peptide (xi) SEQUENCE DESCRIPTION: SEQ ID NO:38:

Val Val Gln Arg Glu Lys Arg Ala Val Gly Ile Gly
1               5                   10

(2) INFORMATION FOR SEQ ID NO:39:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:39:

Arg Ile Leu Ala Val Glu Arg Tyr Leu Lys Asp Gln Gln Leu Leu Gly
1               5                   10                  15

Ile Trp Gly Cys Ser
            20

(2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:40:

Tyr Val Ala Glu Gly Thr Asp Arg Val Ile Glu Val Val Gln Gly Ala
1               5                   10                  15

Cys Arg (2) INFORMATION FOR SEQ ID NO:41:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:41:

Arg His Ile Pro Arg Arg Ile Arg Gln Gly Leu Glu Arg Ile Leu
1               5                   10                  15

(2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:42:

Val Gly Phe Pro Val Thr Pro Gln Val Pro Leu Arg Pro Met Thr
1               5                   10                  15

(2) INFORMATION FOR SEQ ID NO:43:

(i) SEQUENCE CHARACTERISTICS:
        (A) LENGTH: 16 amino acids
        (B) TYPE: amino acid
```

```
             (D) TOPOLOGY: linear (ii) MOLECULE TYPE: peptide (xi) SEQUENCE DESCRIPTION: SEQ ID NO:43:

Met Thr Tyr Lys Ala Ala Val Asp Leu Ser His Phe Leu Lys Glu Lys
1               5                  10                  15

(2) INFORMATION FOR SEQ ID NO:44:

(i) SEQUENCE CHARACTERISTICS:
             (A) LENGTH: 16 amino acids
             (B) TYPE: amino acid
             (D) TOPOLOGY: linear (ii) MOLECULE TYPE: peptide (xi) SEQUENCE DESCRIPTION: SEQ ID NO:44:

Trp Ile Tyr His Thr Gln Gly Tyr Phe Pro Asp Trp Gln Asn Tyr Thr
1               5                  10                  15

(2) INFORMATION FOR SEQ ID NO:45:

(i) SEQUENCE CHARACTERISTICS:
             (A) LENGTH: 16 amino acids
             (B) TYPE: amino acid
             (D) TOPOLOGY: linear (ii) MOLECULE TYPE: peptide (xi) SEQUENCE DESCRIPTION: SEQ ID NO:45:

Gly Val Arg Tyr Pro Leu Thr Phe Gly Trp Cys Tyr Lys Leu Val Pro
1               5                  10                  15

(2) INFORMATION FOR SEQ ID NO:46:

(i) SEQUENCE CHARACTERISTICS:
             (A) LENGTH: 9 amino acids
             (B) TYPE: amino acid
             (D) TOPOLOGY: linear (ii) MOLECULE TYPE: peptide (xi) SEQUENCE DESCRIPTION: SEQ ID NO:46:

Leu Thr Phe Gly Trp Cys Tyr Lys Leu
1               5

(2) INFORMATION FOR SEQ ID NO:47:

(i) SEQUENCE CHARACTERISTICS:
             (A) LENGTH: 15 amino acids
             (B) TYPE: amino acid
             (D) TOPOLOGY: linear (ii) MOLECULE TYPE: peptide (xi) SEQUENCE DESCRIPTION: SEQ ID NO:47:

Glu Asn Thr Ser Leu Leu His Pro Val Ser Leu His Gly Met Asp
1               5                  10                  15

(2) INFORMATION FOR SEQ ID NO:48:

(i) SEQUENCE CHARACTERISTICS:
             (A) LENGTH: 15 amino acids
             (B) TYPE: amino acid
             (D) TOPOLOGY: linear (ii) MOLECULE TYPE: peptide
```

(xi) SEQUENCE DESCRIPTION: SEQ ID NO:48:

Met Glu Asn Arg Trp Gln Val Met Ile Val Trp Gln Val Asp Arg
1               5                   10                  15

(2) INFORMATION FOR SEQ ID NO:49:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:49:

Val Lys His His Met Tyr Val Ser Gly Lys Ala Arg Gly Trp Phe Tyr
1               5                   10                  15

(2) INFORMATION FOR SEQ ID NO:50:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:50:

Ser Pro His Pro Arg Ile Ser Ser Glu Val His Ile Pro Leu Gly
1               5                   10                  15

(2) INFORMATION FOR SEQ ID NO:51:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:51:

Gly Asp Ala Arg Leu Val Ile Thr Thr Tyr Trp Gly Leu
1               5                   10

(2) INFORMATION FOR SEQ ID NO:52:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:52:

Gly Leu His Thr Gly Glu Arg Asp Trp His Leu Gly Gln Gly Val
1               5                   10                  15

(2) INFORMATION FOR SEQ ID NO:53:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:53:

Met Ala Gly Arg Ser Gly Asp Ser Asp Glu Asp Leu Leu Lys Ala Val
1               5                   10                  15

(2) INFORMATION FOR SEQ ID NO:54:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:54:

```
Leu Ile Lys Phe Leu Tyr Gln Ser Asn Pro Pro Pro Asn
1               5                   10
```

(2) INFORMATION FOR SEQ ID NO:55:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:55:

```
Ala Arg Asn Arg Arg Arg Arg Trp Arg Glu Arg Gln Arg
1               5                   10
```

(2) INFORMATION FOR SEQ ID NO:56:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:56:

```
Met Glu Gln Ala Pro Glu Asp Gln Gly Pro Gln Arg Glu Pro
1               5                   10
```

(2) INFORMATION FOR SEQ ID NO:57:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:57:

```
Ala Gly Val Ala Glu Ile Ile Arg Ile Leu Gln Gln Leu Leu
1               5                   10
```

(2) INFORMATION FOR SEQ ID NO:58:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:58:

```
Leu Phe Ile His Phe Arg Ile Gly Cys Arg His Ser Arg
1               5                   10
```

(2) INFORMATION FOR SEQ ID NO:59:

(i) SEQUENCE CHARACTERISTICS:
    (A) LENGTH: 98 amino acids
    (B) TYPE: amino acid
    (D) TOPOLOGY: linear (ii) MOLECULE TYPE: peptide (xi) SEQUENCE DESCRIPTION: SEQ ID NO:59:

```
Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
            20                  25                  30

Pro His Ile Glu Ile Gln Met Leu Lys Asn Gly Lys Lys Ile Pro Lys
            35                  40                  45

Val Glu Met Ser Asp Met Ser Phe Ser Lys Asp Trp Ser Phe Tyr Ile
50                  55                  60

Leu Ala His Thr Glu Phe Thr Pro Thr Glu Thr Asp Thr Tyr Ala Cys
65                  70                  75                  80

Arg Val Lys His Ser Met Ala Glu Pro Lys Thr Val Tyr Trp Asp Arg
                85                  90                  95

Asp Met
```

(2) INFORMATION FOR SEQ ID NO:60:

(i) SEQUENCE CHARACTERISTICS:
    (A) LENGTH: 99 amino acids
    (B) TYPE: amino acid
    (D) TOPOLOGY: linear (ii) MOLECULE TYPE: peptide (xi) SEQUENCE DESCRIPTION: SEQ ID NO:60:

```
Ile Gln Lys Thr Pro Gln Ile Gln Val Tyr Ser Arg His Pro Pro Glu
1               5                   10                  15

Asn Gly Lys Pro Asn Phe Leu Asn Cys Tyr Val Ser Gln Phe His Pro
            20                  25                  30

Pro Gln Ile Glu Ile Glu Leu Leu Lys Asn Gly Lys Lys Ile Pro Asn
            35                  40                  45

Ile Glu Met Ser Asp Leu Ser Phe Ser Lys Asp Trp Ser Phe Tyr Ile
50                  55                  60

Leu Ala His Thr Glu Phe Thr Pro Thr Glu Thr Asp Val Tyr Ala Cys
65                  70                  75                  80

Arg Val Lys His Val Thr Leu Lys Glu Pro Lys Thr Val Tyr Trp Asp
                85                  90                  95

Arg Asp Met
```

(2) INFORMATION FOR SEQ ID NO:61:

(i) SEQUENCE CHARACTERISTICS:
    (A) LENGTH: 99 amino acids
    (B) TYPE: amino acid
    (D) TOPOLOGY: linear (ii) MOLECULE TYPE: peptide (xi) SEQUENCE DESCRIPTION: SEQ ID NO:61:

```
Val His Leu Ala Pro Arg Val Gln Val Tyr Ser Arg His Pro Ala Glu
1               5                   10                  15

Asn Gly Lys Gln Asn Phe Ile Asn Cys Tyr Val Ser Gly Phe His Pro
            20                  25                  30
```

```
Pro Gln Ile Glu Val Glu Leu Leu Lys Asn Gly Lys Lys Ile Asp Asn
         35                  40                  45

Val Glu Met Ser Asp Leu Ser Phe Ser Lys Asp Trp Thr Phe Tyr Leu
 50                  55                  60

Leu Val His Ala Ala Phe Thr Pro Asn Asp Ser Asp Glu Tyr Ser Cys
 65                  70                  75                  80

Arg Val Ser His Ile Thr Leu Ser Glu Pro Lys Ile Val Lys Trp Asp
                 85                  90                  95

Pro Asn Lys (2) INFORMATION FOR SEQ ID NO:62:

(i) SEQUENCE CHARACTERISTICS:
        (A) LENGTH: 99 amino acids
        (B) TYPE: amino acid
        (D) TOPOLOGY: linear (ii) MOLECULE TYPE: peptide (xi) SEQUENCE DESCRIPTION: SEQ ID NO:62:

Val Gln Arg Ala Pro Asn Val Gln Val Tyr Ser Arg His Pro Ala Glu
 1               5                  10                  15

Asn Gly Lys Pro Asn Phe Leu Asn Cys Tyr Val Ser Gly Phe His Pro
                 20                  25                  30

Pro Gln Ile Asp Ile Glu Leu Leu Lys Asn Val Lys Lys Ile Glu Asn
         35                  40                  45

Val Glu Gln Ser Asp Leu Ser Phe Asn Lys Asp Trp Thr Phe Tyr Leu
 50                  55                  60

Leu Val His Thr Glu Phe Thr Pro Asn Asn Lys Asn Glu Tyr Ser Cys
 65                  70                  75                  80

Arg Val Lys His Val Thr Leu Lys Glu Pro Met Thr Val Lys Trp Asp
                 85                  90                  95

Arg Asp Tyr (2) INFORMATION FOR SEQ ID NO:63:

(i) SEQUENCE CHARACTERISTICS:
        (A) LENGTH: 100 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 7
        (D) OTHER INFORMATION: /note= "Xaa is an unidentifed amino
            acid residue."

(xi) SEQUENCE DESCRIPTION: SEQ ID NO:63:

Ile Gln Arg Thr Pro Lys Xaa Gln Val Tyr Ser Arg His Pro Pro Ala
 1               5                  10                  15

Asn Gly Lys Pro Ser Ile Phe Asn Cys Tyr Val Thr Ser Gly His Pro
                 20                  25                  30

Ser Asp Ile Glu Ile Val Asp Leu Leu Lys Asp Gly Glu Arg Ile Glu
         35                  40                  45

Lys Val Glu His Ser Asp Leu Ser Phe Ser Lys Asp Trp Ser Phe Tyr
 50                  55                  60

Leu Leu Tyr Tyr Thr Glu Phe Thr Pro Thr Glu Lys Asp Glu Tyr Ala
 65                  70                  75                  80
```

```
Cys Arg Val Asn His Val Thr Leu Ser Gln Pro Lys Ile Val Lys Trp
                85                  90                  95
Asp Arg Asp Met
            100

(2) INFORMATION FOR SEQ ID NO:64:

(i) SEQUENCE CHARACTERISTICS:
        (A) LENGTH: 99 amino acids
        (B) TYPE: amino acid
        (D) TOPOLOGY: linear (ii) MOLECULE TYPE: peptide (xi) SEQUENCE DESCRIPTION: SEQ ID NO:64:

Ile Gln Arg Pro Pro Lys Ile Gln Val Tyr Ser Arg His Pro Pro Glu
1               5                   10                  15

Asn Gly Lys Pro Asn Tyr Leu Asn Cys Tyr Val Tyr Gly Phe His Pro
                20                  25                  30

Pro Gln Ile Glu Ile Asp Leu Leu Lys Asn Gly Glu Lys Ile Lys Ser
            35                  40                  45

Val Glu Gln Ser Asp Leu Ser Phe Ser Lys Asp Trp Ser Phe Tyr Leu
50                  55                  60

Leu Ser His Ala Glu Phe Thr Pro Asp Ser Lys Asp Glu Tyr Ser Cys
65                  70                  75                  80

Arg Val Lys His Val Thr Leu Glu Gln Pro Arg Ile Val Tyr Trp Asp
                85                  90                  95

Arg Asp Leu (2) INFORMATION FOR SEQ ID NO:65:

(i) SEQUENCE CHARACTERISTICS:
        (A) LENGTH: 350 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 326..327
        (D) OTHER INFORMATION: /note= "Xaa is an unidentified
            amino acid residue."

(xi) SEQUENCE DESCRIPTION: SEQ ID NO:65:

Gly Pro His Ser Leu Arg Tyr Phe Val Thr Ala Val Ser Arg Pro Gly
1               5                   10                  15

Leu Gly Glu Pro Arg Tyr Met Glu Val Gly Tyr Val Asp Asp Thr Glu
                20                  25                  30

Phe Val Arg Phe Asp Ser Asp Ala Glu Asn Pro Arg Tyr Glu Pro Arg
            35                  40                  45

Ala Arg Trp Met Glu Gln Glu Gly Pro Glu Tyr Trp Glu Arg Glu Thr
50                  55                  60

Gln Lys Ala Lys Gly Asn Glu Gln Ser Phe Arg Val Asp Leu Arg Thr
65                  70                  75                  80

Leu Leu Gly Tyr Tyr Asn Gln Ser Lys Gly Gly Ser His Thr Ile Gln
                85                  90                  95

Val Ile Ser Gly Cys Glu Val Gly Ser Asp Gly Arg Leu Leu Arg Gly
                100                 105                 110

Tyr Gln Gln Tyr Ala Tyr Asp Gly Cys Asp Tyr Ile Ala Leu Met Glu
            115                 120                 125
```

```
Asp Leu Lys Thr Trp Thr Ala Ala Asp Met Ala Ala Leu Ile Thr Lys
        130                 135                 140
His Lys Trp Glu Gln Ala Gly Glu Ala Glu Arg Leu Arg Ala Tyr Leu
145                 150                 155                 160
Glu Gly Thr Cys Val Glu Trp Leu Arg Arg Tyr Leu Lys Asn Gly Asn
                165                 170                 175
Ala Thr Leu Leu Arg Thr Asp Ser Pro Lys Ala His Val Thr His His
                180                 185                 190
Ser Arg Pro Glu Asp Lys Val Thr Leu Arg Cys Trp Ala Leu Gly Phe
        195                 200                 205
Tyr Pro Ala Asp Ile Thr Leu Thr Trp Gln Leu Asn Gly Glu Glu Leu
210                 215                 220
Ile Gln Asp Met Glu Leu Val Glu Thr Arg Pro Ala Gly Asp Gly Thr
225                 230                 235                 240
Phe Gln Lys Trp Ala Ser Val Val Val Pro Leu Gly Lys Glu Gln Tyr
                245                 250                 255
Tyr Thr Cys His Val Tyr His Gln Gly Leu Pro Glu Pro Leu Thr Leu
                260                 265                 270
Arg Trp Glu Pro Pro Pro Ser Thr Val Ser Asn Met Ala Thr Val Ala
        275                 280                 285
Val Leu Val Val Leu Gly Ala Ala Ile Val Thr Gly Ala Val Val Ala
        290                 295                 300
Phe Val Met Lys Met Arg Arg Arg Asn Thr Gly Gly Lys Gly Gly Asp
305                 310                 315                 320
Tyr Ala Leu Ala Pro Xaa Xaa Gly Ser Gln Thr Ser Asp Leu Ser Leu
                325                 330                 335
Pro Asp Cys Lys Val Met Val His Asp Pro His Ser Leu Ala
                340                 345                 350

(2) INFORMATION FOR SEQ ID NO:66:

(i) SEQUENCE CHARACTERISTICS:
        (A) LENGTH: 310 amino acids
        (B) TYPE: amino acid
        (D) TOPOLOGY: linear (ii) MOLECULE TYPE: peptide (xi) SEQUENCE DESCRIPTION: SEQ ID NO:66:

Gly Pro His Ser Leu Arg Tyr Phe Val Thr Ala Val Ser Arg Pro Gly
1               5                   10                  15
Leu Gly Glu Pro Arg Phe Ile Ala Val Gly Tyr Val Asp Thr Gln Phe
                20                  25                  30
Val Arg Phe Asp Ser Asp Ala Asp Asn Pro Arg Phe Glu Pro Arg Ala
                35                  40                  45
Pro Trp Met Glu Gln Glu Gly Pro Glu Tyr Trp Glu Gln Thr Gln
        50                  55                  60
Arg Ala Lys Ser Asp Glu Gln Trp Phe Arg Val Ser Leu Arg Thr Ala
65                  70                  75                  80
Gln Arg Tyr Tyr Asn Gln Ser Lys Gly Gly Ser His Thr Phe Gln Arg
                85                  90                  95
Met Phe Gly Cys Asp Val Gly Ser Asp Trp Arg Leu Leu Arg Gly Tyr
                100                 105                 110
Gln Gln Phe Ala Tyr Asp Gly Arg Asp Tyr Ile Ala Leu Met Glu Asp
                115                 120                 125
```

```
Leu Lys Thr Trp Thr Ala Ala Asp Thr Ala Ala Leu Ile Thr Arg Arg
    130                 135                 140

Lys Trp Glu Gln Ala Gly Asp Ala Glu Tyr Tyr Arg Ala Tyr Leu Glu
145                 150                 155                 160

Gly Glu Cys Val Glu Trp Leu Arg Arg Tyr Leu Glu Leu Gly Asn Glu
                165                 170                 175

Thr Leu Leu Arg Thr Asp Ser Pro Lys Ala His Val Thr Tyr His Pro
            180                 185                 190

Arg Ser Gln Val Asp Val Thr Leu Arg Cys Trp Ala Leu Gly Phe Tyr
        195                 200                 205

Pro Ala Asp Ile Thr Leu Thr Trp Gln Leu Asn Gly Glu Asp Leu Thr
    210                 215                 220

Gln Asp Met Glu Leu Val Glu Thr Arg Pro Ala Gly Asp Gly Thr Phe
225                 230                 235                 240

Gln Lys Trp Ala Ala Val Val Pro Leu Gly Lys Glu Gln Asn Tyr
                245                 250                 255

Thr Cys His Val His His Lys Gly Leu Pro Glu Pro Leu Thr Leu Arg
            260                 265                 270

Trp Lys Leu Pro Pro Ser Thr Val Ser Asn Thr Val Ile Ile Ala Val
        275                 280                 285

Leu Val Val Leu Gly Ala Ala Ile Val Thr Gly Ala Val Val Ala Phe
    290                 295                 300

Val Met Lys Met Arg Arg
305             310

(2) INFORMATION FOR SEQ ID NO:67:

(i) SEQUENCE CHARACTERISTICS:
        (A) LENGTH: 350 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 326..327
        (D) OTHER INFORMATION: /note= "Xaa is an unidentified
            amino acid residue."

(xi) SEQUENCE DESCRIPTION: SEQ ID NO:67:

Gly Pro His Ser Leu Arg Tyr Phe His Thr Ala Val Ser Arg Pro Gly
1               5                   10                  15

Leu Gly Lys Pro Arg Phe Ile Ser Val Gly Tyr Val Asp Asp Thr Gln
            20                  25                  30

Phe Val Arg Phe Asp Ser Asp Ala Glu Asn Pro Arg Tyr Glu Pro Arg
        35                  40                  45

Val Arg Trp Met Glu Gln Val Glu Pro Glu Tyr Trp Glu Arg Met Thr
    50                  55                  60

Gln Ile Ala Lys Gly Asn Glu Gln Ile Phe Arg Val Asn Leu Arg Thr
65                  70                  75                  80

Ala Leu Arg Tyr Tyr Asn Gln Ser Ala Gly Gly Ser His Thr Phe Gln
                85                  90                  95

Arg Met Phe Tyr Cys Glu Val Gly Ser Asp Trp Arg Leu Leu Arg Gly
            100                 105                 110

Tyr Glu Gln Tyr Ala Tyr Asp Gly Cys Asp Tyr Ile Ala Leu Met Glu
        115                 120                 125

Asp Leu Lys Thr Trp Thr Ala Ala Asp Met Ala Ala Leu Ile Thr Lys
```

```
            130                 135                 140
His Lys Trp Glu Gln Ala Gly Asp Ala Glu Arg Asp Arg Ala Tyr Leu
145                 150                 155                 160

Glu Gly Thr Cys Val Glu Trp Leu Arg Arg Tyr Leu Gln Leu Gly Asn
                165                 170                 175

Ala Thr Leu Pro Arg Thr Asp Ser Pro Lys Ala His Val Thr Arg His
            180                 185                 190

Ser Arg Pro Glu Asp Lys Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Thr Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Tyr
                245                 250                 255

Tyr Thr Cys His Val Tyr His Gln Gly Leu Pro Glu Pro Leu Thr Leu
                260                 265                 270

Arg Trp Glu Pro Pro Pro Ser Thr Val Ser Asn Thr Val Ile Ile Ala
            275                 280                 285

Val Leu Val Val Leu Gly Ala Ala Ile Val Thr Gly Ala Val Val Ala
    290                 295                 300

Phe Val Met Lys Met Arg Arg Arg Asn Thr Gly Gly Lys Gly Gly Asp
305                 310                 315                 320

Tyr Ala Leu Ala Pro Xaa Xaa Gly Ser Gln Thr Ser Asp Leu Ser Leu
                325                 330                 335

Pro Asp Cys Lys Val Met Val His Asp Pro His Ser Leu Ala
            340                 345                 350

(2) INFORMATION FOR SEQ ID NO:68:

(i) SEQUENCE CHARACTERISTICS:
        (A) LENGTH: 307 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 16
        (D) OTHER INFORMATION: /note= "Xaa is an unidentified
            amino acid residue."

(ix) FEATURE:
        (A) NAME/KEY: Region
        (B) LOCATION: 18
        (D) OTHER INFORMATION: /note= "Xaa is an unidentified
            amino acid residue."

(xi) SEQUENCE DESCRIPTION: SEQ ID NO:68:

Gly Pro His Ser Leu Arg Tyr Phe His Thr Ala Val Ser Arg Pro Xaa
1               5                   10                  15

Leu Xaa Lys Pro Arg Phe Ile Ser Val Gly Tyr Val Asp Asp Thr Glu
            20                  25                  30

Phe Val Arg Phe Asp Ser Asp Ala Glu Asn Pro Arg Tyr Glu Pro Arg
        35                  40                  45

Ala Arg Trp Met Glu Gln Val Glu Pro Glu Tyr Trp Glu Arg Asn Thr
    50                  55                  60

Gln Ile Ala Lys Asp Asn Glu Gln Ser Ser Arg Val Asp Leu Arg Thr
65                  70                  75                  80
```

```
Leu Leu Arg Tyr Tyr Asn Gln Ser Ala Gly Gly Ser His Thr Ile Gln
                85                  90                  95
Arg Met Tyr Gly Cys Asp Val Gly Ser Asp Gly Arg Leu Leu Arg Gly
            100                 105                 110
Tyr Glu Gln Val Ala Tyr Asp Gly Cys Asp Tyr Ile Ala Leu Met Glu
        115                 120                 125
Asp Leu Lys Thr Trp Thr Ala Ala Asp Met Ala Ala Leu Ile Thr Lys
    130                 135                 140
His Lys Trp Glu Gln Ala Gly Ala Ala Glu Arg Arg Ala Tyr Leu
145                 150                 155                 160
Glu Gly Ala Cys Val Glu Trp Leu Ser Arg His Leu Lys Asn Gly Asn
                165                 170                 175
Ala Thr Leu Leu Arg Thr Asp Ser Pro Lys Ala His Val Thr His His
            180                 185                 190
Ser Arg Pro Glu Asp Lys Val Thr Leu Arg Cys Trp Ala Leu Gly Phe
        195                 200                 205
Tyr Pro Ala Asp Ile Thr Leu Thr Trp Gln Leu Asn Gly Glu Glu Leu
    210                 215                 220
Thr Gln Asp Met Glu Leu Val Glu Thr Arg Pro Ala Gly Asp Gly Thr
225                 230                 235                 240
Phe Gln Lys Trp Ala Ser Val Val Pro Leu Gly Lys Glu Gln Tyr
                245                 250                 255
Tyr Thr Cys His Val Tyr His Gln Gly Leu Pro Lys Pro Leu Thr Leu
            260                 265                 270
Arg Trp Glu Pro Pro Ser Ala Val Ser Asn Thr Val Ile Ile Ala
        275                 280                 285
Val Leu Val Val Leu Gly Ala Ala Ile Val Thr Gly Ala Val Val Ala
    290                 295                 300
Phe Val Met
305

(2) INFORMATION FOR SEQ ID NO:69:

(i) SEQUENCE CHARACTERISTICS:
        (A) LENGTH: 311 amino acids
        (B) TYPE: amino acid
        (D) TOPOLOGY: linear (ii) MOLECULE TYPE: peptide (xi) SEQUENCE DESCRIPTION: SEQ ID NO:69:

Gly Ser His Ser Leu Arg Tyr Phe Val Thr Ala Val Ser Arg Pro Gly
1               5                   10                  15
Phe Gly Glu Pro Arg Tyr Met Glu Val Gly Tyr Val Asp Asn Thr Glu
            20                  25                  30
Phe Val Arg Phe Asp Ser Asp Ala Glu Asn Pro Arg Tyr Glu Pro Arg
        35                  40                  45
Ala Arg Trp Ile Glu Gln Glu Gly Pro Glu Tyr Trp Glu Arg Glu Thr
    50                  55                  60
Arg Arg Ala Lys Gly Asn Glu Gln Ser Phe Arg Val Asp Leu Arg Thr
65                  70                  75                  80
Ala Leu Arg Tyr Tyr Asn Gln Ser Ala Gly Gly Ser His Thr Leu Gln
                85                  90                  95
Trp Met Ala Gly Cys Asp Val Glu Ser Asp Gly Arg Leu Leu Arg Gly
            100                 105                 110
```

```
Tyr Trp Gln Phe Ala Tyr Asp Gly Cys Asp Tyr Ile Ala Leu Met Glu
            115                 120                 125

Asp Leu Lys Thr Trp Thr Ala Ala Asp Met Ala Ala Gln Ile Thr Arg
        130                 135                 140

Arg Lys Trp Glu Gln Ala Gly Ala Ala Glu Arg Asp Arg Ala Tyr Leu
145                 150                 155                 160

Glu Gly Glu Cys Val Glu Trp Leu Arg Arg Tyr Leu Lys Asn Gly Asn
                165                 170                 175

Ala Thr Leu Leu Arg Thr Asp Pro Pro Lys Ala His Val Thr His His
            180                 185                 190

Arg Arg Pro Glu Gly Asp Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Thr Gln Glu Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Lys
                245                 250                 255

Tyr Thr Cys His Val Glu His Glu Gly Leu Pro Glu Pro Leu Thr Leu
                260                 265                 270

Arg Trp Gly Lys Glu Glu Pro Pro Ser Ser Thr Lys Thr Asn Thr Val
            275                 280                 285

Ile Ile Ala Val Pro Val Val Leu Gly Ala Val Val Ile Leu Gly Ala
        290                 295                 300

Val Met Ala Phe Val Met Lys
305                 310

(2) INFORMATION FOR SEQ ID NO:70:

(i) SEQUENCE CHARACTERISTICS:
        (A) LENGTH: 311 amino acids
        (B) TYPE: amino acid
        (D) TOPOLOGY: linear (ii) MOLECULE TYPE: peptide (xi) SEQUENCE DESCRIPTION: SEQ ID NO:70:

Gly Pro His Ser Leu Arg Tyr Phe Val Thr Ala Val Ser Arg Pro Gly
1               5                   10                  15

Leu Gly Lys Pro Arg Tyr Met Glu Val Gly Tyr Val Asp Asn Thr Glu
            20                  25                  30

Phe Val Arg Phe Asp Ser Asp Ala Glu Asn Pro Arg Met Lys Pro Arg
        35                  40                  45

Val Arg Trp Met Glu Gln Glu Gly Pro Glu Tyr Trp Glu Gln Glu Thr
    50                  55                  60

Gln Asn Ala Lys Asp His Glu Gln Ser Phe Arg Val Ser Leu Arg Thr
65                  70                  75                  80

Asn Leu Gly Tyr Tyr Asn Gln Ser Lys Gly Gly Ser His Thr Ile Gln
                85                  90                  95

Gly Met Arg Gly Cys Asp Val Gly Ser Asp Trp Arg Leu Leu Arg Gly
            100                 105                 110

Tyr Glu Gln Phe Ala Tyr Asp Gly Pro Asp Tyr Ile Ala Leu Met Glu
        115                 120                 125

Asp Leu Lys Thr Trp Thr Ala Ala Asp Met Ala Ala Gln Ile Thr Arg
    130                 135                 140

Arg Lys Trp Glu Gln Ala Gly Ala Ala Glu Thr Leu Arg Ala Tyr Leu
```

```
                145                 150                 155                 160
Glu Gly Ala Cys Val Glu Trp Leu Arg Arg Tyr Leu Glu Leu Gly Asn
                    165                 170                 175
Ala Thr Leu Leu Cys Thr Asp Pro Pro Lys Ala His Val Thr His His
                180                 185                 190
Pro Arg Ser Glu Gly Lys Val Thr Leu Arg Cys Trp Ala Leu Gly Phe
                195                 200                 205
Tyr Pro Ala Asp Ile Thr Leu Thr Trp Gln Leu Asn Gly Glu Glu Leu
            210                 215                 220
Thr Gln Asp Met Glu Leu Val Glu Thr Arg Pro Ala Gly Asp Gly Thr
225                 230                 235                 240
Phe Gln Lys Trp Ala Ala Leu Val Val Pro Leu Gly Lys Glu Gln Asn
                245                 250                 255
Tyr Thr Cys His Val Glu His Glu Gly Leu Pro Glu Pro Leu Thr Leu
                260                 265                 270
Arg Trp Glu Pro Pro Ser Thr Asp Ser Tyr Met Val Ile Val Ala
                275                 280                 285
Val Leu Val Val Leu Gly Ala Val Phe Ile Ile Gly Ala Val Val Ala
            290                 295                 300
Phe Val Met Met Met Arg Arg
305                 310

(2) INFORMATION FOR SEQ ID NO:71:

(i) SEQUENCE CHARACTERISTICS:
        (A) LENGTH: 308 amino acids
        (B) TYPE: amino acid
        (D) TOPOLOGY: linear (ii) MOLECULE TYPE: peptide (xi) SEQUENCE DESCRIPTION: SEQ ID NO:71:

Gly Pro His Ser Met Arg Tyr Phe Glu Thr Ala Val Ser Arg Pro Gly
1               5                   10                  15
Leu Glu Glu Pro Arg Tyr Ile Ser Val Gly Tyr Val Asp Asn Lys Glu
                20                  25                  30
Phe Val Arg Phe Asp Ser Asp Ala Glu Asn Pro Arg Tyr Glu Pro Arg
            35                  40                  45
Ala Pro Trp Met Glu Gln Glu Gly Pro Glu Tyr Trp Glu Arg Glu Thr
50                  55                  60
Gln Lys Ala Lys Gly Gln Gln Trp Phe Arg Val Ser Leu Arg Asn
65                  70                  75                  80
Leu Leu Gly Tyr Tyr Asn Gln Ser Ala Gly Ser His Thr Leu Gln
                85                  90                  95
Gln Met Ser Gly Cys Asp Leu Gly Ser Asp Trp Arg Leu Leu Arg Gly
                100                 105                 110
Tyr Leu Gln Phe Ala Tyr Glu Gly Arg Asp Tyr Ile Ala Leu Met Glu
            115                 120                 125
Asp Leu Lys Thr Trp Thr Ala Ala Asp Met Ala Ala Gln Ile Thr Arg
            130                 135                 140
Arg Lys Trp Glu Gln Ser Gly Ala Ala Glu His Tyr Lys Ala Tyr Leu
145                 150                 155                 160
Glu Gly Glu Cys Val Glu Trp Leu His Arg Tyr Leu Lys Asn Gly Asn
                165                 170                 175
Ala Thr Leu Leu Arg Thr Asp Ser Pro Lys Ala His Val Thr His His
                180                 185                 190
```

```
Pro Arg Ser Lys Gly Glu Val Thr Leu Arg Cys Trp Ala Leu Gly Phe
            195                 200                 205

Tyr Pro Ala Asp Ile Thr Leu Thr Trp Gln Leu Asn Gly Glu Glu Leu
            210                 215                 220

Thr Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Asn
                245                 250                 255

Tyr Thr Cys Arg Val Tyr His Glu Gly Leu Pro Glu Pro Leu Thr Leu
            260                 265                 270

Arg Trp Glu Pro Pro Ser Thr Asp Ser Tyr Met Val Ile Val Ala
            275                 280                 285

Val Leu Val Val Leu Gly Ala Met Ala Ile Ile Gly Ala Val Val Ala
            290                 295                 300

Phe Val Met Lys
305

(2) INFORMATION FOR SEQ ID NO:72:

(i) SEQUENCE CHARACTERISTICS:
        (A) LENGTH: 308 amino acids
        (B) TYPE: amino acid
        (D) TOPOLOGY: linear (ii) MOLECULE TYPE: peptide (xi) SEQUENCE DESCRIPTION: SEQ ID NO:72:

Gly Pro His Ser Met Arg Tyr Phe Glu Thr Ala Val Ser Arg Pro Gly
1               5                   10                  15

Leu Gly Glu Pro Arg Tyr Ile Ser Val Gly Tyr Val Asn Lys Thr Glu
            20                  25                  30

Phe Val Arg Phe Asp Ser Asp Ala Glu Asn Pro Arg Tyr Glu Pro Gln
            35                  40                  45

Ala Pro Trp Met Glu Gln Glu Gly Pro Glu Tyr Trp Glu Arg Ile Thr
50                  55                  60

Gln Ile Ala Lys Gly Gln Glu Gln Trp Phe Arg Val Asn Leu Arg Thr
65                  70                  75                  80

Leu Leu Gly Tyr Tyr Asn Gln Ser Ala Gly Gly Thr His Thr Leu Gln
                85                  90                  95

Trp Met Tyr Gly Cys Asp Val Ser Asp Gly Arg Leu Leu Arg Gly
            100                 105                 110

Tyr Glu Gln Phe Ala Tyr Asp Gly Arg Asp Tyr Ile Ala Leu Met Glu
            115                 120                 125

Asp Leu Lys Thr Trp Thr Ala Ala Asp Met Ala Ala Gln Ile Thr Arg
            130                 135                 140

Arg Lys Trp Glu Gln Ala Gly Ala Ala Glu Tyr Tyr Arg Ala Tyr Leu
145                 150                 155                 160

Glu Gly Glu Cys Val Glu Trp Leu His Arg Tyr Leu Lys Asn Gly Asn
                165                 170                 175

Ala Thr Leu Leu Arg Thr Asp Ser Pro Lys Ala His Val Thr His His
            180                 185                 190

Pro Arg Ser Lys Gly Glu Val Thr Leu Arg Cys Trp Ala Leu Gly Phe
            195                 200                 205

Tyr Pro Ala Asp Ile Thr Leu Thr Trp Gln Leu Asn Gly Glu Glu Leu
            210                 215                 220
```

```
Thr Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Asn
                245                 250                 255

Tyr Thr Cys Arg Val Tyr His Glu Gly Leu Pro Glu Pro Leu Thr Leu
                260                 265                 270

Arg Trp Glu Pro Pro Pro Ser Thr Asp Ser Tyr Met Val Ile Val Ala
            275                 280                 285

Val Leu Val Val Leu Gly Ala Met Ala Ile Ile Gly Ala Val Val Ala
            290                 295                 300

Phe Val Met Lys
305
```

(2) INFORMATION FOR SEQ ID NO:73:

(i) SEQUENCE CHARACTERISTICS:
        (A) LENGTH: 311 amino acids
        (B) TYPE: amino acid
        (D) TOPOLOGY: linear (ii) MOLECULE TYPE: peptide (xi) SEQUENCE DESCRIPTION: SEQ ID NO:73:

```
Gly Gln His Ser Leu Gln Tyr Phe His Thr Ala Val Ser Arg Pro Gly
1               5                   10                  15

Leu Gly Glu Pro Trp Phe Ile Ser Val Gly Tyr Val Asp Asp Thr Gln
            20                  25                  30

Phe Val Arg Phe Asp Ser Asp Ala Glu Asn Pro Arg Met Glu Pro Arg
                35                  40                  45

Ala Arg Trp Met Glu Gln Glu Gly Pro Glu Tyr Trp Glu Arg Glu Thr
50                  55                  60

Gln Met Ala Lys Gly His Glu Gln Ser Phe Arg Gly Ser Leu Arg Thr
65                  70                  75                  80

Ala Gln Ser Tyr Tyr Asn Gln Ser Lys Gly Gly Ser His Thr Leu Gln
                85                  90                  95

Trp Met Tyr Gly Cys Asp Met Gly Ser Asp Gly Arg Leu Leu Arg Gly
                100                 105                 110

Tyr Leu Gln Phe Ala Tyr Glu Gly Arg Asp Tyr Ile Ala Leu Met Glu
            115                 120                 125

Asp Leu Lys Thr Trp Thr Ala Val Asp Met Ala Ala Gln Ile Thr Arg
130                 135                 140

Arg Lys Trp Glu Gln Ala Gly Ile Ala Glu Lys Asp Gln Ala Tyr Leu
145                 150                 155                 160

Glu Gly Thr Cys Met Gln Ser Leu Arg Arg Tyr Leu Gln Leu Gly Lys
                165                 170                 175

Glu Thr Leu Leu Arg Thr Asp Pro Pro Lys Ala His Val Thr His His
            180                 185                 190

Pro Arg Ser Tyr Gly Ala Val Thr Leu Arg Cys Trp Ala Leu Gly Phe
            195                 200                 205

Tyr Pro Ala Asp Ile Thr Leu Thr Trp Gln Leu Asn Gly Glu Glu Leu
210                 215                 220

Thr Gln Asp Thr Glu Leu Val Glu Thr Arg Pro Ala Gly Val Gly Thr
225                 230                 235                 240

Phe Gln Lys Trp Ala Ser Val Val Pro Leu Gly Lys Glu Gln Asn
                245                 250                 255

Tyr Thr Cys His Val Asn His Glu Gly Leu Pro Glu Pro Leu Thr Leu
```

```
                    260                 265                 270
Arg Trp Gly Arg Trp Glu Pro Pro Tyr Thr Val Ser Asn Met Ala
            275                 280                 285
Thr Ile Ala Val Val Asp Leu Gly Ala Val Ala Ile Ile Gly Ala
        290                 295                 300
Val Val Ala Phe Val Met Asn
305                 310

(2) INFORMATION FOR SEQ ID NO:74:

(i) SEQUENCE CHARACTERISTICS:
        (A) LENGTH: 310 amino acids
        (B) TYPE: amino acid
        (D) TOPOLOGY: linear (ii) MOLECULE TYPE: peptide (xi) SEQUENCE DESCRIPTION: SEQ ID NO:74:

Gly Gln His Ser Leu Gln Tyr Phe His Thr Ala Val Ser Arg Pro Gly
1               5                  10                  15
Leu Gly Glu Pro Trp Phe Ile Ser Val Gly Tyr Val Asp Asp Thr Gln
                20                  25                  30
Phe Val Arg Phe Asp Ser Asp Ala Glu Asn Pro Arg Met Glu Pro Arg
            35                  40                  45
Ala Arg Trp Met Glu Gln Glu Gly Pro Glu Tyr Trp Glu Arg Glu Thr
        50                  55                  60
Gln Ile Ala Lys Gly His Glu Gln Ser Phe Arg Gly Ser Leu Arg Thr
65                  70                  75                  80
Ala Gln Ser Tyr Tyr Asn Gln Ser Lys Gly Gly Ser His Thr Leu Gln
                85                  90                  95
Trp Met Tyr Gly Cys Asp Met Gly Ser Asp Gly Arg Leu Leu Arg Gly
            100                 105                 110
Tyr Leu Gln Phe Ala Tyr Glu Gly Arg Asp Tyr Ile Ala Leu Met Glu
        115                 120                 125
Asp Leu Lys Thr Trp Thr Ala Val Asp Met Ala Ala Gln Ile Thr Arg
    130                 135                 140
Arg Lys Trp Glu Gln Ala Gly Ile Ala Glu Lys Asp Gln Ala Tyr Leu
145                 150                 155                 160
Glu Gly Thr Cys Met Asp Ser Leu Arg Arg Tyr Leu Gln Leu Gly Lys
                165                 170                 175
Glu Thr Leu Leu Arg Thr Asp Pro Pro Lys Ala His Val Thr His His
            180                 185                 190
Pro Arg Ser Tyr Gly Ala Val Thr Leu Arg Cys Trp Ala Leu Gly Phe
        195                 200                 205
Tyr Pro Ala Asp Ile Thr Leu Thr Trp Gln Leu Asn Gly Glu Glu Leu
    210                 215                 220
Thr Gln Asp Met Glu Leu Val Glu Thr Arg Pro Ala Gly Asp Gly Thr
225                 230                 235                 240
Phe Gln Lys Trp Ala Ser Val Val Val Pro Leu Gly Lys Glu Gln Asn
                245                 250                 255
Tyr Thr Cys His Val Asn His Glu Gly Leu Pro Glu Pro Leu Thr Leu
            260                 265                 270
Arg Trp Gly Arg Trp Glu Pro Pro Tyr Thr Val Ser Asn Met Ala
        275                 280                 285
Thr Ile Ala Val Val Val Leu Gly Ala Val Ala Ile Ile Gly Ala Val
    290                 295                 300
```

```
Val Ala Phe Val Met Asn
305             310
```

(2) INFORMATION FOR SEQ ID NO:75:

(i) SEQUENCE CHARACTERISTICS:
        (A) LENGTH: 306 amino acids
        (B) TYPE: amino acid
        (D) TOPOLOGY: linear (ii) MOLECULE TYPE: peptide (xi) SEQUENCE DESCRIPTION: SEQ ID NO:75:

```
Gly Pro His Ser Leu Arg Tyr Phe His Thr Ala Val Ser Trp Pro Gly
1               5                   10                  15

Leu Val Glu Pro Arg Phe Ile Ile Val Gly Tyr Val Asp Asp Thr Gln
            20                  25                  30

Phe Val Arg Phe Asp Ser Asp Ala Glu Asn Pro Arg Met Glu Pro Arg
        35                  40                  45

Ala Arg Trp Met Glu Gln Glu Gly Pro Glu Tyr Trp Glu Arg Glu Thr
    50                  55                  60

Gln Lys Ala Lys Gly His Glu Glu Ser Phe Arg Val Ser Leu Arg Thr
65                  70                  75                  80

Ala Gln Arg Tyr Tyr Asn Gln Ser Lys Gly Ser His Thr Leu Gln
                85                  90                  95

Trp Met Tyr Gly Cys Asp Val Gly Ser Asp Glu Arg Leu Leu Arg Gly
                100                 105                 110

Tyr Leu Gln Phe Ala Tyr Glu Gly Arg Asp Tyr Ile Ala Leu Met Glu
            115                 120                 125

Asp Leu Lys Thr Trp Thr Ala Ala Asp Met Ala Ala Gln Ile Thr Leu
    130                 135                 140

His Lys Trp Glu Gln Ala Gly Ile Ala Glu Arg Asp Asp Arg Ala Tyr
145                 150                 155                 160

Leu Glu Gly Ala Cys Val Gln Ser Leu Arg Arg Tyr Leu Gln Leu Arg
                165                 170                 175

Lys Glu Thr Leu Leu Cys Thr Asp Pro Pro Lys Ala His Val Thr His
            180                 185                 190

His Pro Arg Ser Tyr Gly Ala Val Thr Leu Arg Cys Trp Ala Leu Gly
        195                 200                 205

Phe Tyr Pro Ala Asp Ile Thr Leu Thr Trp Gln Leu Asn Gly Glu Glu
    210                 215                 220

Leu Thr Gln Asp Met Glu Leu Val Glu Thr Arg Pro Ala Gly Asp Gly
225                 230                 235                 240

Thr Phe Gln Lys Trp Ala Ser Val Val Val Pro Leu Gly Lys Glu Gln
                245                 250                 255

Asn Tyr Thr Cys His Val Asn His Glu Gly Leu Pro Glu Pro Leu Thr
            260                 265                 270

Leu Arg Trp Glu Pro Pro Pro Ser Thr Val Ser Asn Met Ala Asn Val
        275                 280                 285

Ala Ile Leu Val Val Leu Val Ala Trp Pro Ser Leu Glu Leu Trp Trp
    290                 295                 300

Ile Leu
305
```

(2) INFORMATION FOR SEQ ID NO:76:

```
    (i) SEQUENCE CHARACTERISTICS:
        (A) LENGTH: 182 amino acids
        (B) TYPE: amino acid
        (D) TOPOLOGY: linear (ii) MOLECULE TYPE: peptide (xi) SEQUENCE DESCRIPTION: SEQ ID NO:76:

Gly Gln His Ser Leu Gln Tyr Phe His Thr Ala Val Ser Arg Pro Gly
1               5                  10                  15

Leu Gly Glu Pro Trp Phe Ile Ser Val Gly Tyr Val Asp Gln Thr Gln
            20                  25                  30

Phe Val Arg Phe Asp Ser Asp Ala Glu Asn Pro Arg Met Glu Pro Arg
        35                  40                  45

Ala Arg Trp Met Glu Gln Glu Gly Pro Glu Tyr Trp Glu Arg Glu Thr
50                  55                  60

Gln Ile Ala Lys Gly His Glu Gln Ser Phe Arg Gly Ser Leu Arg Thr
65                  70                  75                  80

Ala Gln Ser Tyr Tyr Asn Gln Ser Lys Gly Gly Ser His Thr Leu Gln
                85                  90                  95

Trp Met Tyr Gly Cys Asp Met Gly Ser Asp Gly Arg Leu Leu Arg Gly
            100                 105                 110

Tyr Leu Gln Phe Ala Tyr Glu Gly Arg Asp Tyr Ile Ala Leu Asn Glu
        115                 120                 125

Asp Leu Lys Thr Trp Thr Ala Val Asp Met Ala Ala Gln Ile Thr Arg
130                 135                 140

Arg Lys Trp Glu Gln Ala Gly Ile Ala Glu Lys Asp Gln Ala Tyr Leu
145                 150                 155                 160

Glu Gly Thr Cys Met Glu Ser Leu Arg Arg Tyr Leu Gln Leu Gly Lys
                165                 170                 175

Glu Thr Leu Leu Arg Thr
            180

(2) INFORMATION FOR SEQ ID NO:77:

(i) SEQUENCE CHARACTERISTICS:
        (A) LENGTH: 301 amino acids
        (B) TYPE: amino acid
        (D) TOPOLOGY: linear (ii) MOLECULE TYPE: peptide (xi) SEQUENCE DESCRIPTION: SEQ ID NO:77:

Gly Ser His Ser Met Arg Tyr Phe Glu Thr Ser Val Ser Arg Pro Gly
1               5                  10                  15

Leu Gly Glu Pro Arg Phe Ile Ile Val Gly Tyr Val Asp Asp Thr Gln
            20                  25                  30

Phe Val Arg Phe Asp Ser Asp Ala Glu Thr Pro Arg Met Glu Pro Arg
        35                  40                  45

Ala Pro Trp Met Glu Gln Glu Gly Pro Glu Tyr Trp Glu Arg Glu Thr
50                  55                  60

Gln Arg Ala Lys Gly Asn Glu Gln Ser Phe His Val Ser Leu Arg Thr
65                  70                  75                  80

Leu Leu Gly His Tyr Asn Gln Ser Glu Ser Gly Ser His Thr Ile Gln
                85                  90                  95

Trp Met Tyr Gly Cys Lys Val Gly Ser Asp Gly Arg Phe Leu Arg Gly
            100                 105                 110

Tyr Leu Gln Tyr Ala Tyr Asp Gly Arg Asp Tyr Ile Ala Leu Met Glu
```

-continued

```
            115                 120                 125
Asp Leu Lys Thr Trp Thr Ala Ala Asp Val Ala Ala Ile Ile Thr Arg
    130                 135                 140

Arg Lys Trp Glu Gln Ala Gly Ala Ala Glu Tyr Tyr Arg Ala Tyr Leu
145                 150                 155                 160

Glu Ala Glu Cys Val Glu Trp Leu Leu Arg Tyr Leu Glu Leu Gly Lys
                165                 170                 175

Glu Thr Leu Leu Arg Thr Asp Pro Lys Thr His Val Thr His His
            180                 185                 190

Pro Gly Ser Glu Gly Asp Val Thr Leu Arg Cys Trp Pro Leu Gly Phe
                195                 200                 205

Tyr Pro Ala Asp Ile Thr Leu Thr Trp Gln Leu Asn Gly Glu Glu Leu
    210                 215                 220

Thr Gln Asp Met Glu Leu Gln Glu Thr Arg Pro Ala Gly Asp Gly Thr
225                 230                 235                 240

Phe Gln Lys Trp Ala Ser Val Val Pro Leu Gly Lys Glu Gln Asn
                245                 250                 255

Tyr Thr Cys His Val Tyr His Glu Gly Leu Pro Glu Pro Leu Thr Leu
                260                 265                 270

Arg Trp Glu Pro Pro Ser Thr Asp Ser Ile Met Ser His Ile Ala
            275                 280                 285

Asp Leu Leu Trp Pro Ser Leu Lys Leu Trp Trp Tyr Leu
                290                 295                 300
```

(2) INFORMATION FOR SEQ ID NO:78:

(i) SEQUENCE CHARACTERISTICS:
        (A) LENGTH: 308 amino acids
        (B) TYPE: amino acid
        (D) TOPOLOGY: linear (ii) MOLECULE TYPE: peptide (xi) SEQUENCE DESCRIPTION: SEQ ID NO:78:

```
Ser Pro His Ser Leu Arg Tyr Phe Thr Thr Ala Val Ser Arg Pro Gly
1               5                   10                  15

Leu Gly Glu Pro Arg Phe Ile Ile Val Gly Tyr Val Asp Asp Thr Gln
                20                  25                  30

Phe Val Arg Phe Asp Ser Asp Ala Glu Asn Pro Arg Met Glu Pro Arg
            35                  40                  45

Ala Arg Trp Ile Glu Gln Glu Gly Pro Glu Tyr Trp Glu Arg Glu Thr
    50                  55                  60

Trp Lys Ala Arg Asp Met Gly Arg Asn Phe Arg Val Asn Leu Arg Thr
65              70                  75                  80

Leu Leu Gly Tyr Tyr Asn Gln Ser Asn Asp Glu Ser His Thr Leu Gln
                85                  90                  95

Trp Met Tyr Gly Cys Asp Val Gly Pro Asp Gly Arg Leu Leu Arg Gly
                100                 105                 110

Tyr Cys Gln Glu Ala Tyr Asp Gly Gln Asp Tyr Ile Ser Leu Met Glu
            115                 120                 125

Asp Leu Arg Ser Trp Thr Ala Asn Asp Ile Ala Ser Gln Ile Ser Lys
    130                 135                 140

His Lys Ser Glu Ala Val Asp Glu Ala His Gln Gln Arg Ala Tyr Leu
145                 150                 155                 160

Gln Gly Pro Cys Val Glu Trp Leu His Arg Tyr Leu Arg Leu Gly Asn
                165                 170                 175
```

```
Glu Thr Leu Gln Arg Ser Asp Pro Pro Lys Ala His Val Thr His His
            180                 185                 190

Pro Arg Ser Glu Asp Glu Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Thr Gln Asp Met Glu Leu Val Glu Thr Arg Pro Ala Gly Asp Gly Thr
225                 230                 235                 240

Phe Gln Lys Trp Ala Ala Val Val Val Pro Leu Gly Lys Glu Gln Tyr
                245                 250                 255

Tyr Thr Cys His Val Tyr His Glu Gly Leu Pro Glu Pro Leu Thr Leu
            260                 265                 270

Arg Trp Glu Pro Pro Ser Thr Val Ser Asn Met Val Ile Ile Ala
        275                 280                 285

Val Leu Val Val Leu Gly Ala Val Ile Ile Leu Gly Ala Val Val Ala
    290                 295                 300

Phe Val Met Lys
305

(2) INFORMATION FOR SEQ ID NO:79:

(i) SEQUENCE CHARACTERISTICS:
        (A) LENGTH: 289 amino acids
        (B) TYPE: amino acid
        (D) TOPOLOGY: linear (ii) MOLECULE TYPE: peptide (xi) SEQUENCE DESCRIPTION: SEQ ID NO:79:

Gly Ser His Ser Leu Arg Tyr Phe Tyr Thr Ala Leu Ser Arg Pro Ala
1               5                   10                  15

Ile Ser Glu Pro Trp Tyr Ile Ala Val Gly Tyr Leu Asp Asp Thr Gln
            20                  25                  30

Phe Ala Arg Phe Asp Ser Ala Gly Glu Thr Gly Thr Tyr Lys Leu Ser
        35                  40                  45

Ala Pro Trp Val Glu Gln Glu Gly Pro Glu Tyr Trp Ala Arg Glu Thr
    50                  55                  60

Glu Ile Val Thr Ser Asn Ala Gln Phe Phe Arg Glu Asn Leu Gln Thr
65                  70                  75                  80

Met Leu Asp Tyr Tyr Asn Leu Ser Gln Asn Gly Ser His Thr Ile Gln
                85                  90                  95

Val Met Tyr Gly Cys Glu Val Gly Phe Phe Gly Ser Leu Phe Arg Ala
            100                 105                 110

Tyr Glu Gln His Gly Tyr Asp Gly Gln Asp Tyr Ile Ala Leu Met Glu
        115                 120                 125

Asp Leu Lys Thr Trp Thr Ala Ala Asp Met Ala Ala Glu Ile Thr Arg
    130                 135                 140

Ser Lys Trp Glu Gln Ala Gly Tyr Thr Glu Leu Arg Arg Thr Tyr Leu
145                 150                 155                 160

Glu Gly Pro Cys Lys Asp Ser Leu Leu Arg Tyr Leu Glu Asn Arg Lys
                165                 170                 175

Lys Thr Gln Glu Cys Thr Asp Pro Pro Lys Thr His Val Thr His His
            180                 185                 190

Ala Arg Pro Glu Gly Asp Val Thr Leu Arg Cys Trp Ala Leu Gly Phe
        195                 200                 205
```

```
Tyr Pro Ala His Ile Thr Leu Thr Trp Gln Leu Asn Gly Glu Glu Leu
    210                 215                 220

Ile Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Lys
                245                 250                 255

Tyr Thr Cys His Val Tyr His Glu Gly Leu Pro Glu Pro Leu Thr Leu
                260                 265                 270

Arg Trp Glu Pro Pro Ser Ser Met Pro Asn Arg Thr Thr Val Arg Ala
            275                 280                 285

Leu
```

(2) INFORMATION FOR SEQ ID NO:80:

(i) SEQUENCE CHARACTERISTICS:
        (A) LENGTH: 290 amino acids
        (B) TYPE: amino acid
        (D) TOPOLOGY: linear (ii) MOLECULE TYPE: peptide (xi) SEQUENCE DESCRIPTION: SEQ ID NO:80:

```
Gly Ser His Ser Leu Arg Tyr Phe Tyr Thr Ala Leu Ser Arg Pro Ala
1               5                   10                  15

Ile Ser Glu Pro Trp Tyr Ile Ala Val Gly Tyr Leu Asp Asp Thr Gln
                20                  25                  30

Phe Val Arg Phe Asn Ser Ser Gly Glu Thr Ala Thr Tyr Lys Leu Ser
                35                  40                  45

Ala Pro Trp Val Glu Gln Glu Gly Pro Glu Tyr Trp Ala Arg Glu Thr
50                  55                  60

Glu Ile Val Thr Ser Asn Ala Gln Phe Phe Arg Glu Asn Leu Gln Thr
65                  70                  75                  80

Met Leu Asp Tyr Tyr Asn Leu Ser Gln Asn Gly Ser His Thr Ile Gln
                85                  90                  95

Val Met Tyr Gly Cys Glu Val Glu Phe Phe Gly Ser Leu Phe Arg Ala
                100                 105                 110

Tyr Glu Gln His Gly Tyr Asp Gly Arg Asp Tyr Ile Ala Leu Met Glu
            115                 120                 125

Asp Leu Lys Thr Trp Thr Ala Ala Asp Thr Ala Ala Glu Ile Thr Arg
130                 135                 140

Ser Lys Trp Glu Gln Ala Gly Tyr Thr Glu Leu Arg Arg Thr Tyr Leu
145                 150                 155                 160

Glu Gly Pro Cys Lys Asp Ser Leu Arg Leu Tyr Leu Glu Asn Arg Lys
                165                 170                 175

Lys Thr Gln Glu Cys Thr Asp Pro Pro Lys Thr His Val Thr His His
            180                 185                 190

Pro Arg Pro Glu Gly Tyr Val Thr Leu Arg Cys Trp Ala Leu Arg Phe
            195                 200                 205

Tyr Pro Ala Asp Ile Thr Leu Thr Trp Gln Leu Asn Gly Glu Glu Leu
    210                 215                 220

Ile Gln Asp Thr Glu Leu Val Glu Thr Arg Pro Ala Gly Asp Gly Thr
225                 230                 235                 240

Phe Gln Lys Trp Ala Ala Val Val Pro Leu Gly Lys Glu Gln Lys
                245                 250                 255

Tyr Thr Cys His Val Tyr His Glu Gly Leu Pro Glu Pro Leu Thr Leu
                260                 265                 270
```

```
Arg Trp Glu Leu Pro Gln Thr Ser Met Pro Asn Arg Thr Thr Val Arg
            275                 280                 285

Ala Leu
    290

(2) INFORMATION FOR SEQ ID NO:81:

(i) SEQUENCE CHARACTERISTICS:
        (A) LENGTH: 104 amino acids
        (B) TYPE: amino acid
        (D) TOPOLOGY: linear (ii) MOLECULE TYPE: peptide (xi) SEQUENCE DESCRIPTION: SEQ ID NO:81:

Gly Ser His Ser Leu Lys Tyr Phe Tyr Thr Ala Leu Ser Arg Pro Ala
1               5                   10                  15

Ile Ser Glu Pro Trp Tyr Ile Ala Gly Gly Tyr Leu Asp Asp Thr Gln
            20                  25                  30

Phe Arg Cys Phe Glu Ser Ala Gly Glu Ser Ala Thr Tyr Lys Leu Arg
        35                  40                  45

Ala Pro Trp Val Glu Gln Glu Gly Pro Glu Tyr Trp Ala Arg Glu Thr
    50                  55                  60

Glu Ile Val Thr Ser Asn Ala Gln Phe Phe Arg Val Glu Asn Leu Gln
65                  70                  75                  80

Thr Met Leu Asp Tyr Tyr Ser Leu Ser Gln Asn Gly Ser His Thr Ile
                85                  90                  95

Gln Val Met Tyr Gly Cys Glu Val
            100

(2) INFORMATION FOR SEQ ID NO:82:

(i) SEQUENCE CHARACTERISTICS:
        (A) LENGTH: 108 amino acids
        (B) TYPE: amino acid
        (D) TOPOLOGY: linear (ii) MOLECULE TYPE: peptide (xi) SEQUENCE DESCRIPTION: SEQ ID NO:82:

Asp Pro Pro Lys Thr His Val Thr His His Pro Arg Pro Glu Gly Tyr
1               5                   10                  15

Val Thr Leu Arg Cys Trp Ala Leu Arg Phe Tyr Pro Ala Asp Ile Thr
            20                  25                  30

Leu Thr Trp Gln Leu Asn Gly Glu Glu Leu Ile Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Leu Gly Lys Glu Gln Lys Tyr Thr Cys His Val Tyr
65                  70                  75                  80

His Glu Gly Leu Pro Glu Pro Leu Thr Leu Arg Trp Glu Leu Pro Gln
                85                  90                  95

Thr Ser Met Pro Asn Arg Thr Thr Val Arg Ala Leu
            100                 105

(2) INFORMATION FOR SEQ ID NO:83:

(i) SEQUENCE CHARACTERISTICS:
        (A) LENGTH: 184 amino acids
        (B) TYPE: amino acid
```

(D) TOPOLOGY: linear (ii) MOLECULE TYPE: peptide (xi) SEQUENCE DESCRIPTION: SEQ ID NO:83:

Gly Ser Leu Phe Arg Ala Tyr Glu Gln His Gly Tyr Asp Gly Arg Asp
1               5                   10                  15

Tyr Ile Ala Leu Met Glu Asp Val Lys Thr Trp Thr Ala Ala Asp Met
            20                  25                  30

Ala Ala Glu Ile Thr Arg Ser Lys Trp Glu Gln Ala Gly Tyr Thr Glu
        35                  40                  45

Leu Arg Arg Thr Tyr Leu Glu Gly Pro Cys Lys Asp Ser Leu Leu Arg
    50                  55                  60

Tyr Leu Glu Asn Arg Lys Lys Gln Glu Cys Thr Asp Pro Pro Lys Thr
65                  70                  75                  80

Ala His Val Thr His His Pro Arg Pro Glu Gly Tyr Val Thr Leu Arg
                85                  90                  95

Cys Trp Ala Leu Gly Phe Tyr Pro Ala Asp Ile Thr Leu Thr Trp Gln
            100                 105                 110

Leu Asn Gly Glu Glu Leu Ile Gln Asp Met Glu Leu Val Glu Thr Arg
        115                 120                 125

Pro Ala Gly Asp Gly Thr Phe Gln Lys Trp Ala Ala Val Val Val Pro
    130                 135                 140

Ser Gly Glu Glu Gln Lys Tyr Thr Cys His Val Tyr His Glu Gly Leu
145                 150                 155                 160

Pro Glu Pro Leu Thr Leu Arg Trp Glu Pro Pro Gln Ser Ser Met Pro
                165                 170                 175

Thr Arg Thr Ile Val Arg Ala Leu
            180

(2) INFORMATION FOR SEQ ID NO:84:

(i) SEQUENCE CHARACTERISTICS:
        (A) LENGTH: 92 amino acids
        (B) TYPE: amino acid
        (D) TOPOLOGY: linear (ii) MOLECULE TYPE: peptide (xi) SEQUENCE DESCRIPTION: SEQ ID NO:84:

Val Thr Leu Arg Cys Trp Ala Leu Gly Phe Tyr Pro Ala Asp Ile Thr
1               5                   10                  15

Leu Thr Trp Gln Leu Asn Gly Glu Glu Leu Ile Gln Asp Thr Glu Leu
            20                  25                  30

Val Glu Thr Arg Pro Ala Gly Asp Gly Thr Phe Gln Lys Trp Ala Ala
        35                  40                  45

Leu Val Val Pro Ser Gly Glu Glu Gln Lys Tyr Thr Cys His Val Tyr
    50                  55                  60

His Lys Gly Leu Pro Glu Pro Leu Thr Leu Arg Trp Glu Pro Pro Gln
65                  70                  75                  80

Ser Ser Met Pro Asn Arg Thr Thr Val Arg Ala Leu
                85                  90

(2) INFORMATION FOR SEQ ID NO:85:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (ix) FEATURE:
            (A) NAME/KEY: Region
            (B) LOCATION: 14..15
            (D) OTHER INFORMATION: /note= "Xaa is an unidentified
                amino acid residue."

(xi) SEQUENCE DESCRIPTION: SEQ ID NO:85:

Asn Thr Gly Gly Lys Gly Val Asn Tyr Ala Leu Ala Pro Xaa Xaa Gly
1               5                   10                  15

Ser Gln Thr Ser Asp Leu Ser Leu Pro Asp Gly Lys Val Met Val His
                20                  25                  30

Asp Pro His Ser Leu Ala
            35

(2) INFORMATION FOR SEQ ID NO:86:

(i) SEQUENCE CHARACTERISTICS:
            (A) LENGTH: 42 amino acids
            (B) TYPE: amino acid
            (D) TOPOLOGY: linear (ii) MOLECULE TYPE: peptide (ix) FEATURE:
            (A) NAME/KEY: Region
            (B) LOCATION: 18..19
            (D) OTHER INFORMATION: /note= "Xaa is an unidentified
                amino acid residue."

(xi) SEQUENCE DESCRIPTION: SEQ ID NO:86:

Met Arg Arg Arg Asn Thr Gly Gly Lys Gly Gly Asp Tyr Ala Leu Ala
1               5                   10                  15

Pro Xaa Xaa Gly Ser Gln Thr Ser Asp Leu Ser Leu Pro Asp Cys Lys
                20                  25                  30

Val Met Val His Asp Pro His Ser Leu Ala
            35                  40

(2) INFORMATION FOR SEQ ID NO:87:

(i) SEQUENCE CHARACTERISTICS:
            (A) LENGTH: 32 amino acids
            (B) TYPE: amino acid
            (D) TOPOLOGY: linear (ii) MOLECULE TYPE: peptide (ix) FEATURE:
            (A) NAME/KEY: Region
            (B) LOCATION: 17..18
            (D) OTHER INFORMATION: /note= "Xaa is an unidentified
                amino acid residue."

(xi) SEQUENCE DESCRIPTION: SEQ ID NO:87:

Arg Arg Arg Asn Thr Gly Gly Lys Gly Gly Asp Tyr Ala Leu Ala Pro
1               5                   10                  15

Xaa Xaa Gly Ser Gln Ser Ser Asp Met Ser Leu Pro Asp Cys Lys Val
                20                  25                  30

(2) INFORMATION FOR SEQ ID NO:88:

(i) SEQUENCE CHARACTERISTICS:
            (A) LENGTH: 29 amino acids
            (B) TYPE: amino acid
            (D) TOPOLOGY: linear

```
        (ii) MOLECULE TYPE: peptide (ix) FEATURE:
             (A) NAME/KEY: Region
             (B) LOCATION: 14..15
             (D) OTHER INFORMATION: /note= "Xaa is an unidentified
                 amino acid residue."

(xi) SEQUENCE DESCRIPTION: SEQ ID NO:88:

Asn Thr Gly Gly Lys Gly Gly Asp Tyr Thr Leu Ala Pro Xaa Xaa Gly
1               5                   10                  15

Ser Gln Ser Ser Glu Met Ser Leu Arg Asp Cys Lys Ala
            20                  25

(2) INFORMATION FOR SEQ ID NO:89:

(i) SEQUENCE CHARACTERISTICS:
             (A) LENGTH: 32 amino acids
             (B) TYPE: amino acid
             (D) TOPOLOGY: linear (ii) MOLECULE TYPE: peptide (ix) FEATURE:
             (A) NAME/KEY: Region
             (B) LOCATION: 17..18
             (D) OTHER INFORMATION: /note= "Xaa is an unidentified
                 amino acid residue."

(xi) SEQUENCE DESCRIPTION: SEQ ID NO:89:

Arg Arg Arg Asn Thr Gly Gly Lys Gly Gly Asp Tyr Ala Leu Ala Pro
1               5                   10                  15

Xaa Xaa Gly Ser Gln Ser Ser Glu Met Ser Leu Arg Asp Cys Lys Ala
            20                  25                  30

(2) INFORMATION FOR SEQ ID NO:90:

(i) SEQUENCE CHARACTERISTICS:
             (A) LENGTH: 10 amino acids
             (B) TYPE: amino acid
             (D) TOPOLOGY: linear (ii) MOLECULE TYPE: peptide (xi) SEQUENCE DESCRIPTION: SEQ ID NO:90:

Arg Arg Arg His Ile Gly Val Lys Gly Cys
1               5                   10

(2) INFORMATION FOR SEQ ID NO:91:

(i) SEQUENCE CHARACTERISTICS:
             (A) LENGTH: 21 amino acids
             (B) TYPE: amino acid
             (D) TOPOLOGY: linear (ii) MOLECULE TYPE: peptide (ix) FEATURE:
             (A) NAME/KEY: Region
             (B) LOCATION: 6..7
             (D) OTHER INFORMATION: /note= "Xaa is an unidentified
                 amino acid residue."

(xi) SEQUENCE DESCRIPTION: SEQ ID NO:91:

Tyr Ala His Val Leu Xaa Xaa Gly Ser Lys Ser Phe Gln Thr Ser Asp
1               5                   10                  15

Trp Pro Gln Lys Ala
            20
```

(2) INFORMATION FOR SEQ ID NO:92:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 34..35
        (D) OTHER INFORMATION: /note= "Xaa is an unidentified
            amino acid residue."

(xi) SEQUENCE DESCRIPTION: SEQ ID NO:92:

Leu Gly Ala Met Ile Ile Leu Gly Phe Met Ser Gly Ser Val Met Met
1               5                   10                  15

Trp Met Arg Lys Asn Asn Gly Gly Asn Gly Asp Asp Asn Thr Ala Ala
            20                  25                  30

Tyr Xaa Xaa Gln Met Glu Arg Glu His Leu Ser Leu Trp Ser Gln
        35                  40                  45

(2) INFORMATION FOR SEQ ID NO:93:

(i) SEQUENCE CHARACTERISTICS:
        (A) LENGTH: 70 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 34..35
        (D) OTHER INFORMATION: /note= "Xaa is an unidentified
            amino acid residue."

(xi) SEQUENCE DESCRIPTION: SEQ ID NO:93:

Leu Gly Ala Met Ile Ile Leu Gly Phe Met Ser Gly Ser Val Met Met
1               5                   10                  15

Trp Met Arg Lys Asn Asn Gly Gly Asn Gly Asp Asp Asn Thr Ala Ala
            20                  25                  30

Tyr Xaa Xaa Gln Asn Glu Arg Glu His Leu Ser Leu Thr Pro Arg Ala
        35                  40                  45

Glu Ser Glu Ala Leu Gly Val Glu Ala Gly Met Lys Asp Leu Pro Ser
    50                  55                  60

Ala Pro Pro Leu Val Ser
65                  70

(2) INFORMATION FOR SEQ ID NO:94:

(i) SEQUENCE CHARACTERISTICS:
        (A) LENGTH: 70 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 34..35
        (D) OTHER INFORMATION: /note= "Xaa is an unidentified
            amino acid residue."

(xi) SEQUENCE DESCRIPTION: SEQ ID NO:94:

Leu Gly Ala Met Ile Ile Leu Gly Phe Met Ser Gly Gly Val Met Met

```
1               5                   10                  15
Trp Met Arg Lys Asn Asn Gly Gly Asn Gly Asp Asp Asn Thr Ala Ala
            20                  25                  30

Cys Xaa Xaa Gln Met Glu Arg Glu His Leu Ser Leu Ser Pro Arg Ala
            35                  40                  45

Glu Ser Glu Ala Leu Gly Val Glu Ala Gly Met Lys Asp Leu Pro Ser
            50                  55                  60

Ala Pro Pro Leu Val Ser
65                  70
```

(2) INFORMATION FOR SEQ ID NO:95:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 34..35
        (D) OTHER INFORMATION: /note= "Xaa is an unidentified
            amino acid residue."

(xi) SEQUENCE DESCRIPTION: SEQ ID NO:95:

```
Leu Gly Ala Met Ile Ile Leu Gly Ile Met Ser Gly Ser Val Met Met
1               5                   10                  15

Trp Met Arg Lys Asn Lys Gly Gly Asn Gly Gln Asp Asn Thr Ala Ala
            20                  25                  30

Cys Xaa Xaa Gln Met Glu Arg Glu His Leu Ser Leu Ser Pro Arg Ala
            35                  40                  45

Glu Ser Glu Ala Leu Gly Val Glu Ala Gly Leu Lys Asp Leu Pro Ser
            50                  55                  60
```

(2) INFORMATION FOR SEQ ID NO:96:

(i) SEQUENCE CHARACTERISTICS:
        (A) LENGTH: 70 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 34..35
        (D) OTHER INFORMATION: /note= "Xaa is an unidentified
            amino acid residue."

(xi) SEQUENCE DESCRIPTION: SEQ ID NO:96:

```
Leu Gly Ala Met Val Ile Leu Gly Val Met Arg Gly Ser Gly Met Met
1               5                   10                  15

Trp Met Arg Lys Asn Lys Gly Gly Asn Arg Asp Asp Asn Thr Ala Ala
            20                  25                  30

Cys Xaa Xaa Gln Met Glu Arg Glu His Leu Ser Leu Ser Ala Gly Asp
            35                  40                  45

Glu Ser Asp Ala Leu Gly Val Glu Ala Gly Leu Lys Glu Leu Pro Thr
            50                  55                  60

Ala Pro Pro Leu Val Pro
65                  70
```

(2) INFORMATION FOR SEQ ID NO:97:

(i) SEQUENCE CHARACTERISTICS:
    (A) LENGTH: 365 amino acids
    (B) TYPE: amino acid
    (D) TOPOLOGY: linear (ii) MOLECULE TYPE: peptide (xi) SEQUENCE DESCRIPTION: SEQ ID NO:97:

```
Met Ala Val Met Ala Pro Arg Thr Leu Val Leu Leu Leu Ser Gly Ala
-24             -20                 -15                 -10

Leu Ala Leu Thr Gln Thr Trp Ala Gly Ser His Ser Met Arg Tyr Phe
         -5                   1                   5

Phe Thr Ser Val Ser Arg Pro Gly Arg Gly Glu Pro Arg Phe Ile Ala
         10                  15                  20

Val Gly Tyr Val Asp Asp Thr Gln Phe Val Arg Phe Asp Ser Asp Ala
 25                  30                  35                  40

Ala Ser Gln Arg Met Glu Pro Arg Ala Pro Trp Ile Glu Gln Glu Gly
             45                  50                  55

Pro Glu Tyr Trp Asp Gly Glu Thr Arg Lys Val Lys Ala His Ser Gln
             60                  65                  70

Thr His Arg Val Asp Leu Ser Thr Leu Arg Gly Tyr Tyr Asn Gln Ser
         75                  80                  85

Glu Ala Gly Ser His Thr Val Gln Arg Met Tyr Gly Cys Asp Val Gly
 90                  95                  100

Ser Asp Trp Arg Phe Leu Arg Gly Tyr His Gln Tyr Ala Tyr Asp Gly
105                 110                 115                 120

Lys Asp Tyr Ile Ala Leu Lys Glu Asp Leu Arg Ser Trp Thr Ala Ala
             125                 130                 135

Asp Met Ala Ala Gln Thr Thr Lys His Lys Trp Glu Ala Ala His Val
             140                 145                 150

Ala Glu Gln Leu Arg Ala Tyr Leu Glu Gly Thr Cys Val Glu Trp Leu
         155                 160                 165

Arg Arg Tyr Leu Glu Asn Gly Lys Glu Thr Leu Gln Arg Thr Asp Ala
170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
             205                 210                 215

Trp Gln Arg Asp Gly Glu Asp Gln Thr Gln Asp Thr Glu Leu Val Glu
             220                 225                 230

Thr Arg Pro Ala Gly Asp Gly Thr Phe Gln Lys Trp Ala Ala Val Val
         235                 240                 245

Val Pro Ser Gly Gln Glu Gln Arg Tyr Thr Cys His Val Gln His Glu
         250                 255                 260

Gly Leu Pro Lys Pro Leu Thr Leu Pro Trp Glu Pro Ser Ser Gln Pro
265                 270                 275                 280

Thr Ile Pro Ile Val Gly Ile Ile Ala Gly Leu Val Leu Phe Gly Ala
             285                 290                 295

Val Ile Thr Gly Ala Val Val Ala Ala Val Met Trp Arg Arg Lys Ser
             300                 305                 310

Ser Asp Arg Lys Gly Gly Ser Tyr Ser Gln Ala Ala Ser Ser Asp Ser
         315                 320                 325

Ala Gln Gly Ser Asp Val Ser Leu Thr Ala Cys Lys Val
330                 335                 340
```

(2) INFORMATION FOR SEQ ID NO:98:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:98:

```
Met Ala Val Met Ala Pro Arg Thr Leu Val Leu Leu Ser Gly Ala
-24             -20                 -15                 -10

Leu Ala Leu Thr Gln Thr Trp Ala Gly Ser His Ser Met Arg Tyr Phe
         -5                   1                   5

Tyr Thr Ser Val Ser Arg Pro Gly Arg Gly Glu Pro Arg Phe Ile Ala
         10                  15                  20

Val Gly Tyr Val Asp Asp Thr Gln Phe Val Arg Phe Asp Ser Asp Ala
 25                  30                  35                  40

Ala Ser Gln Arg Met Glu Pro Arg Ala Pro Trp Ile Glu Gln Glu Gly
                 45                  50                  55

Pro Glu Tyr Trp Asp Gly Glu Thr Arg Lys Val Lys Ala His Ser Gln
                 60                  65                  70

Thr His Arg Val Asp Leu Ser Thr Leu Arg Gly Tyr Tyr Asn Gln Ser
             75                  80                  85

Glu Ala Gly Ser His Thr Val Gln Arg Met Tyr Gly Cys Asp Val Gly
     90                  95                  100

Ser Asp Trp Arg Phe Leu Arg Gly Tyr His Gln Tyr Ala Tyr Asp Gly
105                 110                 115                 120

Lys Asp Tyr Ile Ala Leu Lys Glu Asp Leu Arg Ser Trp Thr Ala Ala
                 125                 130                 135

Asp Met Ala Ala Gln Thr Thr Lys His Lys Trp Glu Ala Ala His Val
             140                 145                 150

Ala Glu Gln Leu Arg Ala Tyr Leu Glu Gly Thr Cys Val Glu Trp Leu
             155                 160                 165

Arg Arg Tyr Leu Glu Asn Gly Lys Glu Thr Leu Gln Arg Thr Asp Ala
         170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
                 205                 210                 215

Trp Gln Arg Asp Gly Glu Asp Gln Thr Gln Asp Thr Glu Leu Val Glu
             220                 225                 230

Thr Arg Pro Ala Gly Asp Gly Thr Phe Gln Lys Trp Ala Ala Val Val
         235                 240                 245

Val Pro Ser Gly Gln Glu Gln Arg Tyr Thr Cys His Val Gln His Glu
 250                 255                 260

Gly Leu Pro Lys Pro Leu Thr Leu Pro Trp Glu Pro Ser Ser Gln Pro
265                 270                 275                 280

Thr Ile Pro Ile Val Gly Ile Ile Ala Gly Leu Val Leu Phe Gly Ala
             285                 290                 295

Val Ile Thr Gly Ala Val Val Ala Ala Val Met Trp Arg Arg Lys Ser
         300                 305                 310

Ser Asp Arg Lys Gly Gly Ser Tyr Ser Gln Ala Ala Ser Ser Asp Ser
         315                 320                 325

Ala Gln Gly Ser Asp Val Ser Leu Thr Ala Cys Lys Val
```

330        335        340

(2) INFORMATION FOR SEQ ID NO:99:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:99:

```
Met Ala Val Met Ala Pro Arg Thr Leu Val Leu Leu Leu Ser Gly Ala
-24             -20             -15             -10

Leu Ala Leu Thr Gln Thr Trp Ala Gly Ser His Ser Met Arg Tyr Phe
         -5               1               5

Phe Thr Ser Val Ser Arg Pro Gly Arg Gly Glu Pro Arg Phe Ile Ala
         10              15              20

Val Gly Tyr Val Asp Asp Thr Gln Phe Val Arg Phe Asp Ser Asp Ala
 25              30              35              40

Ala Ser Gln Arg Met Glu Pro Arg Ala Pro Trp Ile Glu Gln Glu Gly
             45              50              55

Pro Glu Tyr Trp Asp Gly Glu Thr Arg Lys Val Lys Ala His Ser Gln
             60              65              70

Thr His Arg Val Asp Leu Ser Thr Leu Arg Gly Tyr Tyr Asn Gln Ser
             75              80              85

Glu Ala Gly Ser His Thr Val Gln Arg Met Tyr Gly Cys Asp Val Gly
 90              95             100

Ser Asp Gly Arg Phe Leu Arg Gly Tyr His Gln Tyr Ala Tyr Asp Gly
105             110             115             120

Lys Asp Tyr Ile Ala Leu Lys Glu Asp Leu Arg Ser Trp Thr Ala Ala
             125             130             135

Asp Met Ala Ala Gln Thr Thr Lys His Lys Trp Glu Thr Ala His Glu
             140             145             150

Ala Glu Gln Trp Arg Ala Tyr Leu Glu Gly Thr Cys Val Glu Trp Leu
             155             160             165

Arg Arg Tyr Leu Glu Asn Gly Lys Glu Thr Leu Gln Arg Thr Asp Ala
170             175             180

Pro Lys Thr His Met Thr His His Ala Val Ser Asp His Glu Ala Thr
185             190             195             200

Leu Arg Cys Trp Ala Leu Ser Phe Tyr Pro Ala Glu Ile Thr Leu Thr
             205             210             215

Trp Gln Arg Asp Gly Glu Asp Gln Thr Gln Asp Thr Glu Leu Val Glu
             220             225             230

Thr Arg Pro Ala Gly Asp Gly Thr Phe Gln Lys Trp Ala Ala Val Val
             235             240             245

Val Pro Ser Gly Gln Glu Gln Arg Tyr Thr Cys His Val Gln His Glu
250             255             260

Gly Leu Pro Lys Pro Leu Thr Leu Pro Trp Glu Pro Ser Ser Gln Pro
265             270             275             280

Thr Ile Pro Ile Val Gly Ile Ile Ala Gly Leu Val Leu Phe Gly Ala
             285             290             295

Val Ile Thr Gly Ala Val Val Ala Ala Val Met Trp Arg Arg Lys Ser
             300             305             310

Ser Asp Arg Lys Gly Gly Ser Tyr Ser Gln Ala Ala Ser Ser Asp Ser
315             320             325
```

```
Ala Gln Gly Ser Asp Val Ser Leu Thr Ala Cys Lys Val
    330             335                 340
```

(2) INFORMATION FOR SEQ ID NO:100:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:100:

```
Met Ala Val Met Ala Pro Arg Thr Leu Val Leu Leu Ser Gly Ala
-24             -20                 -15             -10

Leu Ala Leu Thr Gln Thr Trp Ala Gly Ser His Ser Met Arg Tyr Phe
             -5              1              5

Tyr Thr Ser Val Ser Arg Pro Gly Arg Gly Glu Pro Arg Phe Ile Ala
    10              15              20

Val Gly Tyr Val Asp Asp Thr Gln Phe Val Arg Phe Asp Ser Asp Ala
25              30              35                      40

Ala Ser Gln Arg Met Glu Pro Arg Ala Pro Trp Ile Glu Gln Glu Gly
            45              50              55

Pro Glu Tyr Trp Asp Gly Glu Thr Arg Lys Val Lys Ala His Ser Gln
            60              65              70

Thr His Arg Val Asp Leu Ser Thr Leu Arg Gly Tyr Tyr Asn Gln Ser
            75              80              85

Glu Ala Gly Ser His Thr Val Gln Arg Met Phe Gly Cys Asp Val Gly
90              95                      100

Ser Asp Gly Arg Phe Leu Arg Gly Tyr His Gln Tyr Ala Tyr Asp Gly
105             110             115                     120

Lys Asp Tyr Ile Ala Leu Lys Glu Asp Leu Arg Ser Trp Thr Ala Ala
                125             130             135

Asp Met Ala Ala Gln Thr Thr Lys His Lys Trp Glu Ala Ala His Val
            140             145             150

Ala Glu Gln Leu Arg Ala Tyr Leu Glu Gly Thr Cys Val Glu Trp Leu
            155             160             165

Arg Arg Tyr Leu Glu Asn Gly Lys Glu Thr Leu Gln Arg Thr Asp Ala
    170             175             180

Pro Lys Thr His Met Thr His His Ala Val Ser Asp His Glu Ala Thr
185             190             195                     200

Leu Arg Cys Trp Ala Leu Ser Phe Tyr Pro Ala Glu Ile Thr Leu Thr
            205             210             215

Trp Gln Arg Asp Gly Glu Asp Gln Thr Gln Asp Thr Glu Leu Val Glu
            220             225             230

Thr Arg Pro Ala Gly Asp Gly Thr Phe Gln Lys Trp Ala Ala Val Val
            235             240             245

Val Pro Ser Gly Gln Glu Gln Arg Tyr Thr Cys His Val Gln His Glu
    250             255             260

Gly Leu Pro Lys Pro Leu Thr Leu Pro Trp Glu Pro Ser Ser Gln Pro
265             270             275             280

Thr Ile Pro Ile Val Gly Ile Ile Ala Gly Leu Val Leu Phe Gly Ala
            285             290             295

Val Ile Thr Gly Ala Val Val Ala Val Met Trp Arg Arg Lys Ser
            300             305             310
```

Ser Asp Arg Lys Gly Gly Ser Tyr Ser Gln Ala Ala Ser Ser Asp Ser
            315                 320                 325

Ala Gln Gly Ser Asp Val Ser Leu Thr Ala Cys Lys Val
            330                 335                 340

(2) INFORMATION FOR SEQ ID NO:101:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:101:

Met Ala Val Met Ala Pro Arg Thr Leu Val Leu Leu Leu Ser Gly Ala
-24                 -20                 -15                 -10

Leu Ala Leu Thr Gln Thr Trp Ala Gly Ser His Ser Met Arg Tyr Phe
            -5                  1                   5

Tyr Thr Ser Val Ser Arg Pro Gly Arg Gly Glu Pro Arg Phe Ile Ala
            10                  15                  20

Val Gly Tyr Val Asp Asp Thr Gln Phe Val Arg Phe Asp Ser Asp Ala
25                  30                  35                  40

Ala Ser Arg Arg Met Glu Pro Arg Ala Pro Trp Ile Glu Gln Glu Gly
            45                  50                  55

Pro Glu Tyr Trp Asp Gly Glu Thr Arg Lys Val Lys Ala His Ser Gln
            60                  65                  70

Thr His Arg Val Asp Leu Ser Thr Leu Arg Gly Tyr Tyr Asn Gln Ser
            75                  80                  85

Glu Ala Gly Ser His Leu Val Gln Arg Met Tyr Gly Cys Asp Val Gly
            90                  95                  100

Phe Asp Trp Arg Phe Leu Arg Gly Tyr His Gln Tyr Ala Tyr Asp Gly
105                 110                 115                 120

Lys Asp Tyr Ile Ala Leu Lys Glu Asp Leu Arg Ser Trp Thr Ala Ala
            125                 130                 135

Asp Met Ala Ala Gln Thr Thr Lys His Lys Trp Glu Thr Ala His Val
            140                 145                 150

Ala Glu Gln Leu Arg Ala Tyr Leu Glu Gly Thr Cys Val Glu Trp Leu
            155                 160                 165

Arg Arg Tyr Leu Glu Asn Gly Lys Glu Thr Leu Gln Arg Thr Asp Ala
            170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
            205                 210                 215

Trp Gln Arg Asp Gly Glu Asp Gln Thr Gln Asp Thr Glu Leu Val Glu
            220                 225                 230

Thr Arg Pro Ala Gly Asp Gly Thr Phe Gln Lys Trp Ala Ala Val Val
            235                 240                 245

Val Pro Ser Gly Gln Glu Gln Arg Tyr Thr Cys His Val Gln His Glu
            250                 255                 260

Gly Leu Pro Lys Pro Leu Thr Leu Pro Trp Glu Pro Ser Ser Gln Pro
265                 270                 275                 280

Thr Ile Pro Ile Val Gly Ile Ile Ala Gly Leu Val Leu Phe Gly Ala
            285                 290                 295

Val Ile Thr Gly Ala Val Val Ala Ala Val Met Trp Arg Arg Lys Ser

```
                    300                 305                 310
Ser Asp Arg Lys Gly Gly Ser Tyr Ser Gln Ala Ala Ser Ser Asp Ser
            315                 320                 325

Ala Gln Gly Ser Asp Val Ser Leu Thr Ala Cys Lys Val
            330                 335                 340
```

(2) INFORMATION FOR SEQ ID NO:102:

(i) SEQUENCE CHARACTERISTICS:
      (A) LENGTH: 365 amino acids
      (B) TYPE: amino acid
      (D) TOPOLOGY: linear (ii) MOLECULE TYPE: peptide (xi) SEQUENCE DESCRIPTION: SEQ ID NO:102:

```
Met Ala Val Met Ala Pro Arg Thr Leu Val Leu Leu Leu Ser Gly Ala
-24             -20                 -15                 -10

Leu Ala Leu Thr Gln Thr Trp Ala Gly Ser His Ser Met Arg Tyr Phe
            -5                  1                   5

Tyr Thr Ser Met Ser Arg Pro Gly Arg Gly Glu Pro Arg Phe Ile Ala
        10                  15                  20

Val Gly Tyr Val Asp Asp Thr Gln Phe Val Arg Phe Asp Ser Asp Ala
25                  30                  35                  40

Ala Ser Arg Arg Met Glu Pro Arg Ala Pro Trp Ile Glu Gln Glu Gly
            45                  50                  55

Pro Glu Tyr Trp Asp Arg Asn Thr Arg Asn Val Lys Ala Gln Ser Gln
            60                  65                  70

Thr Asp Arg Val Asp Leu Ser Thr Leu Arg Gly Tyr Tyr Asn Gln Ser
            75                  80                  85

Glu Ala Gly Ser His Thr Ile Gln Arg Met Tyr Gly Cys Asp Val Gly
90                  95                  100

Phe Asp Gly Arg Phe Leu Arg Gly Tyr Arg Gln Asp Ala Tyr Asp Gly
105                 110                 115                 120

Lys Asp Tyr Ile Ala Leu Lys Glu Asp Leu Arg Ser Trp Thr Ala Ala
            125                 130                 135

Asp Met Ala Ala Gln Thr Thr Lys His Lys Trp Glu Ala Ala His Val
            140                 145                 150

Ala Glu Gln Trp Arg Ala Tyr Leu Glu Gly Thr Cys Val Glu Trp Leu
            155                 160                 165

Arg Arg Tyr Leu Glu Asn Gly Lys Glu Thr Leu Gln Arg Thr Asp Ala
            170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
            205                 210                 215

Trp Gln Arg Asp Gly Glu Asp Gln Thr Gln Asp Thr Glu Leu Val Glu
            220                 225                 230

Thr Arg Pro Ala Gly Asp Gly Thr Phe Gln Lys Trp Val Ala Val Val
            235                 240                 245

Val Pro Ser Gly Gln Glu Gln Arg Tyr Thr Cys His Val Gln His Glu
250                 255                 260

Gly Leu Pro Lys Pro Leu Thr Leu Pro Trp Glu Pro Ser Ser Gln Pro
265                 270                 275                 280

Thr Ile Pro Ile Val Gly Ile Ile Ala Gly Leu Val Leu Phe Gly Ala
            285                 290                 295
```

```
Val Ile Thr Gly Ala Val Val Ala Ala Val Met Trp Arg Arg Lys Ser
            300                 305                 310

Ser Asp Arg Lys Gly Gly Ser Tyr Ser Gln Ala Ala Ser Ser Asp Ser
            315                 320                 325

Ala Gln Gly Ser Asp Val Ser Leu Thr Ala Cys Lys Val
            330                 335                 340
```

(2) INFORMATION FOR SEQ ID NO:103:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:103:

```
Met Ala Val Met Ala Pro Arg Thr Leu Val Leu Leu Leu Ser Gly Ala
-24             -20                 -15                 -10

Leu Ala Leu Thr Gln Thr Trp Ala Gly Ser His Ser Met Arg Tyr Phe
            -5                   1                   5

Tyr Thr Ser Met Ser Arg Pro Gly Arg Gly Glu Pro Arg Phe Ile Ala
            10                  15                  20

Val Gly Tyr Val Asp Asp Thr Gln Phe Val Arg Phe Asp Ser Asp Ala
25                  30                  35                  40

Ala Ser Gln Arg Met Glu Pro Arg Ala Pro Trp Ile Glu Gln Glu Gly
            45                  50                  55

Pro Glu Tyr Trp Asp Arg Asn Thr Arg Asn Val Lys Ala Gln Ser Gln
            60                  65                  70

Thr Asp Arg Val Asp Leu Ser Thr Leu Arg Gly Tyr Tyr Asn Gln Ser
            75                  80                  85

Glu Ala Gly Ser His Thr Ile Gln Arg Met Tyr Gly Cys Asp Val Gly
            90                  95                  100

Phe Asp Gly Arg Phe Leu Arg Gly Tyr Arg Gln Asp Ala Tyr Asp Gly
105                 110                 115                 120

Lys Asp Tyr Ile Ala Leu Lys Glu Asp Leu Arg Ser Trp Thr Ala Ala
            125                 130                 135

Asp Met Ala Ala Gln Thr Thr Lys His Lys Trp Glu Ala Ala His Val
            140                 145                 150

Ala Glu Gln Trp Arg Ala Tyr Leu Glu Gly Thr Cys Val Glu Trp Leu
            155                 160                 165

Arg Arg Tyr Leu Glu Asn Gly Lys Glu Thr Leu Gln Arg Thr Asp Ala
            170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
            205                 210                 215

Trp Gln Arg Asp Gly Glu Asp Gln Thr Gln Asp Thr Glu Leu Val Glu
            220                 225                 230

Thr Arg Pro Ala Gly Asp Gly Thr Phe Gln Lys Trp Val Ala Val Val
            235                 240                 245

Val Pro Ser Gly Gln Glu Gln Arg Tyr Thr Cys His Val Gln His Glu
250                 255                 260

Gly Leu Pro Lys Pro Leu Thr Leu Pro Trp Glu Pro Ser Ser Gln Pro
265                 270                 275                 280
```

```
Thr Ile Pro Ile Val Gly Ile Ile Ala Gly Leu Val Leu Phe Gly Ala
            285                 290                 295

Val Ile Thr Gly Ala Val Val Ala Ala Val Met Trp Arg Arg Lys Ser
            300                 305                 310

Ser Asp Arg Lys Gly Gly Ser Tyr Ser Gln Ala Ala Ser Ser Asp Ser
            315                 320                 325

Ala Gln Gly Ser Asp Val Ser Leu Thr Ala Cys Lys Val
            330                 335                 340

(2) INFORMATION FOR SEQ ID NO:104:

(i) SEQUENCE CHARACTERISTICS:
        (A) LENGTH: 365 amino acids
        (B) TYPE: amino acid
        (D) TOPOLOGY: linear (ii) MOLECULE TYPE: peptide (xi) SEQUENCE DESCRIPTION: SEQ ID NO:104:

Met Ala Val Met Ala Pro Arg Thr Leu Val Leu Leu Ser Gly Ala
-24             -20                 -15                 -10

Leu Ala Leu Thr Gln Thr Trp Ala Gly Ser His Ser Met Arg Tyr Phe
            -5                  1                   5

Tyr Thr Ser Val Ser Arg Pro Gly Arg Gly Glu Pro Arg Phe Ile Ala
            10                  15                  20

Val Gly Tyr Val Asp Asp Thr Gln Phe Val Arg Phe Asp Ser Asp Ala
25                  30                  35                  40

Ala Ser Gln Arg Met Glu Pro Arg Ala Pro Trp Ile Glu Gln Glu Gly
            45                  50                  55

Pro Glu Tyr Trp Asp Phe Asn Thr Arg Asn Val Lys Ala Gln Ser Gln
            60                  65                  70

Thr Asp Arg Val Asp Leu Ser Thr Leu Arg Gly Tyr Tyr Asn Gln Ser
            75                  80                  85

Glu Ala Gly Ser His Thr Ile Gln Met Met Tyr Gly Cys Asp Val Gly
            90                  95                  100

Ser Asp Gly Arg Phe Leu Arg Gly Tyr Arg Gln Asp Ala Tyr Asp Gly
105                 110                 115                 120

Lys Asp Tyr Ile Ala Leu Lys Glu Asp Leu Arg Ser Trp Thr Ala Ala
            125                 130                 135

Asp Met Ala Ala Gln Thr Thr Lys His Lys Trp Glu Ala Ala His Val
            140                 145                 150

Ala Glu Gln Trp Arg Ala Tyr Leu Glu Gly Thr Cys Val Glu Trp Leu
            155                 160                 165

Arg Arg Tyr Leu Glu Asn Gly Lys Glu Thr Leu Gln Arg Thr Asp Ala
            170                 175                 180

Pro Lys Thr His Met Thr His His Ala Val Ser Asp His Glu Ala Thr
185                 190                 195                 200

Leu Arg Cys Trp Ala Leu Ser Phe Tyr Pro Ala Glu Ile Thr Leu Thr
            205                 210                 215

Trp Gln Arg Asp Gly Glu Asp Gln Thr Gln Asp Thr Glu Leu Val Glu
            220                 225                 230

Thr Arg Pro Ala Gly Asp Gly Thr Phe Gln Lys Trp Val Ala Val Val
            235                 240                 245

Val Pro Ser Gly Gln Glu Gln Arg Tyr Thr Cys His Val Gln His Glu
            250                 255                 260

Gly Leu Pro Lys Pro Leu Thr Leu Pro Trp Glu Pro Ser Ser Gln Pro
```

```
                265                 270                 275                 280
Thr Ile Pro Ile Val Gly Ile Ile Ala Gly Leu Val Leu Phe Gly Ala
                    285                 290                 295
Val Ile Thr Gly Ala Val Val Ala Ala Val Met Trp Arg Arg Lys Ser
                300                 305                 310
Ser Asp Arg Lys Gly Gly Ser Tyr Ser Gln Ala Ala Ser Ser Asp Ser
            315                 320                 325
Ala Gln Gly Ser Asp Val Ser Leu Thr Ala Cys Lys Val
            330                 335                 340
```

(2) INFORMATION FOR SEQ ID NO:105:

(i) SEQUENCE CHARACTERISTICS:
        (A) LENGTH: 274 amino acids
        (B) TYPE: amino acid
        (D) TOPOLOGY: linear (ii) MOLECULE TYPE: peptide (xi) SEQUENCE DESCRIPTION: SEQ ID NO:105:

```
Gly Ser His Ser Met Arg Tyr Phe Phe Thr Ser Val Ser Arg Pro Gly
1               5                   10                  15
Arg Gly Glu Pro Arg Phe Ile Ala Val Gly Tyr Val Asp Asp Thr Gln
                20                  25                  30
Phe Val Arg Phe Asp Ser Asp Ala Ala Ser Gln Arg Met Glu Pro Arg
            35                  40                  45
Ala Pro Trp Ile Glu Gln Glu Gly Pro Glu Tyr Trp Asp Gly Glu Thr
        50                  55                  60
Arg Lys Val Lys Ala His Ser Gln Thr His Arg Val Asp Leu Ser Thr
65                  70                  75                  80
Leu Arg Gly Tyr Tyr Asn Gln Ser Glu Ala Gly Ser His Thr Val Gln
                85                  90                  95
Arg Met Cys Gly Cys Asp Val Gly Ser Asp Trp Arg Phe Leu Arg Gly
                100                 105                 110
Tyr His Gln Tyr Ala Tyr Asp Gly Lys Asp Tyr Ile Ala Leu Lys Glu
            115                 120                 125
Asp Leu Arg Ser Trp Thr Ala Ala Asp Met Ala Ala Gln Thr Thr Lys
        130                 135                 140
His Lys Trp Glu Ala Ala His Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr Asp Ala Pro Lys Thr His Met Thr His His
            180                 185                 190
Ala Val Ser Asp His Glu Ala Thr Leu Arg Cys Trp Ala Leu Ser Phe
            195                 200                 205
Tyr Pro Ala Glu Ile Thr Leu Thr Trp Gln Arg Asp Gly Glu Asp Gln
        210                 215                 220
Thr Gln Asp Thr Glu Leu Val Glu Thr Arg Pro Ala Gly Asp Gly Thr
225                 230                 235                 240
Phe Gln Lys Trp Ala Ala Val Val Val Pro Ser Gly Gln Glu Gln Arg
                245                 250                 255
Tyr Thr Cys His Val Gln His Glu Gly Leu Pro Lys Pro Leu Thr Leu
            260                 265                 270
Pro Trp
```

(2) INFORMATION FOR SEQ ID NO:106:

(i) SEQUENCE CHARACTERISTICS:
        (A) LENGTH: 274 amino acids
        (B) TYPE: amino acid
        (D) TOPOLOGY: linear (ii) MOLECULE TYPE: peptide (xi) SEQUENCE DESCRIPTION: SEQ ID NO:106:

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Ser Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Ser Asp Trp Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Glu Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Pro Trp
```

(2) INFORMATION FOR SEQ ID NO:107:

(i) SEQUENCE CHARACTERISTICS:
        (A) LENGTH: 274 amino acids
        (B) TYPE: amino acid
        (D) TOPOLOGY: linear (ii) MOLECULE TYPE: peptide (xi) SEQUENCE DESCRIPTION: SEQ ID NO:107:

```
Gly Ser His Ser Met Arg Tyr Phe Phe Thr Ser Val Ser Arg Pro Gly
1               5                   10                  15
```

```
Arg Gly Glu Pro Arg Phe Ile Ala Val Gly Tyr Val Asp Asp Thr Gln
            20                  25                  30

Phe Val Arg Phe Asp Ser Asp Ala Ala Ser Arg Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Ser Thr
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Pro Trp (2) INFORMATION FOR SEQ ID NO:108:

(i) SEQUENCE CHARACTERISTICS:
        (A) LENGTH: 274 amino acids
        (B) TYPE: amino acid
        (D) TOPOLOGY: linear (ii) MOLECULE TYPE: peptide (xi) SEQUENCE DESCRIPTION: SEQ ID NO:108:

Gly Ser His Ser Met Arg Tyr Phe Tyr Thr Ser Val Ser Arg Pro Gly
1               5                  10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Arg Arg Met Glu Pro Arg
        35                  40                  45

Ala Pro Trp Ile Glu Gln Glu Gly Pro Glu Tyr Trp Asp Gly Glu Thr
    50                  55                  60

Arg Asn Val Lys Ala His Ser Gln Thr His Arg Val Asp Leu Ser Thr
65                  70                  75                  80

Leu Arg Gly Tyr Tyr Asn Gln Ser Glu Ala Gly Ser His Thr Leu Gln
```

```
                      85                  90                  95
Arg Met Tyr Gly Cys Asp Val Gly Ser Asp Trp Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Asp Met Ala Gln Thr Thr Lys
        130                 135                 140

His Lys Trp Glu Ala Ala His Val Ala Glu Gln Trp Arg Ala Tyr Leu
145                 150                 155                 160

Glu Gly Thr Cys Val Glu Trp Leu Arg Tyr Leu Glu Asn Gly Lys
                165                 170                 175

Glu Thr Leu Gln Arg Thr Asp Ala Pro Lys Thr His Met Thr His His
                180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Pro Trp (2) INFORMATION FOR SEQ ID NO:109:

(i) SEQUENCE CHARACTERISTICS:
        (A) LENGTH: 253 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 7
        (D) OTHER INFORMATION: /note= "Xaa is an unidentified
            amino acid residue."

(xi) SEQUENCE DESCRIPTION: SEQ ID NO:109:

Met Ala Ile Ser Gly Val Pro Val Leu Gly Phe Phe Ile Ile Ala Val
-25                 -20                 -15                 -10

Leu Met Ser Ala Gln Glu Ser Trp Ala Ile Lys Glu Glu His Val Xaa
            -5                   1                   5

Ile Ile Gln Ala Glu Phe Tyr Leu Asn Pro Asp Gln Ser Gly Glu Phe
                10                  15                  20

Met Phe Asp Phe Asp Gly Asp Glu Ile Phe His Val Asp Met Ala Lys
                25                  30                  35

Lys Glu Thr Val Trp Arg Leu Glu Glu Phe Gly Arg Phe Ala Ser Phe
40                  45                  50                  55

Glu Ala Gln Gly Ala Leu Ala Asn Ile Ala Val Asp Lys Ala Asn Leu
                60                  65                  70

Glu Ile Met Thr Lys Arg Ser Asn Tyr Thr Pro Ile Thr Asn Val Pro
            75                  80                  85

Pro Glu Val Thr Val Leu Thr Asn Ser Pro Val Glu Leu Arg Glu Pro
            90                  95                  100
```

-continued

```
Asn Val Leu Ile Cys Phe Ile Asp Lys Phe Thr Pro Val Val Asn
    105                 110                 115

Val Thr Trp Leu Arg Asn Gly Lys Pro Val Thr Thr Gly Val Ser Glu
120                 125                 130                 135

Thr Val Phe Leu Pro Arg Glu Asp His Leu Phe Arg Lys Phe His Tyr
                140                 145                 150

Leu Pro Phe Leu Pro Ser Thr Glu Asp Val Tyr Asp Cys Arg Val Glu
                155                 160                 165

His Trp Gly Leu Asp Glu Pro Leu Leu Lys His Trp Glu Phe Asp Ala
                170                 175                 180

Pro Ser Pro Leu Pro Glu Thr Thr Glu Asn Val Val Cys Ala Leu Thr
                185                 190                 195

Val Gly Leu Val Gly Ile Ile Ile Gly Thr Ile Phe Ile Ile Lys Gly
200                 205                 210                 215

Leu Arg Lys Ser Asn Ala Ala Glu Arg Arg Gly Pro Leu
                220                 225
```

(2) INFORMATION FOR SEQ ID NO:110:

(i) SEQUENCE CHARACTERISTICS:
(A) LENGTH: 255 amino acids
(B) TYPE: amino acid
(D) TOPOLOGY: linear (ii) MOLECULE TYPE: peptide (xi) SEQUENCE DESCRIPTION: SEQ ID NO:110:

```
Met Ile Leu Asn Lys Ala Leu Leu Gly Ala Leu Ala Leu Thr Thr
-25                 -20                 -15                 -10

Val Met Ser Pro Cys Gly Gly Glu Asp Ile Val Ala Asp His Val Ala
                -5                   1                   5

Ser Cys Gly Val Asn Leu Tyr Gln Phe Tyr Gly Pro Ser Gly Gln Tyr
        10                  15                  20

Thr His Glu Phe Asp Gly Asp Glu Gln Phe Tyr Val Asp Leu Glu Arg
        25                  30                  35

Lys Glu Thr Ala Trp Arg Trp Pro Glu Phe Ser Lys Phe Gly Gly Phe
40                  45                  50                  55

Asp Pro Gln Gly Ala Leu Arg Asn Met Ala Val Ala Lys His Asn Leu
                60                  65                  70

Asn Ile Met Ile Lys Arg Tyr Asn Ser Thr Ala Ala Thr Asn Glu Val
            75                  80                  85

Pro Glu Val Thr Val Phe Ser Lys Ser Pro Val Thr Leu Gly Gln Pro
                90                  95                  100

Asn Thr Leu Ile Cys Leu Val Asp Asn Ile Phe Pro Pro Val Val Asn
    105                 110                 115

Ile Thr Trp Leu Ser Asn Gly Gln Ser Val Thr Glu Asp Val Ser Glu
120                 125                 130                 135

Thr Ser Phe Leu Ser Lys Ser Asp His Ser Phe Phe Lys Ile Ser Tyr
                140                 145                 150

Leu Thr Phe Leu Pro Ser Ala Asp Glu Ile Tyr Asp Cys Lys Val Glu
                155                 160                 165

His Trp Gly Leu Asp Gln Pro Leu Leu Lys His Trp Glu Pro Glu Ile
                170                 175                 180

Pro Ala Pro Met Ser Glu Leu Thr Glu Thr Val Val Cys Ala Leu Gly
                185                 190                 195

Leu Ser Val Gly Leu Met Gly Ile Val Val Gly Thr Val Phe Ile Ile
```

```
                        200             205             210             215
        Gln Gly Leu Arg Ser Val Gly Ala Ser Arg His Gln Gly Pro Leu
                        220             225             230
```

(2) INFORMATION FOR SEQ ID NO:111:

(i) SEQUENCE CHARACTERISTICS:
        (A) LENGTH: 261 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 7
        (D) OTHER INFORMATION: /note= "Xaa is an unidentified
           amino acid residue."

(xi) SEQUENCE DESCRIPTION: SEQ ID NO:111:

```
Met Arg Pro Glu Asp Arg Met Phe His Ile Arg Ala Val Ile Leu Arg
    -30             -25             -20
Ala Leu Ser Leu Ala Phe Leu Leu Ser Leu Arg Gly Ala Gly Ala Ile
-15             -10              -5                               1
Lys Ala Asp His Val Xaa Ser Thr Tyr Ala Ala Phe Val Gln Thr His
                 5              10              15
Arg Pro Thr Gly Glu Phe Met Phe Glu Phe Asp Glu Asp Glu Met Phe
                20              25              30
Tyr Val Asp Leu Asp Lys Lys Glu Thr Val Trp His Leu Glu Glu Phe
    35              40              45
Gly Gln Ala Phe Ser Phe Glu Ala Gln Gly Gly Leu Ala Asn Ile Ala
50              55              60              65
Ile Leu Asn Asn Asn Leu Asn Thr Leu Ile Gln Arg Ser Asn His Thr
                70              75              80
Gln Ala Thr Asn Asp Pro Pro Glu Val Thr Val Phe Pro Lys Glu Pro
                85              90              95
Val Glu Leu Gly Gln Pro Asn Thr Leu Ile Cys His Ile Asp Lys Phe
                100             105             110
Phe Pro Pro Val Leu Asn Val Thr Trp Leu Cys Asn Gly Glu Leu Val
    115             120             125
Thr Glu Gly Val Ala Glu Ser Leu Phe Leu Pro Arg Thr Asp Tyr Ser
130             135             140             145
Phe His Lys Phe His Tyr Leu Thr Phe Val Pro Ser Ala Glu Asp Phe
                150             155             160
Tyr Asp Cys Arg Val Glu His Trp Gly Leu Asp Gln Pro Leu Leu Lys
                165             170             175
His Trp Glu Ala Gln Glu Pro Ile Gln Met Pro Glu Thr Thr Glu Thr
                180             185             190
Val Leu Cys Ala Leu Gly Leu Val Leu Gly Leu Val Gly Phe Ile Val
    195             200             205
Gly Thr Val Leu Ile Ile Lys Ser Leu Arg Ser Gly His Asp Pro Arg
210             215             220             225
Ala Gln Gly Thr Leu
                230
```

(2) INFORMATION FOR SEQ ID NO:112:

(i) SEQUENCE CHARACTERISTICS:
        (A) LENGTH: 250 amino acids (B) TYPE: amino acid
            (D) TOPOLOGY: linear (ii) MOLECULE TYPE: peptide (xi) SEQUENCE DESCRIPTION: SEQ ID NO:112:

Met Ala Leu Arg Ala Gly Leu Val Leu Gly Phe His Thr Leu Met Thr
-25             -20                 -15                 -10

Leu Leu Ser Pro Gln Glu Ala Gly Ala Thr Lys Ala Asp His Met Gly
            -5                  1               5

Ser Tyr Gly Pro Ala Phe Tyr Gln Ser Tyr Gly Ala Ser Gly Gln Phe
        10                  15                  20

Thr His Glu Phe Asp Glu Gln Leu Phe Ser Val Asp Leu Lys Lys
    25                  30                  35

Ser Glu Ala Val Trp Arg Leu Pro Glu Phe Gly Asp Phe Ala Arg Phe
40                  45                  50                  55

Asp Pro Gln Gly Gly Leu Ala Gly Ile Ala Ile Lys Ala His Leu
                60                  65                  70

Asp Ile Leu Val Glu Arg Ser Asn Arg Ser Arg Ala Ile Asn Val Pro
            75                  80                  85

Pro Arg Val Thr Val Leu Pro Lys Ser Arg Val Glu Leu Gly Gln Pro
        90                  95                  100

Asn Ile Leu Ile Cys Ile Val Asp Asn Ile Phe Pro Pro Val Ile Asn
    105                 110                 115

Ile Thr Trp Leu Arg Asn Gly Gln Thr Val Thr Glu Gly Val Ala Gln
120                 125                 130                 135

Thr Ser Phe Tyr Ser Gln Pro Asp His Leu Phe Arg Lys Phe His Tyr
                140                 145                 150

Leu Pro Phe Val Pro Ser Ala Glu Asp Val Tyr Asp Cys Gln Val Glu
            155                 160                 165

His Trp Gly Leu Asp Ala Pro Leu Leu Arg His Trp Glu Leu Gln Val
        170                 175                 180

Pro Ile Pro Pro Pro Asp Ala Met Glu Thr Leu Val Cys Ala Leu Gly
    185                 190                 195

Leu Ala Ile Gly Leu Val Gly Phe Leu Val Gly Thr Val Leu Ile Ile
200                 205                 210                 215

Met Gly Thr Tyr Val Ser Ser Val Pro Arg
                220                 225

(2) INFORMATION FOR SEQ ID NO:113:

(i) SEQUENCE CHARACTERISTICS:
        (A) LENGTH: 256 amino acids
        (B) TYPE: amino acid
        (D) TOPOLOGY: linear (ii) MOLECULE TYPE: peptide (xi) SEQUENCE DESCRIPTION: SEQ ID NO:113:

Met Pro Arg Ser Arg Ala Leu Ile Leu Gly Val Leu Ala Leu Thr Thr
-25             -20                 -15                 -10

Met Leu Ser Leu Cys Gly Gly Glu Asp Asp Ile Glu Ala Asp His Val
            -5                  1               5

Gly Ser Tyr Gly Ile Thr Phe Tyr Gln Ser Pro Gly Asp Ile Gly Gln
        10                  15                  20

Tyr Thr Phe Glu Phe Asp Gly Asp Glu Leu Phe Tyr Val Asp Leu Asp
    25                  30                  35

-continued

```
Lys Lys Glu Thr Val Trp Met Leu Pro Glu Phe Ala Gln Leu Arg Arg
 40              45                  50                  55

Phe Glu Pro Gln Gly Gly Leu Gln Asn Ile Ala Thr Gly Lys His Asn
             60                  65                  70

Leu Glu Ile Leu Thr Lys Arg Ser Asn Ser Thr Pro Ala Thr Asn Glu
             75                  80                  85

Ala Pro Gln Ala Thr Val Phe Pro Lys Ser Pro Val Leu Leu Gly Gln
             90                  95                 100

Pro Asn Thr Leu Ile Cys Phe Val Asp Asn Ile Phe Pro Pro Val Ile
            105                 110                 115

Asn Ile Thr Trp Leu Arg Asn Ser Lys Ser Val Thr Asp Gly Val Tyr
120                 125                 130                 135

Glu Thr Ser Phe Phe Val Asn Arg Asp Tyr Ser Phe His Lys Leu Ser
                140                 145                 150

Tyr Leu Thr Phe Ile Pro Ser Asp Asp Asp Ile Tyr Asp Cys Lys Val
                155                 160                 165

Glu His Trp Gly Leu Glu Glu Pro Val Leu Lys His Trp Glu Pro Glu
                170                 175                 180

Ile Pro Ala Pro Met Ser Glu Leu Thr Glu Thr Val Val Cys Ala Leu
185                 190                 195

Gly Leu Ser Val Gly Leu Val Gly Ile Val Val Gly Thr Ile Phe Ile
200                 205                 210                 215

Ile Gln Gly Leu Arg Ser Gly Gly Thr Ser Arg His Pro Gly Pro Leu
                220                 225                 230
```

(2) INFORMATION FOR SEQ ID NO:114:

(i) SEQUENCE CHARACTERISTICS:
        (A) LENGTH: 256 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 7
        (D) OTHER INFORMATION: /note= "Xaa is an unidentified
            amino acid residue."

(xi) SEQUENCE DESCRIPTION: SEQ ID NO:114:

```
Met Ala Thr Ile Gly Ala Leu Val Leu Arg Phe Phe Ile Ala Val
-25                 -20                 -15                 -10

Leu Met Ser Ser Gln Lys Ser Trp Ala Ile Lys Glu Glu His Thr Xaa
             -5                   1                   5

Ile Ile Gln Ala Glu Phe Tyr Leu Leu Pro Asp Lys Arg Gly Glu Phe
             10                  15                  20

Met Phe Asp Phe Asp Gly Asp Glu Ile Phe His Val Asp Ile Glu Lys
             25                  30                  35

Ser Glu Thr Ile Trp Arg Leu Glu Glu Phe Ala Lys Phe Ala Ser Phe
 40              45                  50                  55

Glu Ala Gln Gly Ala Leu Ala Asn Ile Ala Val Asp Lys Ala Asn Leu
             60                  65                  70

Asp Val Met Lys Glu Arg Ser Asn Asn Thr Pro Ser Ala Asn Val Ala
             75                  80                  85

Pro Glu Val Thr Val Leu Ser Arg Ser Pro Val Asn Leu Gly Glu Pro
             90                  95                 100

Asn Ile Leu Ile Cys Phe Ile Asp Lys Phe Ser Pro Pro Val Val Asn
```

-continued

```
            105                 110                 115
Val Thr Trp Leu Arg Asn Gly Arg Pro Val Thr Glu Gly Val Ser Glu
120                 125                 130                 135

Thr Val Phe Leu Pro Arg Asp Asp His Leu Phe Arg Lys Phe His Tyr
                140                 145                 150

Leu Thr Phe Leu Pro Ser Thr Asp Asp Phe Tyr Asp Cys Glu Val Asp
                155                 160                 165

His Trp Gly Leu Glu Glu Pro Leu Arg Lys Ala Trp Glu Phe Glu Glu
                170                 175                 180

Lys Thr Leu Leu Pro Glu Thr Lys Glu Asn Val Val Cys Ala Leu Gly
                185                 190                 195

Leu Phe Val Gly Leu Val Gly Ile Val Val Gly Ile Ile Leu Ile Met
200                 205                 210                 215

Lys Gly Ile Lys Lys Arg Asn Val Val Glu Arg Arg Gln Gly Ala Leu
                220                 225                 230
```

(2) INFORMATION FOR SEQ ID NO:115:

(i) SEQUENCE CHARACTERISTICS:
        (A) LENGTH: 266 amino acids
        (B) TYPE: amino acid
        (D) TOPOLOGY: linear (ii) MOLECULE TYPE: peptide (xi) SEQUENCE DESCRIPTION: SEQ ID NO:115:

```
Met Val Cys Leu Lys Leu Pro Gly Gly Ser Cys Met Thr Ala Leu Thr
-29             -25                 -20                 -15

Val Thr Leu Met Val Leu Ser Ser Pro Leu Ala Leu Ala Gly Asp Thr
                -10                 -5                  1

Arg Pro Arg Phe Leu Trp Gln Leu Lys Phe Glu Cys His Phe Phe Asn
            5                   10                  15

Gly Thr Glu Arg Val Arg Leu Leu Glu Arg Cys Ile Tyr Asn Gln Glu
            20                  25                  30

Glu Ser Val Arg Phe Asp Ser Asp Val Gly Glu Tyr Arg Ala Val Thr
35                  40                  45                  50

Glu Leu Gly Arg Pro Asp Ala Glu Tyr Trp Asn Ser Gln Lys Asp Leu
                55                  60                  65

Leu Glu Gln Arg Arg Ala Ala Val Asp Thr Tyr Cys Arg His Asn Tyr
            70                  75                  80

Gly Val Gly Glu Ser Phe Thr Val Gln Arg Arg Val Glu Pro Lys Val
            85                  90                  95

Thr Val Tyr Pro Ser Lys Thr Gln Pro Leu Gln His His Asn Leu Leu
            100                 105                 110

Val Cys Ser Val Ser Gly Phe Tyr Pro Gly Ser Ile Glu Val Arg Trp
115                 120                 125                 130

Phe Arg Asn Gly Gln Glu Glu Lys Ala Gly Val Val Ser Thr Gly Leu
                135                 140                 145

Ile Gln Asn Gly Asp Trp Thr Phe Gln Thr Leu Val Met Leu Glu Thr
                150                 155                 160

Val Pro Arg Ser Gly Glu Val Tyr Thr Cys Gln Val Glu His Pro Ser
            165                 170                 175

Val Thr Ser Pro Leu Thr Val Glu Trp Arg Ala Arg Ser Glu Ser Ala
            180                 185                 190

Gln Ser Lys Met Leu Ser Gly Val Gly Gly Phe Val Leu Gly Leu Leu
195                 200                 205                 210
```

```
Phe Leu Gly Ala Gly Leu Phe Ile Tyr Phe Arg Asn Gln Lys Gly His
            215                 220                 225

Ser Gly Leu Gln Pro Thr Gly Phe Leu Ser
            230                 235
```

(2) INFORMATION FOR SEQ ID NO:116:

(i) SEQUENCE CHARACTERISTICS:
        (A) LENGTH: 269 amino acids
        (B) TYPE: amino acid
        (D) TOPOLOGY: linear (ii) MOLECULE TYPE: peptide (ix) FEATURE:
        (A) NAME/KEY: Region
        (B) LOCATION: 226..233
        (D) OTHER INFORMATION: /note= "Xaa is an unidentified
            amino acid residue."

(xi) SEQUENCE DESCRIPTION: SEQ ID NO:116:

```
Met Ser Trp Lys Lys Ser Leu Arg Ile Pro Gly Asp Leu Arg Val Ala
        -30                 -25                 -20

Thr Val Thr Leu Met Leu Ala Ile Leu Ser Ser Leu Ala Glu Gly
        -15                 -10                  -5

Arg Asp Ser Pro Glu Asp Phe Val Tyr Gln Phe Lys Gly Leu Cys Tyr
1                    5                  10                  15

Phe Thr Asn Gly Thr Glu Arg Val Arg Gly Val Thr Arg His Ile Tyr
                20                  25                  30

Asn Arg Glu Glu Tyr Val Arg Phe Asp Ser Asp Val Gly Val Tyr Arg
            35                  40                  45

Ala Val Thr Pro Gln Gly Arg Pro Val Ala Glu Tyr Trp Asn Ser Gln
50                  55                  60

Lys Glu Val Leu Glu Gly Ala Arg Ala Ser Val Asp Arg Val Cys Arg
65                  70                  75                  80

His Asn Tyr Glu Val Ala Tyr Arg Gly Ile Leu Gln Arg Arg Val Glu
                85                  90                  95

Pro Thr Val Thr Ile Ser Pro Ser Arg Thr Glu Ala Leu Asn His His
                100                 105                 110

Asn Leu Leu Ile Cys Ser Val Thr Asp Phe Tyr Pro Ser Gln Ile Lys
            115                 120                 125

Val Arg Trp Phe Arg Asn Asp Gln Glu Glu Thr Ala Gly Val Val Ser
            130                 135                 140

Thr Pro Leu Ile Arg Asn Gly Asp Trp Thr Phe Gln Ile Leu Val Met
145                 150                 155                 160

Leu Glu Met Thr Pro Gln Arg Gly Asp Val Tyr Thr Cys His Val Glu
                165                 170                 175

His Pro Ser Leu Gln Ser Pro Ile Thr Val Glu Trp Arg Ala Gln Ser
                180                 185                 190

Glu Ser Ala Gln Ser Lys Met Leu Ser Gly Val Gly Gly Phe Val Leu
            195                 200                 205

Gly Leu Ile Phe Leu Gly Leu Gly Leu Ile Ile Arg Gln Arg Ser Arg
        210                 215                 220

Lys Xaa Xaa Xaa Xaa Xaa Xaa Xaa Gly Leu Leu His
225                 230                 235
```

(2) INFORMATION FOR SEQ ID NO:117:

```
           (i) SEQUENCE CHARACTERISTICS:
               (A) LENGTH: 259 amino acids
               (B) TYPE: amino acid
               (D) TOPOLOGY: linear (ii) MOLECULE TYPE: peptide (ix) FEATURE:
               (A) NAME/KEY: Region
               (B) LOCATION: 24..25
               (D) OTHER INFORMATION: /note= "Xaa is an unidentified
                   amino acid residue."

(xi) SEQUENCE DESCRIPTION: SEQ ID NO:117:

Met Val Leu Gln Val Ser Ala Ala Pro Arg Thr Val Ala Leu Thr Ala
-28         -25                 -20                 -15

Leu Leu Met Val Leu Leu Thr Ser Val Val Gln Gly Arg Ala Thr Pro
        -10                  -5                   1

Glu Asn Tyr Leu Phe Gln Gly Arg Gln Glu Cys Tyr Ala Phe Asn Gly
 5              10                  15                  20

Thr Gln Arg Xaa Xaa Phe Leu Glu Arg Tyr Ile Tyr Asn Arg Glu Glu
                25                  30                  35

Phe Val Arg Phe Asp Ser Asp Val Gly Glu Phe Arg Ala Val Thr Glu
            40                  45                  50

Leu Gly Arg Pro Asp Glu Glu Tyr Trp Asn Ser Gln Lys Asp Ile Leu
        55                  60                  65

Glu Glu Glu Arg Ala Val Pro Asp Arg Met Cys Arg His Asn Tyr Glu
    70                  75                  80

Leu Gly Gly Pro Met Thr Leu Gln Arg Arg Val Gln Pro Arg Val Asn
85                  90                  95                 100

Val Ser Pro Ser Lys Lys Gly Pro Leu Gln His His Asn Leu Leu Val
                105                 110                 115

Cys His Val Thr Asp Phe Tyr Pro Gly Ser Ile Gln Val Arg Trp Phe
            120                 125                 130

Leu Asn Gly Gln Glu Glu Thr Ala Gly Val Val Ser Thr Asn Leu Ile
            135                 140                 145

Arg Asn Gly Asp Trp Thr Phe Gln Ile Leu Val Met Leu Glu Met Thr
150                 155                 160

Pro Gln Gln Gly Asp Val Tyr Thr Cys Gln Val Glu His Thr Ser Leu
165                 170                 175                 180

Asp Ser Pro Val Thr Val Glu Trp Lys Ala Gln Ser Asp Ser Ala Arg
                185                 190                 195

Ser Lys Thr Leu Thr Gly Ala Gly Gly Phe Val Leu Gly Leu Ile Ile
                200                 205                 210

Cys Gly Val Gly Ile Phe Met His Arg Arg Ser Lys Lys Val Gln Arg
            215                 220                 225

Gly Ser Ala
        230

(2) INFORMATION FOR SEQ ID NO:118:

(i) SEQUENCE CHARACTERISTICS:
               (A) LENGTH: 273 amino acids
               (B) TYPE: amino acid
               (D) TOPOLOGY: linear (ii) MOLECULE TYPE: peptide (xi) SEQUENCE DESCRIPTION: SEQ ID NO:118:

Met Gly Ser Gly Trp Val Pro Trp Val Val Ala Leu Leu Val Asn Leu
```

```
              -25                 -20                 -15
Thr Arg Leu Asp Ser Ser Met Thr Gln Gly Thr Asp Ser Pro Glu Asp
-10              -5                   1               5

Phe Val Ile Gln Ala Lys Ala Asp Cys Tyr Phe Thr Asn Gly Thr Glu
             10                  15                  20

Lys Val Gln Phe Val Val Arg Phe Ile Phe Asn Leu Glu Glu Tyr Val
             25                  30                  35

Arg Phe Asp Ser Asp Val Gly Met Phe Val Ala Leu Thr Lys Leu Gly
    40                  45                  50

Gln Pro Asp Ala Glu Gln Trp Asn Ser Arg Leu Asp Leu Leu Glu Arg
55                  60                  65                  70

Ser Arg Gln Ala Val Asp Gly Val Cys Arg His Asn Tyr Arg Leu Gly
                75                  80                  85

Ala Pro Phe Thr Val Gly Arg Lys Val Gln Pro Glu Val Thr Val Tyr
            90                  95                  100

Pro Glu Arg Thr Pro Leu Leu His Gln His Asn Leu Leu His Cys Ser
        105                 110                 115

Val Thr Gly Phe Tyr Pro Gly Asp Ile Lys Ile Lys Trp Phe Leu Asn
    120                 125                 130

Gly Gln Glu Glu Arg Ala Gly Val Met Ser Thr Gly Pro Ile Arg Asn
135                 140                 145                 150

Gly Asp Trp Thr Phe Gln Thr Val Val Met Leu Glu Met Thr Pro Glu
                155                 160                 165

Leu Gly His Val Tyr Thr Cys Leu Val Asp His Ser Ser Leu Leu Ser
            170                 175                 180

Pro Val Ser Val Glu Trp Arg Ala Gln Ser Glu Tyr Ser Trp Arg Lys
        185                 190                 195

Met Leu Ser Gly Ile Ala Ala Phe Leu Leu Gly Leu Ile Phe Leu Leu
    200                 205                 210

Val Gly Ile Val Ile Gln Leu Arg Ala Gln Lys Gly Tyr Val Arg Thr
215                 220                 225                 230

Gln Met Ser Gly Asn Glu Val Ser Arg Ala Val Leu Leu Pro Gln Ser
                235                 240                 245

Gln (2) INFORMATION FOR SEQ ID NO:119:

(i) SEQUENCE CHARACTERISTICS:
        (A) LENGTH: 265 amino acids
        (B) TYPE: amino acid
        (D) TOPOLOGY: linear (ii) MOLECULE TYPE: peptide (xi) SEQUENCE DESCRIPTION: SEQ ID NO:119:

Met Ala Leu Gln Ile Pro Ser Leu Leu Leu Ser Ala Ala Val Val Val
        -25                 -20                 -15

Leu Met Val Leu Ser Ser Pro Arg Thr Glu Gly Gly Asn Ser Glu Arg
    -10              -5                   1               5

His Phe Val Ala Gln Leu Lys Gly Glu Cys Tyr Phe Thr Asn Gly Thr
             10                  15                  20

Gln Arg Ile Arg Ser Val Asn Arg Tyr Ile Tyr Asn Arg Glu Glu Trp
             25                  30                  35

Val Arg Phe Asp Ser Asp Val Gly Glu Tyr Arg Ala Val Thr Glu Leu
    40                  45                  50
```

```
Gly Arg Pro Asp Ala Glu Tyr Trp Asn Ser Gln Pro Glu Ile Leu Glu
    55                  60                  65
Arg Thr Arg Ala Glu Val Asp Thr Val Cys Arg His Asn Tyr Glu Gly
 70              75                  80                      85
Val Glu Thr His Thr Ser Leu Arg Arg Leu Glu Gln Pro Asn Val Ala
                 90                  95                 100
Ile Ser Leu Ser Arg Thr Glu Ala Leu Asn His His Asn Thr Leu Val
            105                 110                 115
Cys Ser Val Thr Asp Phe Tyr Pro Ala Lys Ile Lys Val Arg Trp Phe
            120                 125                 130
Arg Asn Gly Gln Glu Glu Thr Val Gly Val Ser Ser Thr Gln Leu Ile
    135                 140                 145
Arg Asn Gly Asp Trp Thr Phe Gln Val Leu Val Met Leu Glu Met Thr
150                 155                 160                 165
Pro His Gln Gly Glu Val Tyr Thr Cys His Val Glu His Pro Ser Leu
                170                 175                 180
Lys Ser Pro Ile Thr Val Glu Trp Arg Ala Gln Ser Glu Ser Ala Arg
            185                 190                 195
Ser Lys Met Leu Ser Gly Ile Gly Gly Cys Val Leu Gly Val Ile Phe
    200                 205                 210
Leu Gly Leu Gly Leu Phe Ile Arg His Arg Ser Gln Lys Gly Pro Arg
    215                 220                 225
Gly Pro Pro Pro Ala Gly Leu Leu Gln
230                 235

(2) INFORMATION FOR SEQ ID NO:120:

(i) SEQUENCE CHARACTERISTICS:
        (A) LENGTH: 264 amino acids
        (B) TYPE: amino acid
        (D) TOPOLOGY: linear (ii) MOLECULE TYPE: peptide (xi) SEQUENCE DESCRIPTION: SEQ ID NO:120:

Met Val Trp Leu Pro Arg Val Pro Cys Val Ala Ala Val Ile Leu Leu
        -25                 -20                 -15
Leu Thr Val Leu Ser Pro Pro Val Ala Leu Val Arg Asp Thr Pro Pro
    -10              -5                   1                   5
Arg Phe Leu Glu Tyr Val Thr Ser Glu Cys His Phe Tyr Asn Gly Thr
                 10                  15                  20
Gln His Val Arg Phe Leu Glu Arg Phe Ile Tyr Asn Arg Glu Glu Asn
             25                  30                  35
Leu Arg Phe Asp Ser Asp Val Gly Glu Tyr Arg Ala Val Thr Glu Leu
         40                  45                  50
Gly Arg Pro Asp Ala Glu Asn Trp Asn Ser Gln Pro Glu Ile Leu Glu
    55                  60                  65
Asp Ala Arg Ala Ser Val Asp Thr Tyr Cys Arg His Asn Tyr Glu Ile
 70              75                  80                      85
Ser Asp Lys Phe Leu Val Arg Arg Val Glu Pro Thr Val Thr Val
                 90                  95                 100
Tyr Pro Thr Lys Thr Gln Pro Leu Glu His His Asn Leu Leu Val Cys
            105                 110                 115
Ser Val Ser Asp Phe Tyr Pro Gly Asn Ile Glu Val Arg Trp Phe Arg
            120                 125                 130
Asn Gly Lys Glu Glu Glu Thr Gly Ile Val Ser Thr Gly Leu Val Arg
```

```
            135                 140                 145
Asn Gly Asp Trp Thr Phe Gln Thr Leu Val Met Leu Glu Trp Val Pro
150                 155                 160                 165

Gln Ser Gly Glu Val Tyr Thr Cys Gln Val Glu His Pro Ser Leu Thr
                170                 175                 180

Asp Pro Val Thr Val Glu Trp Lys Ala Gln Ser Thr Ser Ala Gln Asn
                185                 190                 195

Lys Met Leu Ser Gly Val Gly Gly Phe Val Leu Gly Leu Leu Phe Leu
            200                 205                 210

Gly Ala Gly Leu Phe Ile Tyr Phe Arg Asn Gln Lys Gly Gln Ser Glu
            215                 220                 225

Leu Gln Pro Thr Gly Leu Leu Ser
230                 235

(2) INFORMATION FOR SEQ ID NO:121:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:121:

Glu Phe Ser Lys Phe Gly
1               5

(2) INFORMATION FOR SEQ ID NO:122:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:122:

Val Leu Arg Gln Arg
1               5

(2) INFORMATION FOR SEQ ID NO:123:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:123:

Leu Phe Arg Arg Arg Arg
1               5

(2) INFORMATION FOR SEQ ID NO:124:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:124:

Glu Val Ala Tyr
1
```

-continued

```
(2) INFORMATION FOR SEQ ID NO:125:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:125:

Glu Val Ala Phe
1

(2) INFORMATION FOR SEQ ID NO:126:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:126:

Glu Val Ala Gly
1

(2) INFORMATION FOR SEQ ID NO:127:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:127:

Gln Leu Glu Leu
```